United States Patent
Lee et al.

(10) Patent No.: US 10,001,477 B2
(45) Date of Patent: Jun. 19, 2018

(54) USE OF PROTEIN NANOPARTICLE BASED HYDROGEL

(71) Applicant: KOREA UNIVERSITY RESEARCH AND BUSINESS FOUNDATION, Seoul (KR)

(72) Inventors: Jeewon Lee, Seoul (KR); Eun Jung Lee, Seoul (KR); Jong Hwan Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days. days.

(21) Appl. No.: 15/152,259

(22) Filed: May 11, 2016

(65) Prior Publication Data
US 2016/0349250 A1 Dec. 1, 2016

Related U.S. Application Data

(63) Continuation-in-part of application No. 13/938,575, filed on Jul. 10, 2013, now abandoned.

(30) Foreign Application Priority Data

Nov. 9, 2012 (KR) .................. 10-2012-0126843

(51) Int. Cl.
| | | |
|---|---|---|
| *C12Q 1/70* | (2006.01) | |
| *G01N 33/543* | (2006.01) | |
| *G01N 33/58* | (2006.01) | |
| *G01N 33/569* | (2006.01) | |

(52) U.S. Cl.
CPC .. *G01N 33/54346* (2013.01); *G01N 33/56988* (2013.01); *G01N 33/582* (2013.01); *G01N 2333/155* (2013.01)

(58) Field of Classification Search
None
See application file for complete search history.

(56) References Cited

FOREIGN PATENT DOCUMENTS

| KR | 1020070036187 A | 4/2007 | |
|---|---|---|---|
| KR | 1020077024561 A | 10/2007 | |
| KR | 1020110090347 A | 8/2011 | |
| WO | 2010/025190 A1 | 3/2010 | |
| WO | WO 2010/025190 A1 * | 3/2010 | ............... B82B 1/00 |

OTHER PUBLICATIONS

Hamlin et al. A novel ELISA using PVDF microplates. J. Neurosci. Met. 2005; 143: 163-168.*

(Continued)

*Primary Examiner* — Janet L Andres
*Assistant Examiner* — Stuart Snyder
(74) *Attorney, Agent, or Firm* — Ladas & Parry LLP; Loren K. Thompson

(57) ABSTRACT

The present invention relates to a use of a protein nanoparticle-based hydrogel, and more particularly, to a use of a protein nanoparticle-based hydrogel capable of highly sensitive and simultaneous multi-detection of disease markers by using a hydrogel within which protein nanoparticles presenting multiple copies of disease marker detection probes are immobilized.

19 Claims, 58 Drawing Sheets

(56) References Cited

OTHER PUBLICATIONS

M. Basri, et al; "Immobilization of Lipase on Poly(N-vinyl-2-pyrrolidone-co-styrene) Hydrogel", Journal of Applied Polymer Science, vol. 82, pp. 1404-1409; First published: Aug. 28, 2001.

Allison A. Ellington, et al; "Antibody-Based Protein Multiplex Platforms: Technical and Operational Challenges", Clinical Chemistry vol. 56:2; pp. 186-193; Feb. 2010.

Nader D. Halim, et al; "A novel ELISA using PVDF microplates", Journal of Neuroscience Methods 143; pp. 163-168; Apr. 30, 2005.

Douglas Hanahan; "Techniques for Transformation of E. coli", In: Glover D.M., editor. DNA cloning a practical approach. vol. 1, Oxford, United Kingdom: IRL Press: 1985, pp. 109-135.

Stephen F. Kingsmore: "Multiplexed protein measurement: technologies and applications of protein and antibody arrays", Nature Reviews Drug Discovery vol. 5(4) pp. 310-320; AOP, published online Mar. 17, 2006.

Wlad Kusnezow, et al; "Solid supports for microarray immunoassays", Journal of Molecular Recognition; vol. 16, pp. 165-176; Jul. 2003.

EKF Diagnostics; L-FABP Prognosis Biomarker in Kidney Diseases; 1 page; http://www.ekfdiagnostics.de/LFAB_ELISA_Test_Kit_938.aspx; Dec. 19, 2014.

Sung-Hyun Lee, et al; "A novel approach to ultrasensitive diagnosis using supramolecular protein nanoparticles", The FASEB Journal Research Communication; 21(7): pp. 1324-1334 Epub Feb. 5, 2007.

Jong-Hwan Lee, et al; "A Three Dimensional and Sensitive Bioassay Based on Nanostructured Quartz Combined with Viral Nanoparticles", Advanced Functional Materials, vol. 20, pp. 2004-2009; First Published: May 19, 2010.

Josh D. Nelson, et al; "An Affinity-Enhanced Neutralizing Antibody against the Membrane-Proximal External Region of Human Immunodeficiency Virus Type 1 gp41 Recognizes an Epitope between Those of 2F5 and 4E10", Journal of Virology; Apr. 2007, p. 4033-4043; vol. 81, No. 8.

John P. Nolan, et al; "Suspension array technology: evolution of the flat-array paradigm", TRENDS in Biotechnology; vol. 20, No. 1, Jan. 2002, pp. 9-12.

Jin-Seung Park, et al; "A highly sensitive and selective diagnostic assay based on virus nanoparticles", Nature nanotechnology; vol. 4, Published Online Mar. 8, 2009; pp. 259-264.

Hyuk-Seong Seo, el al; "A Three-Dimensional Nanostructured Array of Protein Nanoparticles", Advanced Functional Materials, vol. 20, pp. 4055-4061; First published: Sep. 8, 2010.

Tricia R. Serio, et al; "Nucleated Conformational Conversion and the Replication of Conformational Information by a Prion Determinant", Science, vol. 289, Aug. 25, 2000; pp. 1317-1321.

Korean Office Action dated Dec. 23, 2014; Appln. No. 10-2013-0081190.

USPTO RR dated Jan. 13, 2015 in connection with U.S. Appl. No. 13/938,575.

USPTO NFOA dated Apr. 22, 2015 in connection with U.S. Appl. No. 13/938,575.

USPTO FOA dated Jan. 12, 2016 in connection with U.S. Appl. No. 13/938,575.

* cited by examiner

| Proteinticles | Shape and size | 3D structure |
|---|---|---|
| | Number of subunits | |
| *Escherichia coli* DNA binding protein (eDPS) | Sphere, 8 nm (diameter) |  |
| | 12 | |
| Human ferritin heavy chain (hFTH) | Sphere, 12 nm (diameter) | 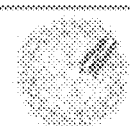 |
| | 24 | |
| Tobacco mosaic virus coat protein (TMVC) | Disk, 17 x 4 nm (diameter x thickness) |  |
| | 34 | |
| Hepatitis B virus capsid (HBVC) | Sphere, 36 nm (diameter) | 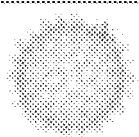 |
| | 240 | |
| *Thermoplasma acidophilum* proteasome (PTS) | Cylinder, 12 x 15 nm (diameter x height) | 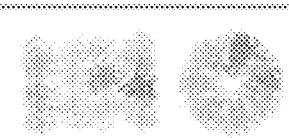 |
| | 28 | |

USE OF PROTEIN NANOPARTICLE BASED HYDROGEL

CROSS-REFERENCE TO RELATED APPLICATION

This application is a continuation-in-part of U.S. application Ser. No. 13/938,575, filed Jul. 10, 2013.

BACKGROUND

1. Field of the Invention

The present invention relates to a use of protein nanoparticle-based hydrogel capable of highly sensitive and simultaneous multi-detection of disease markers by using a hydrogel within which protein nanoparticles presenting multiple copies of disease marker detection probes are immobilized.

2. Discussion of Related Art

In protein detecting technology based on specific protein-protein interactions, for example, antigen-antibody, it is important to activate a protein probe and maintain a specific binding capacity to a target molecule. Many conventional methods for attaching proteins to solid substrate surfaces of various protein chips are carried out by simple adsorption/spread or based on immobilization through covalent bond between primary amine groups on proteins. However, typically, a protein is randomly attached to a substrate surface and a structure of the protein is easily modified, so that activity of the protein is inhibited and the protein cannot be bound to a material on the surface, resulting in low efficiency of specific binding. Further, if a protein probe is immobilized on a substrate surface by simple adsorption, the protein probe may be washed away by intensive washing conditions during a detection process, or may be transferred to another molecule having a higher affinity to the substrate surface, and particularly, it may be difficult to quantitatively control the protein probe immobilized on the substrate surface of protein chip and maintain activity of the protein probe [Kusnezow, W. Hoheisel, J. D. *J. Mol. Recognit.* 16, 165-176 (2003); Park, J. S. et al. *Nat. Nanotechnol.* 4, 259-264 (2009); Kingsmore, S. F. *Nat Rev Drug Discov.* 5(4), 310-20 (2006); Ellington, A. A., Kullo, I. J., Bailey, K. R. & Klee, G. G. *Clin. Chem.* 56(2), 186-193 (2010)].

Unlike conventional organic and inorganic nanoparticles (metal nanoparticles) which are artificially synthesized, protein nanoparticles as nanomaterials synthesized by self-assembly in a cell of a living organism can secure uniform particle size distribution and stability and can be easily mass-produced in a cell of a microorganism. Further, the protein nanoparticles can be developed to have various characteristics/functions by genetically engineered surface modification. In particular, when a disease marker detecting peptide or protein (disease marker detection probe) is represented on a surface, the protein nanoparticles can secure uniform orientation, high-density integration, and structural stability. Thus, the protein nanoparticles have been used as a material of a probe for a highly sensitive diagnostic system [Park, J. S. et al. *Nat. Nanotechnol.* 4, 259-264 (2009); Seo, H. S. et al. *Adv. Funct. Mater.* 20, 4055-4061 (2010); Lee, J. H. et al. *Adv. Funct. Mater.* 20, 2004-2009 (2010); Lee, S. H. et al. *The FASEB J.* 21, 1324-1334 (2007)].

A hydrogel has a three-dimensional porous structure and can maintain a uniform content of moisture therein, and, thus, the hydrogel has been widely used for analyzing and utilizing proteins. In particular, when the hydrogel forms a polymer through a certain coupling reaction, the hydrogel can form a covalent bond with a material having a specific residue. Thus, the hydrogel has been widely used for immobilizing a functional material. If a protein such as an enzyme is immobilized within a hydrogel, it is possible to maintain activity of the enzyme for a long time [Nolan, J. P. *TRENDS in Biotechnology.* 20, 9-12 (2002)]. However, if only a hydrogel is used as an enzyme support, the hydrogel is swollen by moisture and enzymes are spread out of the hydrogel, and thus stability over time is sharply decreased [Basri, M. et al. *J. Appl. Polym. Sci.* 82, 1404-1409 (2001)]. Therefore, technology for maintaining activity of a protein enzyme or a protein probe for a long time while immobilizing it in a moistened hydrogel is needed.

Accordingly, in the present invention, among incurable diseases, Sjögren's syndrome and acquired immune deficiency syndrome which cannot be clinically diagnosed from symptoms only are selected as model diseases, protein nanoparticle presenting multiple copies of detecting probes specific to the two diseases on a surface of the protein nanoparticle is synthesized, and a three-dimensional diagnostic sensor system having maximized surface area and stability is developed by fusing the protein nanoparticles with a three-dimensional porous hydrogel so as to construct a practical diagnostic system capable of highly sensitive and simultaneous multi-detection.

SUMMARY OF THE INVENTION

The present invention is directed to effectively detect disease markers by using protein nanoparticles presenting multiple copies of disease marker detection probes on its surface so as to control high-density integration and orientation of the detecting probes, immobilizing the protein nanoparticles to a three-dimensional porous hydrogel so as to remarkably increase a surface area to volume of a diagnostic system, and maintaining activity of the detection probes for a long time and quantitatively controlling the detection probes.

One aspect of the present invention provides a disease marker detection kit including a hydrogel within which protein nanoparticles presenting multiple copies of disease marker detection probes are immobilized.

Another aspect of the present invention provides a disease marker detection method comprising: reacting one or more hydrogels within which protein nanoparticles presenting multiple copies of disease marker detection probes are covalently immobilized, with a sample to be detected, wherein the hydrogel is formed in each well of plate having a plurality of wells to hold a sample; reacting a reaction product obtained from the above step with a reporter probe; and detecting one or more disease markers by measuring a change of absorbance or fluorescence intensity in the sample by a bound state of the disease marker-the disease marker detection probe-the reporter probe.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which:

FIG. 20 shows shape, size, number of subunit proteins, and 3D structure of five different protein nanoparticles (eDPS, hFTH, HBVC, TMVC, and tPTS) used for the surface display of $SPA_B$;

FIG. 24A-1 shows absorbance signals measured from HRP-IgG adsorbed on $SPA_B$ on protein nanoparticle, $N\text{-}eDPS\text{-}[SPA_B]_2\text{-}C$ (upper) and FIG. 24A-2 shows a re-plot of the measured absorbance signals by linearized form [C/Abs=C/Abs(sat)+$K_D$/Abs(sat), where C, Abs, Abs(sat), and $K_D$ represent the concentration of HRP-IgG, absorbance signal, saturated absorbance signal, and dissociation constant, respectively] of Langmuir adsorption isotherm equation under the assumption that the adsorption of HRP-IgG on $SPA_B$ follows Langmuir adsorption isotherm model (bottom); FIG. 24B-1 shows absorbance signals measured from HRP-IgG adsorbed on $SPA_B$ on protein nanoparticle, $N\text{-}hFTH\text{-}[SPA_B]_2\text{-}C$ (upper) and FIG. 24B-2 shows a re-plot of the measured absorbance signals by linearized form of Langmuir adsorption isotherm equation (bottom); FIG. 24C-1 shows absorbance signals measured from HRP-IgG adsorbed on $SPA_B$ on protein nanoparticle, $N\text{-}TMVC\text{-}[SPA_B]_2\text{-}C$ (upper) and FIG. 24C-2 shows a re-plot of the measured absorbance signals by linearized form of Langmuir adsorption isotherm equation (bottom); FIG. 24D-1 shows absorbance signals measured from HRP-IgG adsorbed on $SPA_B$ on protein nanoparticle, $NtPTS\alpha\text{-}[SPA_B]_2\text{-}C+N\text{-}tPTS\beta\text{-}[SPA_B]_2\text{-}C$ (upper) and FIG. 24D-2 re-plot of the measured absorbance signals by linearized form of Langmuir adsorption isotherm equation (bottom); FIG. 24E-1 shows absorbance signals measured from HRP- IgG adsorbed on SPA$_B$ on protein nanoparticle, N-HBVC-[SPA$_B$]$_2$-HBVC-C (upper) and FIG. 24E-2 shows a re-plot of the measured absorbance signals by linearized form of Langmuir adsorption isotherm equation (bottom); FIG. 24F-1 shows absorbance signals measured from HRP-IgG adsorbed on SPA$_B$ on protein nanoparticle, N-[SPA$_B$]$_2$-eDPS-[SPA$_B$]$_2$-C (upper) and FIG. 24F-2 shows a re-plot of the measured absorbance signals by linearized form of Langmuir adsorption isotherm equation (bottom); FIG. 24G-1 shows absorbance signals measured from HRP-IgG adsorbed on SPA$_B$ on protein nanoparticle, N-[SPA$_B$]$_2$-hFTH-[SPA$_B$]$_2$-C (upper) and FIG. 24G-2 shows a re-plot of the measured absorbance signals by linearized form of Langmuir adsorption isotherm equation (bottom); FIG. 24H-1 shows absorbance signals measured from HRP-IgG adsorbed on SPA$_B$ on protein nanoparticle, N-[SPA$_B$]$_2$-TMVC-[SPA$_B$]$_2$-C (upper) and FIG. 24H-2 shows are-plot of the measured absorbance signals by linearized form of Langmuir adsorption isotherm equation (bottom); and FIG. 24I-1 shows absorbance signals measured from HRP-IgG adsorbed on SPA$_B$ on protein nanoparticle, N-[SPA$_B$]$_2$-tPTSα-[SPA$_B$]$_2$-C+N-tPTSβ-[SPA$_B$]$_2$-C (upper) and FIG. 24I-2 shows a re-plot of the measured absorbance signals by linearized form of Langmuir adsorption isotherm equation (bottom). The tandem SPA$_B$, [SPA$_B$]$_2$ was genetically inserted to the surface of protein nanoparticle that is synthesized in *E. coli* through the self-assembly of engineered subunit protein;

FIG. 26A-1 shows absorbance signals measured from human HRP-IgG adsorbed on SPA$_B$ on HBVC (upper) and FIG. 26A-2 shows a re-plot of the measured absorbance signals by linearized form of Langmuir adsorption isotherm equation (bottom), and FIG. 26B-1 shows absorbance signals measured from rabbit HRP-IgG adsorbed on (SPA$_B$)$_2$, directly immobilized onto porous hydrogel without protein nanoparticles (upper) and FIG. 26B-2 shows a re-plot of the measured absorbance signals by linearized form of Langmuir adsorption isotherm equation (bottom).

DETAILED DESCRIPTION OF EXEMPLARY EMBODIMENTS

Figure 1:
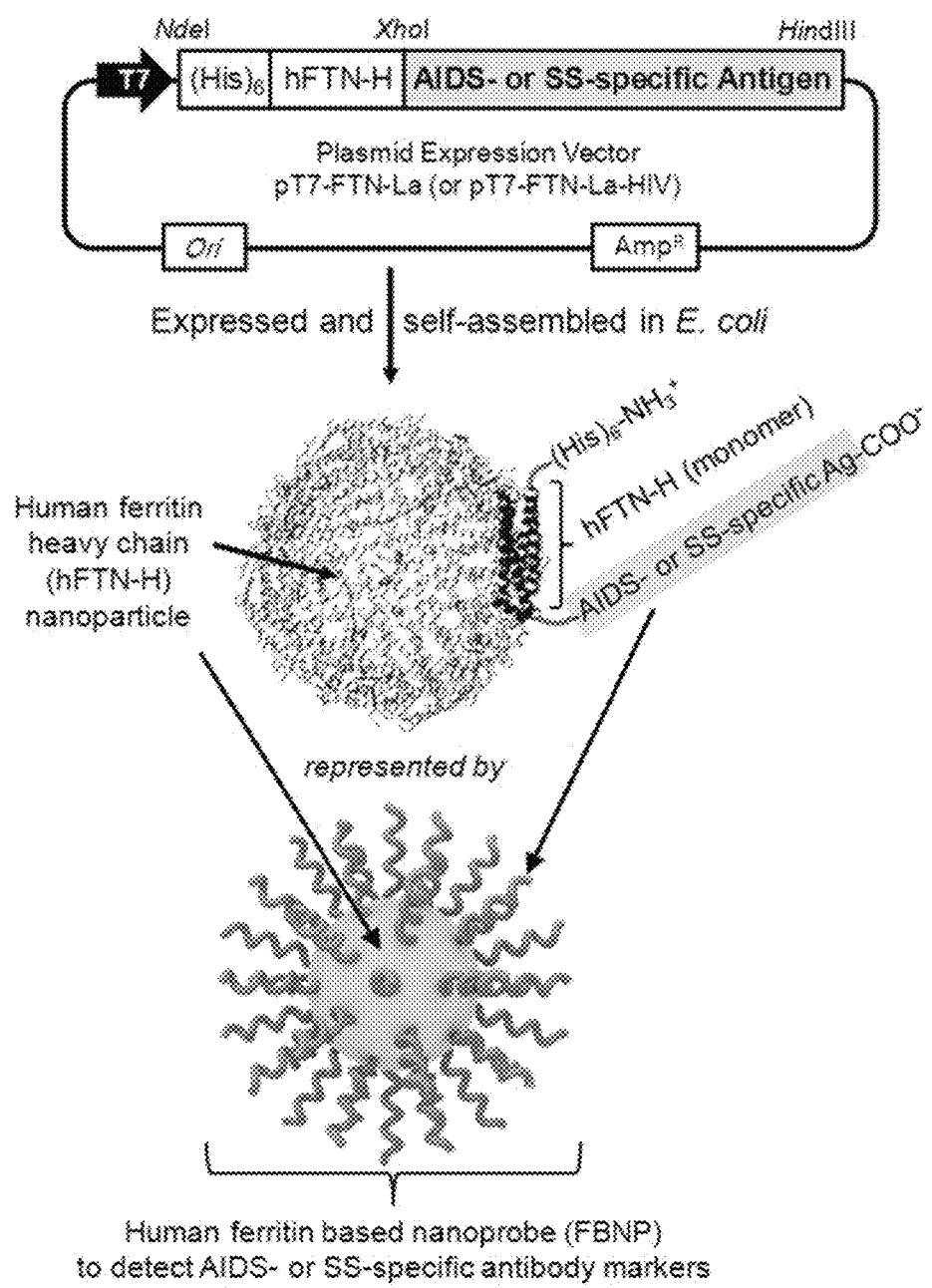
FIG. 1 is a schematic diagram of a spherical protein nanoparticle presenting multiple copies of Sjögren's autoantibody detection probes (La or Ro) or multiple copies of AIDS marker antibody detection probes (gp41 peptide) as a disease marker detection probe, and an expression vector of the protein nanoparticle.

Hereinafter, the present invention will be described in detail with reference to examples and comparative examples. However, the present invention is not limited to these examples.

Hereinafter, a configuration of the present invention will be explained in detail.

The present invention relates to a disease marker detection kit comprising a hydrogel within which protein nanoparticles presenting multiple copies of disease marker detection probes are immobilized.

In the present specification, the term "recombinant protein or fusion protein" means a protein in which another protein is linked or another amino acid sequence is added to a specific portion, i.e., an N-terminal or a C-terminal, of the protein.

The term "chimeric protein" or "protein nanoparticle probe" is used in the broadest sense to mean a protein or a protein nanoparticle to which various functions are given by bonding a foreign biomaterial to a surface of the protein nanoparticle based on genetic engineering technology or protein engineering technology. As a model scaffold for surface-presenting a disease marker detection probe, a protein capable of self-assembly including a human-derived ferritin heavy chain, a Sup35 protein derived from *Saccharomyces cerevisiae*, *Escherichia coli* DNA binding protein (eDPS) or *Thermoplasma acidophilum* proteasome (tPTS); a virus capsid protein including hepatitis B virus capsid (HBVC) or tobacco mosaic virus coat protein (TMVC); or, virus-like particles may be used for forming a chimeric protein, a protein nanoparticle, or protein nanoparticles presenting multiple copies of disease marker detection probes, but is not limited thereto. The protein nanoparticle may have a spherical shape, a rod shape, a linear shape, a disk shape, cylinder shape, or the like. If the protein nanoparticle has a spherical shape, a diameter may be in a range of, but not particularly limited to, 5 to 100 nm. The rod-shaped protein nanoparticle can also be used as a "protein nanorod".

The term "representation" or "expression" is used to represent a foreign protein on a protein nanoparticle surface such as an N-terminal (or an amino terminal) or a C-terminal (or a carboxyl terminal), and while being fused and expressed with a protein capable of self-assembly, the foreign protein can be surface-represented or expressed at the N-terminal or the C-terminal of the protein nanoparticle.

The term "expression vector" refers to a linear or a circular DNA molecule composed of a fragment encoding a target polypeptide operably linked to an additional fragment for transcription of the expression vector. The additional fragment includes a promoter and a stop codon sequence. The expression vector contains one or more replication origins, one or more selection markers, a polyadenylation signal, and the like. The expression vector is generally originated from plasmid or virus DNA or contains elements from both.

Technology for fusing a three-dimensionally structured hydrogel with protein nanoparticles presenting multiple copies of probes according to the present invention enables high integration and orientation control of a detection probe, and also enables maintenance of activity of the detection probe for a long time and quantitative control together with a significant increase in surface area to volume of a diagnostic system. That is, a protein nanoparticle-based hydrogel has a three-dimensional structure having very uniform porosity and has an excellent ability of moisture maintenance. Thus, modification of the protein nanoparticles are prevented so as to maintain activity for a long time and also uniformly distribute and quantitatively control the protein nanoparticles immobilized in the hydrogel.

The hydrogel may be formed in each well of plate having a plurality of wells to hold a sample.

According to an exemplary embodiment, when the protein nanoparticle-based hydrogel was used to detect disease markers of Sjögren's syndrome and AIDS, remarkably improved sensitivity could be shown as compared with an existing common diagnosis system. Further, when the protein nanoparticle-based hydrogel was used for an experiment with blood of a Sjögren's syndrome patient and an AIDS patient, disease markers of the two diseases were detected effectively with high stability, sensitivity and specificity.

Such results show that the protein nanoparticle-based hydrogel of the present invention can overcome technical limits (low sensitivity, specificity, reproducibility) of existing diagnosis systems and can be used as a base platform of a highly sensitive and simultaneous multi-detection nano-biosensor, and can also be used as a highly sensitive diagnosis system for blood of patients.

In a disease marker detection kit according to the present invention, a disease marker may include, but is not limited thereto, i) an antibody including autoantibody of a human autoimmune disease such as an anti-La autoantibody or an anti-Ro autoantibody of Sjögren's syndrome, or an anti-virus antibody of a viral disease such as an HIV-1 anti-gp41 antibody; or ii) an antigen protein or peptide.

The disease marker detection probe may vary depending on a kind of a disease marker and is not particularly limited. For example, the disease marker detection probe may be a protein or a peptide which can be bound to a disease marker, or an antibody specific to target antigen protein or peptide. The protein or peptide which can be bound to a disease marker may use one or two or more antigen proteins specific to autoantibodies of human autoimmune diseases, such as a human RO (SSA) protein, a human La (SSB) protein, or virus-derived antigen proteins or peptides such as an HIV-1 gp41 peptide. And, the antibody specific to antigen protein or peptide as the disease marker detection probe, may be immobilized by Staphylococcal protein A ($SPA_B$) that binds only to the Fc domain of IgG and is displayed on the protein nanoparticle surface. And then, the antibody may bind to target antigen protein or peptide.

The protein nanoparticle presenting multiple copies of the disease marker detection probes may be manufactured from expression of a chimeric gene encoding a chimeric protein fused between a protein capable of self-assembly and one or more disease marker detection probes.

An expression vector containing the chimeric protein can be introduced into a host cell so as to be transformed, and a target transformant can be selected by using an antibiotic marker.

The selected transformant can be cultured by a typical culture method and then purified, so that a protein nanoparticle of the present invention can be obtained.

The transformation may include any method of introducing a nucleic acid into an organism, a cell, a tissue, or an organ, and can be carried out by selecting standard technology appropriate for a host cell that is known in the art. The methods may include electroporation, protoplast fusion, calcium phosphate ($CaPO_4$) precipitation, calcium chloride ($CaCl_2$) precipitation, stirring using silicon carbide fibers, agrobacteria-mediated transformation, PEG, dextran sulfate, lipofectamine, etc., but are not limited thereto.

An expression amount and post-translational modifications of a protein may vary depending on a kind of a host cell, and, thus, a host cell most suitable for a purpose may be selected and used.

The host cell may include a prokaryotic host cell such as *Escherichia coli, Bacillus subtilis, Streptomyces, Pseudomonas, Proteus mirabilis,* or *Staphylococcus*, but is not limited thereto. Further, the host cell may use lower eukaryotic cells such as mycete (for example, *Aspergillus*), yeast (for example, *Pichia pastoris, Saccharomyces cerevisiae, Schizosaccharomyces, Neurospora crassa*), and cells derived from higher eukaryotes including insect cells, plant cells, mammal cells, etc.

In the protein nanoparticle-based hydrogel, the protein nanoparticle is immobilized to the hydrogel through a covalent bond, and, thus, it is possible to improve upon loss of a disease marker detection probe.

A protein nanoparticle presenting such multiple copies of disease marker detection probes can be prepared by modifying a protein nanoparticle into a chemical structure which can be co-polymerized, and then reacting it with a polymer precursor for preparing a hydrogel.

To be more specific, the protein nanoparticle can be prepared by a co-polymerization reaction between a protein nanoparticle expressed by Chemical Formula 1 below and a polymer precursor solution:

[Chemical Formula 1]

In Chemical Formula 1, X represents a protein nanoparticle, Y represents a disease marker detection probe, and R represents a vinyl group, an acryl group, or an acryl group substituted or not substituted by an alkyl having 1 to 30 carbon atoms.

The terms used for defining substituents of compounds of the present invention are as follows.

The term "alkyl" refers to a linear, branched, or cyclic saturated hydrocarbon having 1 to 30 carbon atoms, unless context dictates otherwise. A $C_{1-30}$ alkyl group may include, for example, but is not limited to, methyl, ethyl, propyl, butyl, pentyl, hexyl, heptyl, octyl, nonyl, decyl, isopropyl, isobutyl, sec-butyl and tert-butyl, isopentyl, neopentyl, isohexyl, isoheptyl, isooctyl, isononyl, and isodecyl. Further, the alkyl may include "cycloalkyl". The cycloalkyl refers to a non-aromatic saturated hydrocarbon ring having 3 to 12 carbon atoms and includes a mono ring and a fusion ring, unless context dictates otherwise. A representative example of a $C_{3-12}$ cycloalkyl may include, but is not limited to, cyclopropyl, cyclobutyl, cyclopentyl, cyclohexyl, cycloheptyl, and cyclooctyl.

In Chemical Formula 1 above, the substituent group R means a functional group which can be polymerized with a polymer, and a terminal amine group of the protein nanoparticle is substituted by the functional group so as to react with a polymer precursor for preparing a hydrogel.

Therefore, the substituent group R may represent a vinyl group, an acryl group, or an acryl group substituted or not substituted by an alkyl having 1 to 30 carbon atoms. To be more specific, the substituent group R may represent a vinyl group, an acryl group, or an acryl group substituted or not substituted by an alkyl having 1 to 6 carbon atoms. To be most specific, the substituent group R may represent a vinyl group.

According to an exemplary embodiment, an amine group represented on a surface of a protein nanoparticle reacts with N-succinimidylacrylate (NSA) so as to prepare a protein nanoparticle having a vinyl group which can be polymerized. The compound of Chemical Formula 1 refers to such a surface-modified protein nanoparticle.

The polymer may use one or two or more of polyacrylic acid, polyacrylamide, polyhydroxyethyl methacrylate, polyethyleneglycol, poly(N,N-ethylaminoethyl methacrylate), hyaluronic acid, or chitosan.

The polymer precursor solution may be prepared by adding a polymer to water or a buffer solution. As the buffer solution, PBS (Phosphate Buffered Saline) or the like may be used.

Basically, gelation of a polymer precursor solution is a polymerization process of a mixture of monomers of the polymer and can be carried out by a chemical polymerization method in which the reaction is carried out by chemical breakdown of a polymerization initiator, or a photochemical polymerization method in which the reaction is carried out by a photoinitiator such as UV or plasma.

The polymer precursor solution may further contain a polymerization initiator in an amount of 0.1 to 0.2 parts by weight with respect to 100 parts by weight of the polymer.

The polymerization initiator may use one or two or more of ammonium persulfate, tetramethylethylenediamine, riboflavin, riboflavin-5'-phosphate, 2-hydroxy-2-methylpropanon, or 2,2-diethoxyacetophenone.

A disease marker detection kit of the present invention may further include a reporter probe which can be bound to a complex of a disease marker and a disease marker detection probe.

The reporter probe is configured to detect a bound form of the disease marker and the disease marker detection probe. For example, if the disease marker is an anti-La autoantibody or an anti-Ro autoantibody of Sjögren's syndrome, or an HIV-1 anti-gp41 antibody, the disease marker detection probe may be a La, Ro, or gp41 antigen. Therefore, the reporter probe detects an antigen-antibody complex, and the reporter probe can compare an amount of the complex formed and determine existence or nonexistence of a disease marker, an amount of a disease marker, and an existence pattern, and can ultimately diagnose whether a disease has been contracted or not.

Herein, the term "antigen-antibody complex" means a combination of a proteinous disease marker and an antibody specific to the proteinous disease marker or an antibody. Typically, an amount or a formation pattern of the antigen-antibody complex formed can be measured by detecting amplitude and a pattern of a signal of a detection label connected with a secondary antibody. Such a detection label may be an enzyme, a fluorescent material, a ligand, a luminescent material, a microparticle, a redox molecule, a radioactive isotope, or the like, but is not necessarily limited thereto. If an enzyme is used as the detection label, available enzymes may include β-glucuronidase, β-D-glucosidase, β-D-galactosidase, urease, peroxidase or alkaline phosphatase, acetylcholinesterase, glucose oxidase, hexokinase and GDPase, RNase, glucose oxidase, luciferase, phosphofructokinase, phosphoenolpyruvate carboxylase, aspartate aminotransferase, and phosphenolpyruvate decarboxylase, β-latamase, etc., but are not limited thereto. If a fluorescent material is used as the detection label, the fluorescent material may include a fluorescent protein, Dylight 488 NHE-ester dye, Vybrant™ DiI, Vybrant™ DiO, a quantum dot nanoparticle, fluorescein, rhodamine, Lucifer yellow, B-phitoerithrin, 9-acridine isothiocyanate, Lucifer yellow VS, 4-acetamido-4'-isothio-cyanatostilbene-2,2'-disulfonic acid, 7-diethylamino-3-(4'-isothiocyatophenyl)-4-methylcoumarin, succinimidyl-pyrenebutyrate, 4-acetamido-4'-isothiocyanatostilbene-2,2'-disulfonic acid derivatives, LC™-Red 640, LC™-Red 705, Cy5, Cy5.5, resamine, isothiocyanate, erythrosine isothiocyanate, diethyltriamine pentaacetate, 1-dimethylaminonaphthyl-5-sulfonate, 1-anilino-8-naphthalene sulfonate, 2-sotitoluidinyl-6-naphthalene sulfonate, 3-phenyl-7-isocyanatocoumarin, 9-isothiocyanatoacridine, acridine orange 9-i(soti(2-benzoxazolyl) phenyl)maleimide sadiazol, stilbene, pyrene, derivatives thereof, fluorescent material-containing silica, semiconductor quantum dots of Groups II and IV, semiconductor quantum dots of Groups III and V, semiconductor quantum dots of Group IV, or mixtures of two or more thereof. Preferably, the fluorescent material may include one or more selected from the group consisting of a quantum dot nanoparticle, Cy3.5, Cy5, Cy5.5, Cy7, ICG (indocyanine green), Cypate, ITCC, NIR820, NIR2, IRDye78, IRDye80, IRDye82, Cresy Violet, Nile Blue, Oxazine 750, Rhodamine800, the lanthanide series, and Texas Red. If the fluorescent material is the quantum dot nanoparticle, compounds of Groups II to VI or Groups III to V may be used. In this case, the quantum dot nanoparticle may include one or more selected from the group consisting of CdSe, CdSe/ZnS, CdTe/CdS, CdTe/CdTe, ZnSe/ZnS, ZnTe/ZnSe, PbSe, PbS, InAs, InP, InGaP, InGaP/ZnS, and HgTe. If a ligand is used as the detection label, available ligands may include biotin derivatives and the like, but are not limited thereto. If a luminescent material is used as the detection label, available luminescent materials may include acridinium ester, luciferin, luciferase, etc., but are not limited thereto. If a microparticle is used as the detection label, available microparticles may include colloid gold, tinted latex, etc., but are not limited thereto. If a redox molecule is used as the detection label, available redox molecules may include ferrocene, a ruthenium complex compound, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, $[MO(CN)_8]^{4-}$, etc., but are not limited thereto. If a radioactive isotope is used as the detection label, available radioactive isotopes may include $^3H$, $^{14}C$, $^{32}P$, $^{35}S$, $^{36}Cl$, $^{51}Cr$, $^{57}Co$, $^{58}Co$, $^{59}Fe$, $^{90}Y$ $^{125}I$, $^{131}I$, or $^{186}Re$ but are not limited thereto.

For example, the reporter probe may be any one of an anti-human IgG conjugated with a reporter enzyme such as HRP (Horseradish Peroxidase) or AP (Alkaline Phosphatase); a virus antigen such as an HIV-1 gp41 peptide; a biotin-bound virus antigen such as a biotin-bound HIV-1 gp41 peptide; a human autoimmune antigen such as a biotin-bound human La (SSB) protein or Ro (SSA) protein; or an anti-protein or peptide disease marker IgG conjugated with a reporter enzyme including HRP or AP, but is not limited thereto since it may vary depending on a kind of a disease marker.

The present invention also relates to a disease marker detection method including: reacting one or more hydrogels within which protein nanoparticles presenting multiple copies of disease marker detection probes are covalently immobilized, with a sample to be detected, wherein the hydrogel is formed in each well of plate having a plurality of wells to hold a sample; reacting a reaction product obtained from the above step with a reporter probe; and detecting one or more disease markers by measuring a change of absorbance or fluorescence intensity in the sample by a bound state of the disease marker-the disease marker detection probe-the reporter probe.

In the present invention, a hydrogel within which protein nanoparticles presenting multiple copies of disease marker detection probes are bound can react with a disease marker and show a change of absorbance or fluorescence, so that one or more disease markers can be detected by measuring a change of absorbance or fluorescence intensity.

In order to detect a single disease marker or multiple disease markers, a hydrogel within which protein nanoparticles presenting multiple copies of disease marker detection probes are covalently immobilized, or one or more hydrogels within which protein nanoparticles presenting multiple copies of disease marker detection probes are covalently immobilized, may be used so as to react with a sample. The hydrogel may be formed in each well of plate having a plurality of wells to hold a sample.

The disease marker may be an autoantibody of a human autoimmune disease such as an anti-La autoantibody or an anti-Ro autoantibody of Sjögren's syndrome, or an antivirus antibody of a viral disease such as an HIV-1 anti-gp41 antibody; or an antigen protein or peptide, but is not limited thereto.

The disease marker detection probe may be a protein or a peptide which can be bound to a disease marker, or an antibody. For example, the disease marker detection probe may include, but is not particularly limited to, antigen proteins specific to autoantibodies of human autoimmune diseases such as a human RO (SSA) protein, a human La (SSB) protein, or virus-derived antigen proteins such as an HIV-1 gp41 peptide; or, an antibody specific to protein or peptide disease marker.

The protein nanoparticle presenting multiple copies of the disease marker detection probes may be prepared by the above-described method. For example, the protein nanoparticle can be prepared from any one protein capable of self-assembly among a ferritin heavy chain, a Sup35 protein derived from *Saccharomyces cerevisiae*, a virus capsid protein such as hepatitis B virus capsid (HBVC), *Escherichia coli* DNA binding protein (eDPS), tobacco mosaic virus coat protein (TMVC), or *Thermoplasma acidophilum* proteasome (tPTS) and a chimeric protein fused with one or more disease marker detection probes. In this case, the disease marker and the disease marker detection probe may be proteins or peptides.

The hydrogel within which the protein nanoparticles presenting multiple copies of the disease marker detection probes are covalently immobilized may be prepared by making a co-polymerization reaction between a protein nanoparticle and a polymer precursor solution, and a kind of the polymer and a co-polymerization method may be the same as described in the above method.

As the sample to be detected, a biological sample of a subject may be used and may include, for example, a tissue, a cell, whole blood, serum, blood plasma, saliva, cerebrospinal fluid, urine, etc.

Since the reporter probe is configured to detect a bound form of the disease marker and the disease marker detection probe, the reporter probe may be the same one as described above, but is not particularly limited thereto as long as it can be combined with the disease marker.

If the disease marker is an antibody, the disease marker detection probe may be an antigen and the reporter probe detects the antigen-antibody complex, and an amount or a pattern of the complex formed may be analyzed by, but is not limited to analysis by, western blot, ELISA (enzyme linked immunosorbent assay), radioimmunoassay, radioimmunodiffusion, an Ouchterlony technique, rocket immunoelectrophoresis, immunohistologic staining, immunoprecipitation assay, complement fixation assay, FACS, a protein chip assay, etc.

Through the above analysis methods, it is possible to compare an amount of an antigen-antibody complex formed in a biological sample of a normal person with an amount of an antigen-antibody complex formed in a biological sample of a suspected Sjögren's syndrome or AIDS patient, so that it is possible to determine existence or nonexistence of a proteinous disease marker for diagnosing Sjögren's syndrome or AIDS, an amount and a pattern thereof, and it is ultimately possible to diagnose whether or not Sjögren's syndrome or AIDS has been contracted by the suspected Sjögren's syndrome or AIDS patient in early stages.

Hereinafter, the present invention will be described in further detail with respect to examples according to the present invention and comparative examples not according to the present invention, but the scope of the present invention is not limited by the following examples.

Example 1

Manufacturing of Spherical Protein Nanoparticle-Based Hydrogel (Manufacturing Expression Vector for Synthesis of Spherical Protein Nanoparticles Presenting Disease Marker Detection Probe)

The present inventors selected Sjögren's syndrome and acquired immune deficiency syndrome (AIDS) as model diseases. It is known that these two diseases have different causes but similar symptoms. It is known that AIDS is caused by infection with human immunodeficiency virus (HIV) and serum of an AIDS patient contains various marker antibodies that recognize the HIV as an antigen. In particular, HIV-1 gp41 is an immunodominant region recognized by an antibody. It is known that most AIDS patients have an anti-gp41 antibody. A diagnosis system using a part of this antigen as a detection probe was developed. It is known that if a person is infected with HIV, his/her symptoms may escalate into symptoms (rheumatological manifestation) similar to those of an autoimmune disease patient. It is known that as for a DILS (diffuse infiltrative lymphocytosis syndrome; Sjögren-like syndrome) patient having symptoms such as xerophthalmia or xerostama, which are very similar to symptoms of Sjögren's syndrome, it is difficult to make a clinical diagnosis based on symptoms only. If Sjögren's syndrome is not treated, it can lead to life-threatening complications, such as angitis or invasion into kidneys, lungs, or the entire body. AIDS caused by infection with virus is a high-risk infectious disease, and if AIDS cannot be diagnosed in its early stages, it can be spread. Therefore, these two diseases must be distinguished and confirmed in their early stages. The biggest difference between DILS and SS is that anti-Ro and anti-La autoantibodies do not exist in serum of a DILS patient. Further, detection of anti-Ro and anti-La autoantibodies has been used during a clinical diagnosis of SS.

Based on the above description, the present inventors selected a Sjögren's syndrome autoantibody detection probe (La protein or Ro protein) or an AIDS marker antibody detection probe (gp41 peptide) as a disease marker detection probe, manufactured a production vector by inserting the Sjögren's syndrome autoantibody detection probe (La protein or Ro protein) or AIDS marker antibody detection probe (gp41) gene into a carboxyl terminal of a protein nanoparticle, and expressed the production vector in *E. coli*.

In order to do so, gene clones for coding NH$_2$-NdeI-hexahistidine-[human-derived ferritin heavy chain (SEQ ID NO:1)]-XhoI-COOH and NH$_2$-XhoI-[human-derived La protein (SEQ ID NO:2)]-HindIII-COOH(or NH$_2$-XhoI-[human-derived Ro protein (SEQ ID NO:3)]-HindIII-COOH or NH$_2$-XhoI-[human-derived La protein]-BamHI-COOH and NH$_2$-BamHI-[gp41 peptide]-[gp41 peptide]-HindIII-COOH) were PCR amplified by using an adequate primer and ligated to an NdeI-XhoI-BamHI-HindIII cloning site of pT7-7, so that an expression vector pT7-FTNH-La (or pT7-FTNH-Ro or pT7-FTNH-La-gp41-gp41) for coding synthesis of a recombinant ferritin protein nanoparticle presenting a disease marker detection probe (La or Ro or gp41) on its surface (FIG. 1) was manufactured. All manufactured plasmid expression vectors were gelated and purified, and then sequences thereof were checked by complete DNA sequencing. Further, a sequence of the gp41 peptide was used as described in Nelson J. D. et al. *J. Virol.* 81, 4033-4043 (2007).

(Manufacturing Expression Vector for Biosynthesis of Biotin Fusion Reporter Probe)

Gene clones for coding $NH_2$-NdeI-hexahistidine-[biotin peptide (SEQ ID NO:4)]-[linker $(G_3SG_3TG_3SG_3)$]-[human-derived La protein]-HindIII-COOH (or $NH_2$-NdeI-hexahistidine-[N-ePGK (N-terminal domain of *E. coli* phosphoglycerate kinase)]-[biotin peptide]-[linker $(G_3SG_3TG_3SG_3)$]-[human-derived Ro protein]-HindIII-COOH fused with N-ePGK (SEQ ID NO: 5) as a fusion tag developed by the present inventors for water-soluble expression of a Ro protein, if alone, showing insoluble expression in *E. coli*) were PCR amplified by using an adequate primer and ligated to an NdeI-HindIII cloning site of pT7-7, so that an expression vector pT7-biotin-La (or pT7-NePGK-biotin-Ro) for coding a biotin fusion reporter probe (La or Ro or gp41) was manufactured. All manufactured plasmid expression vectors were gelated and purified, and then sequences thereof were checked by complete DNA sequencing.

(Manufacturing and Expression of Transformant for Biosynthesis of Protein Nanoparticles Presenting Disease Marker Detection Probe and Reporter Probe)

The vectors manufactured above by a method described by Hanahan (Hanahan D, *DNA Cloning* vol. 1 109-135, IRS press 1985) were transformed in *E. coli*.

To be specific, the vectors manufactured above were transformed by a thermal shock method in *E. coli* BL21 (DE3) treated with $CaCl_2$ and then cultured in a culture medium containing ampicillin, so that a colony which was transformed from the expression vector and had ampicillin resistance was sorted. A part of a seed culture solution obtained by culturing the colony in a LB culture medium for overnight was introduced into a LB culture medium containing 100 mg/mL ampicillin and then cultured at 37° C. at 130 rpm. When $OD_{600}$ of the culture solution reached 0.7 to 0.8, IPTG (0.5 mM) was added and a temperature was lowered to 20° C. so as to induce an expression of a recombinant gene. After the IPTG was added, the culture solution was additionally cultured for 16 to 18 hours under the same conditions. As for a reporter probe fused with a biotin peptide at an amino terminal, when the IPTG was added, 10 μg/mL of biotin was added to the culture medium so as to be cultured.

(Purification of Protein Nanoparticles Presenting Disease Marker Detection Probe and Reporter Probe)

In order to purify a recombinant protein, the *E. coli* cultured above was collected and its cell pellets were re-suspended in 5 mL of a lysis buffer [pH 8.0, 1 mM PMSF (phenylmethylsulfonyl fluoride: serine proteinase inhibitor), 10% glycerol, 0.1% Triton X-100, 2 mM $MgCl_2$, 50 mM Tris-Cl, 0.1 mg/mL lysozyme] and stirred at normal temperature for 15 to 30 minutes and then disrupted by using a sonicator. A cytosol of the disrupted cells was centrifuged at 13,000 rpm for 10 minutes so as to separate a supernatant. Then, each recombinant protein was separated by using a $Ni^{2+}$-NTA column (Qiagen, Hilden, Germany) (washing buffer: pH 8.0, 50 mM sodium phosphate, 300 mM NaCl, 80 mM imidazole; elution buffer: pH 8.0, 50 mM sodium phosphate, 300 mM NaCl, 250 mM imidazole). In order to remove the imidazole from the elution buffer, the buffer was substituted by a PBS buffer by using a membrane filterator (Amicon, 10K).

Figure 2A:
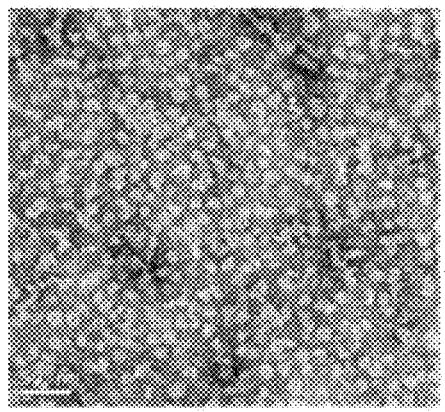
FIG. 2A shows a TEM image of protein nanoparticles presenting multiple copies of Ro proteins as a Sjögren's autoantibody detection probe.
Figure 2B:
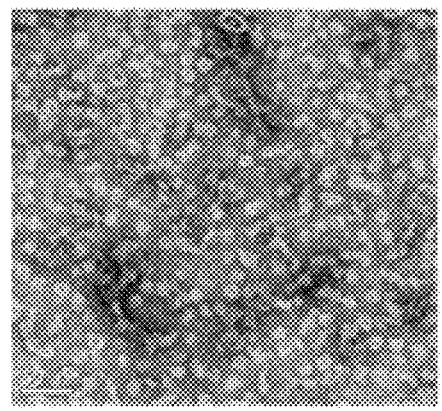
FIG. 2B shows a TEM image of protein nanoparticles presenting multiple copies of La proteins as a Sjögren's autoantibody detection probe.
Figure 2C:
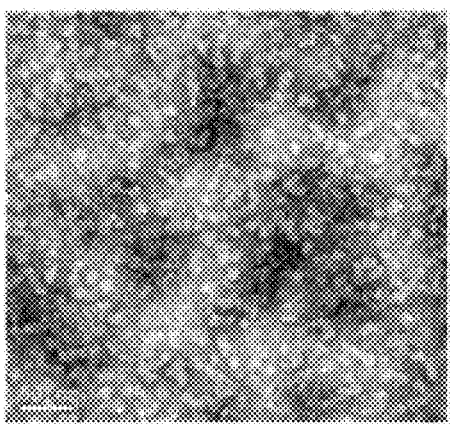
FIG. 2C shows a TEM image of protein nanoparticles presenting multiple copies of La proteins as a Sjögren's autoantibody detection probe and multiple copies of AIDS marker antibody detection probes (gp41 peptide)

It was confirmed from TEM images of FIG. 2A to 2C that uniform spherical nanoparticles were formed.

(Manufacturing Fluorescent Material-Labeled Reporter Probe)

A fluorescent material (quantum dot) as a label was bound to the biotin fused reporter probe. To manufacture a final fluorescent reporter probe, the quantum dot having a surface to which streptavidin was immobilized and the reporter probe fused with biotin at an amino terminal were bound to each other through a biotin-streptavidin bond.

A Ro protein or a La protein (0.05 pmol) fused with biotin at an amino terminal and Quantum dot 565 (5 pmol) having a surface to which streptavidin was immobilized were cultured in a PBS buffer at 25° C. for 2 hours so as to be bound to each other. Then, a reporter probe which was not labeled with the quantum dot was removed by streptavidin affinity chromatography and ultrafiltration (Amicon Ultra 100K).

Since a length of a peptide was too short, a reporter probe (biotin: gp41) for detecting AIDS was manufactured by peptide synthesis and then bound to Quantum dot 800 by the same method as described above.

(Manufacturing Hydrogel within which Protein Nanoparticles are Immobilized)

10 mg of the protein nanoparticles manufactured above and 0.01 mg of N-succinimidylacrylate (NSA) were incubated in a PBS buffer at 37° C. for 1 hour and bound to each other. Then, non-bound NSA was removed by ultrafiltration (Amicon Ultra 100K), so that protein nanoparticles having a polymerizable chemical structure were finally manufactured.

According to the records, a polyacrylamide fusion hydrogel has advantages of high stability, low non-specific bonding, low fluorescent background, and the like.

Figure 3A:
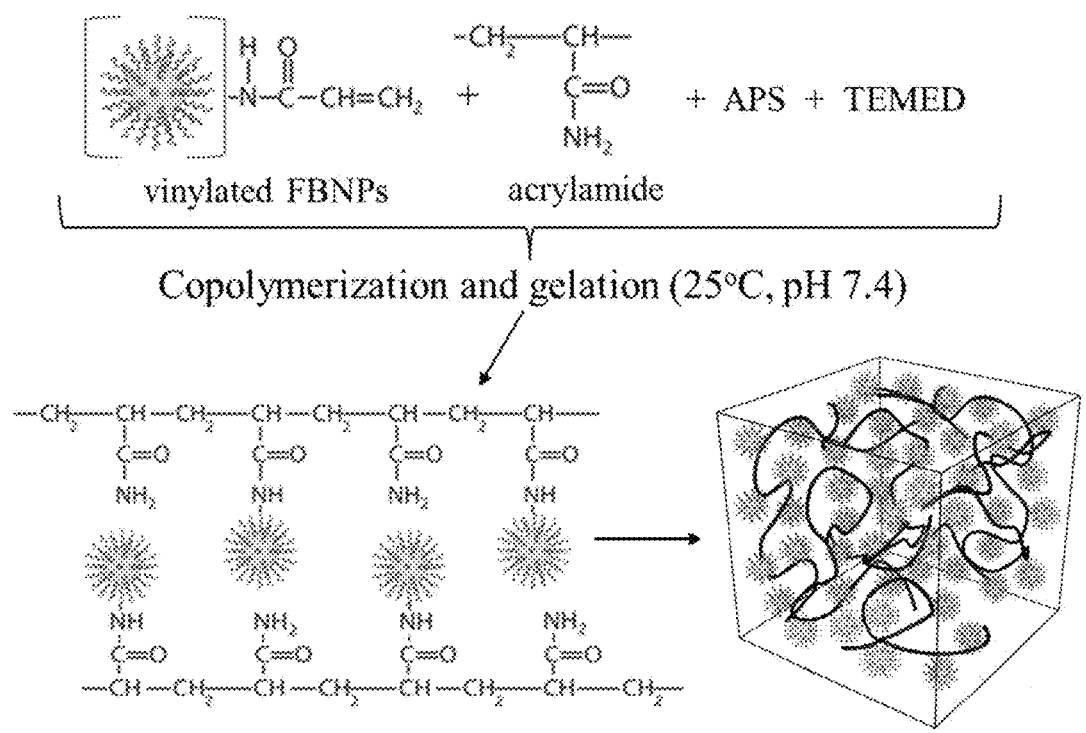
FIG. 3A provides a schematic diagram showing a manufacturing process of a spherical protein nanoparticle-based hydrogel.

Therefore, 30 μg of the modified protein nanoparticles and 0.9% polyacrylamide (29:1 W/W acrylamide:bis-acrylamide) were mixed in the presence of 0.125% w/v ammonium persulfate (APS) and 0.125% w/v tetramethylethylenediamine (TEMED) and each 50 μl of the mixture was apportioned into a 96-well plate and polymerized at 25° C. for 16 hours, so that protein nanoparticle-based hydrogel was manufactured (FIG. 3A).

Figure 3B:
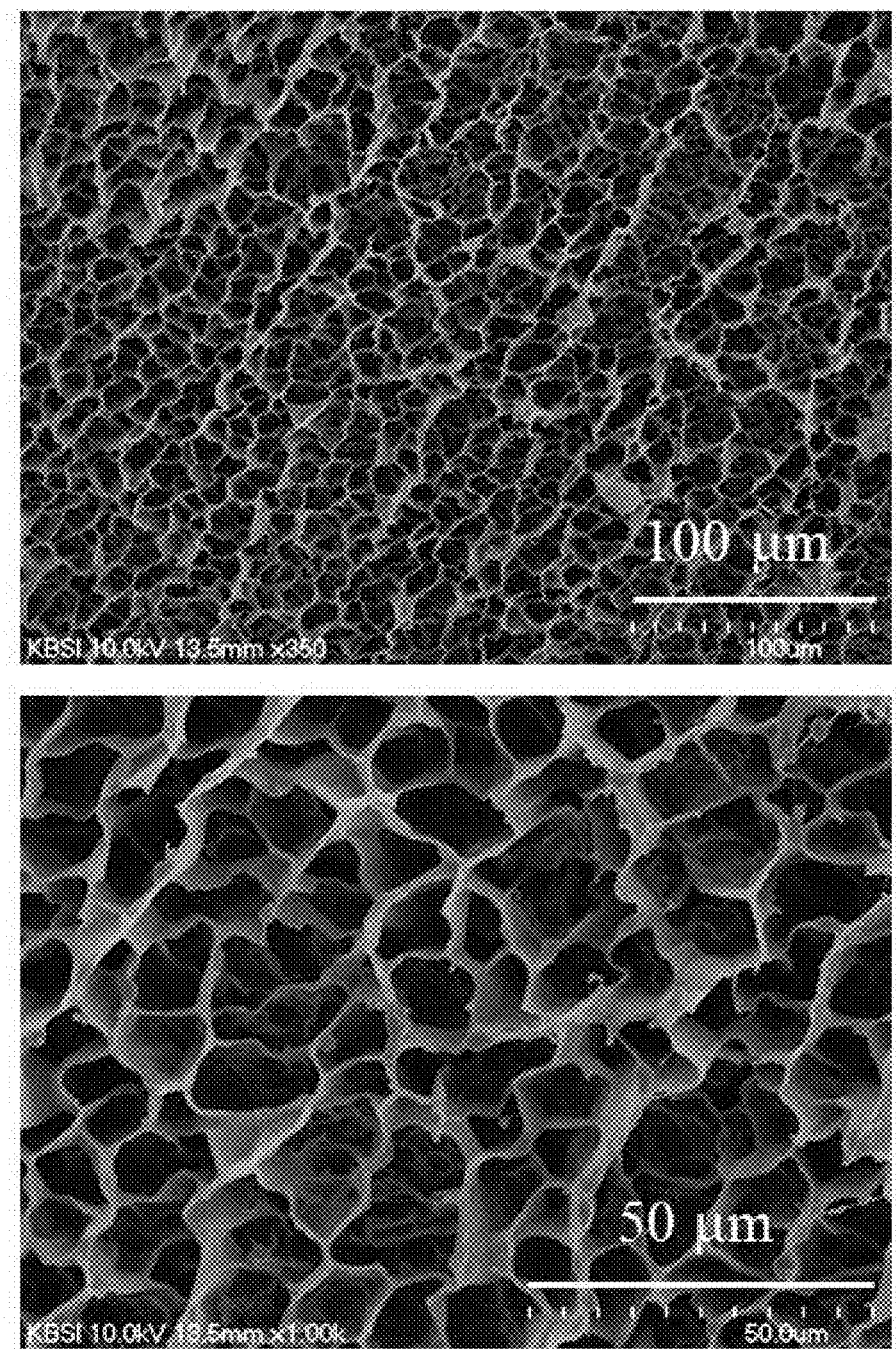
FIG. 3B shows a SEM image of a manufactured protein nanoparticle-hydrogel complex.

As a result, it was confirmed from SEM images that the protein nanoparticle-based hydrogel had a three-dimensional structure having very uniform porosity (FIG. 3B).

Further, an amount of detection probes immobilized to a substrate is a key factor for determining sensitivity of a detection system. Thus, in order to construct a highly reliable diagnosis system, technology for uniformly immobilizing detection probes of high density is demanded. Typically, if detection probes are simply adsorbed and immobilized to a two-dimensional surface of a substrate, it is difficult to quantitatively control an actual amount of detection probes immobilized to the substrate. However, as for protein nanoparticle-based hydrogel, it is possible to control an amount of protein nanoparticles during a manufacturing process and also possible to quantitatively measure an accurate amount of detection probes present on a substrate since the protein nanoparticles are fused and immobilized to the hydrogel.

Therefore, in order to check whether the protein nanoparticles were uniformly dispersed and immobilized to the hydrogel, the protein nanoparticle-based hydrogel presenting biotin was reacted with an anti-biotin antibody bound to gold nanoparticles (20 nm) and then the gold nanoparticles were amplified by using a silver enhancement kit.

Figure 3C:
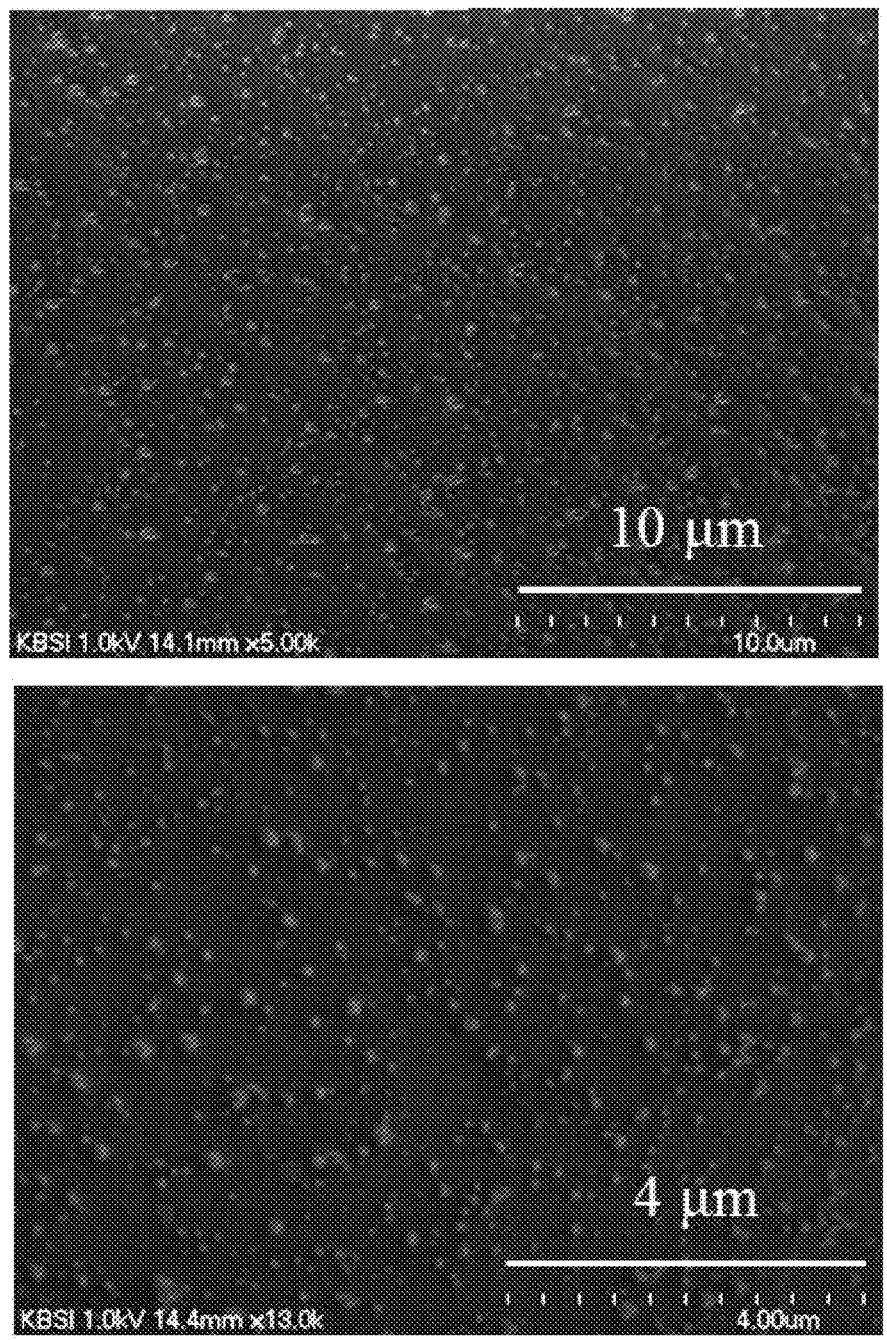
FIG. 3C shows a SEM image of distribution of protein nanoparticles immobilized to the hydrogel.

When SEM images were captured, positions of the protein nanoparticles in the hydrogel could be clearly confirmed through the gold nanoparticles. As shown in FIG. 3C, it was confirmed that the gold nanoparticles were uniformly dispersed in the hydrogel, which showed that the protein nanoparticles were uniformly dispersed and immobilized throughout the whole area of the hydrogel.

In order to commercialize a disease diagnosis system, it is necessary to maintain stability of a protein detection probe immobilized to a substrate for a long time. Typically, a protein immobilized to a two-dimensional surface is likely to be exposed to air and cannot maintain moisture if it is not treated with a stabilizer, and, thus, it is difficult to preserve the protein for a long time.

In order to verify a protein preservation ability of the protein nanoparticle-based hydrogel constructed by the present inventors, an enhanced green fluorescent protein (eGFP) and protein nanoparticles were fused and expressed and immobilized to each of a two-dimensional polystyrene (PS) surface and a three-dimensional hydrogel-based structure widely used as protein immobilizing substrates. After being filled with nitrogen, they were kept at 25° C., and changes of fluorescence intensity over time were compared.

Figure 4A:
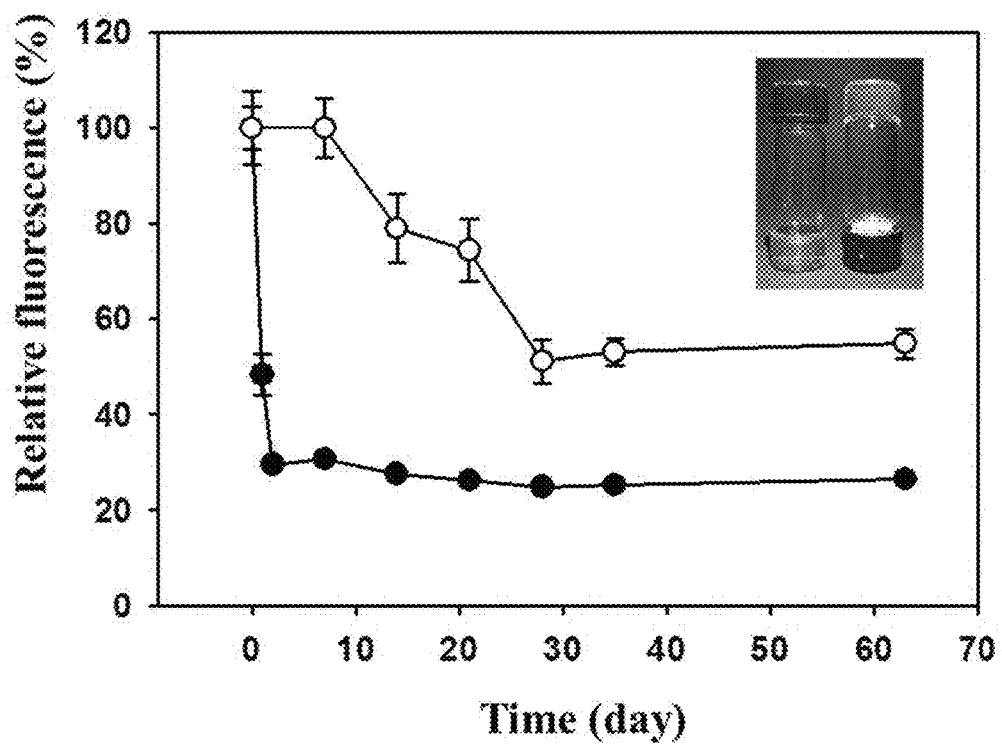
FIG. 4A provides a graph showing a change of fluorescence intensity of the fluorescent protein nanoparticle over time.
Figure 4B:
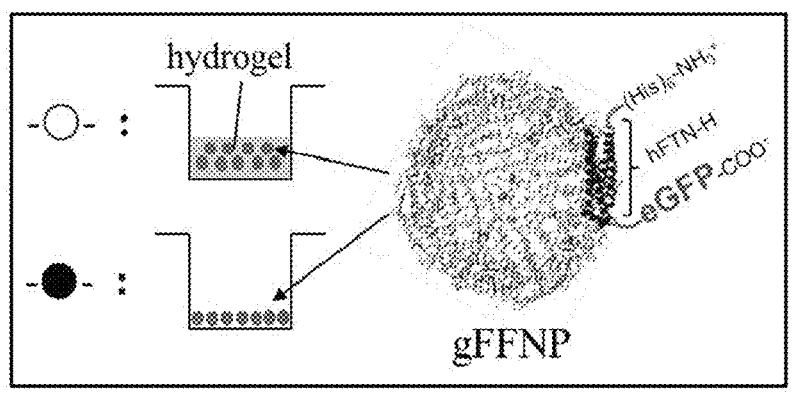
FIG. 4B is schematic diagram showing a spherical fluorescent protein nanoparticle immobilized to a two-dimensional substrate and a three-dimensional hydrogel.

As a result, fluorescence intensity of the fluorescent nanoparticles immobilized to the two-dimensional polystyrene surface decreased to 30% of initial fluorescence intensity after one day, whereas fluorescence intensity of the fluorescent nanoparticles fused and immobilized to the hydrogel only decreased to 50% of the initial fluorescent intensity after an entire month. It is deemed that since the hydrogel has an excellent ability of moisture maintenance as compared with the two-dimensional surface, denaturation of the protein was minimized. This shows that the hydrogel has a great advantage as a detection probe immobilization platform of a practicable diagnosis system to be constructed in the future (FIG. 4).

(Sensitivity Examination of Protein Nanoparticle-Immobilized Hydrogel Fusion Material)

Figure 5:
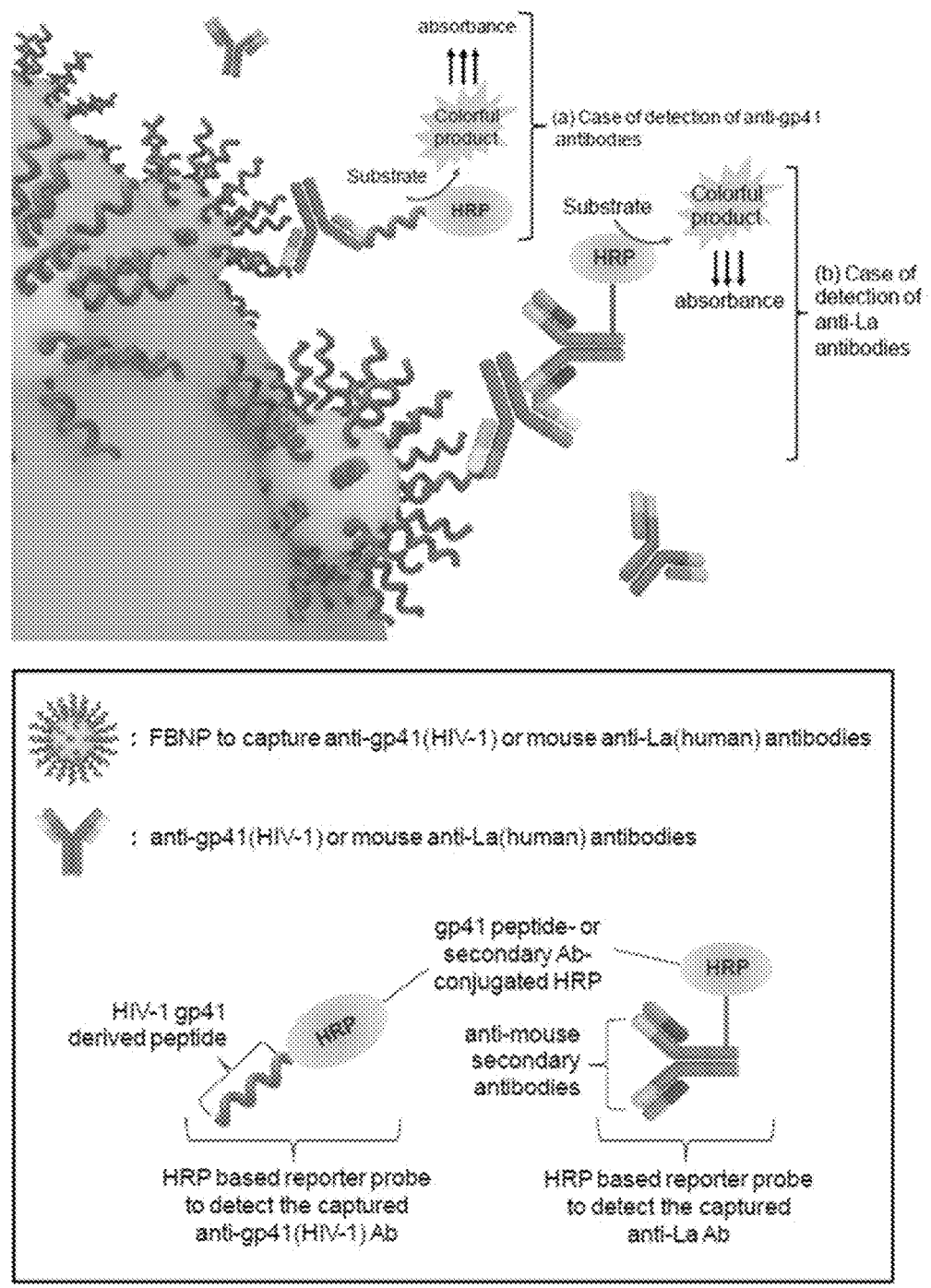
FIG. 5 is a schematic diagram of a target antibody detection system using a spherical protein nanoparticle-based hydrogel for diagnosing AIDS and Sjögren's syndrome.

In order to evaluate the utility and performance of the three-dimensional protein nanoparticle-based hydrogel diagnosis system manufactured above, sensitivity analysis was carried out. The sensitivity analysis was carried out by using anti-gp41 and anti-La antibodies. As shown in FIG. 5, each hydrogel fused with protein nanoparticles presenting multiple copies of detection probes was reacted with a sample (an anti-gp41 or anti-La antibody or a patient blood sample), and then absorbance thereof was measured by using a secondary antibody bound to a HRP.

Further, the results were compared and analyzed with a typically commercialized ELISA (Enzyme-linked Immunosorbent Assay) kit for blood diagnosis and a diagnosis system in which protein nanoparticles are immobilized to a two-dimensional polystyrene (PS) surface.

In order to do so, the hydrogel containing protein nanoparticles ((($FTNH-La-(gp41)_2$])) manufactured above was washed by using a PBS buffer, and a PBS buffer containing 100 µl of human serum (serum of Sjögren's syndrome patient or healthy serum) or a mouse anti-La antibody or a human anti-gp41 antibody was added and cultured at normal temperature for 2 hours with stirring. After the hydrogel was washed by using the PBS buffer, 100 µl of "enzyme conjugate reagent [anti-mouse IgG or gp41 peptide conjugated with a HRP enzyme ("enzyme conjugate reagent" was used for comparison with the ELISA kit)]" was added to each well and cultured at normal temperature for 1 hour with stirring and then washed with the PBS buffer. 100 µl of "TMB reagent (containing a substrate to the HRP enzyme)" was added to each well and cultured at normal temperature for 15 minutes and 100 µl of 1M sulfuric acid was added to each well and mixed for 30 sec to stop an enzyme reaction, and then absorbance thereof was measured at 450 nm by using a microplate reader.

Figure 6A:
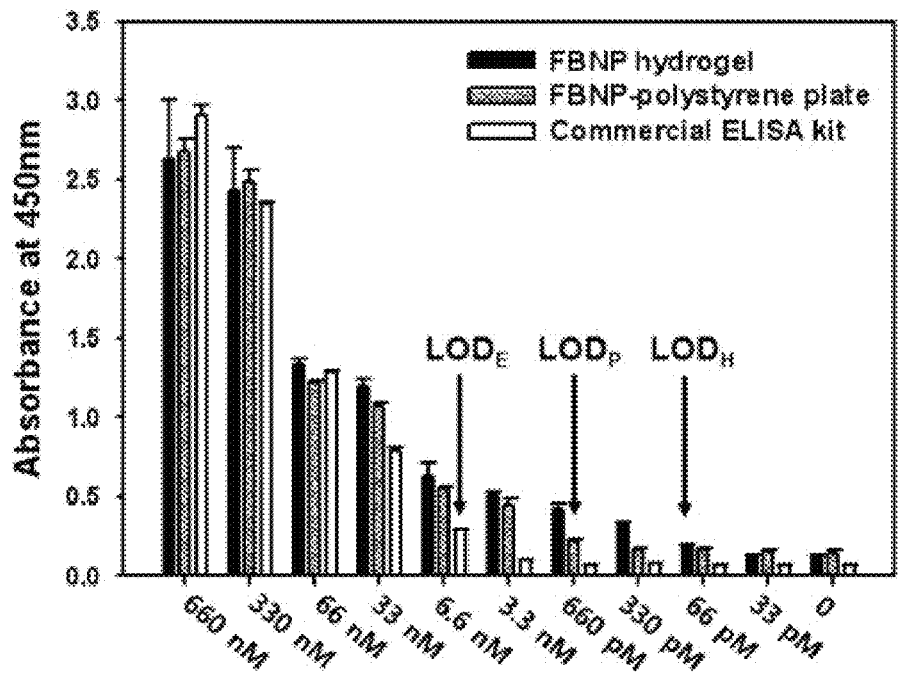
FIG. 6A shows La autoantibody detection sensitivity verification results using a spherical protein nanoparticle-based hydrogel simultaneously presenting multiple copies of La proteins for diagnosing Sjögren's syndrome.
Figure 6B:
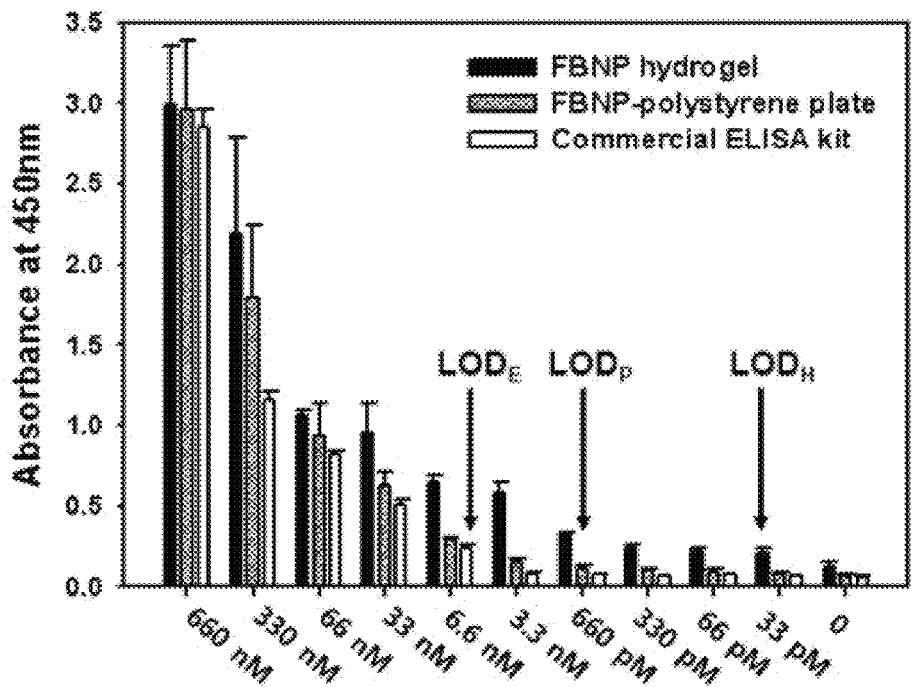
FIG. 6B shows AIDS target antibody sensitivity verification results using a spherical protein nanoparticle-based hydrogel simultaneously presenting multiple copies of gp41 peptides for diagnosing AIDS.

As a result, the two-dimensional ELISA kit showed that the anti-La antibody and the anti-gp41 antibody had LODs [limit of detection: determined as defined by IUPAC (International Union of Pure and Applied Chemistry)] of 6.6 nM as an antibody concentration, whereas the protein nanoparticle-based hydrogel showed that the anti-La antibody and the anti-gp41 antibody had LODs (limit of detection) of 66 pM and 33 pM, respectively, as an antibody concentration (FIGS. 6A and 6B). That is, the protein nanoparticle-based hydrogel showed sensitivity 100 to 200 times higher than the two-dimensional ELISA kit, which showed the excellence of the protein nanoparticle-based hydrogel.

Figure 7A:
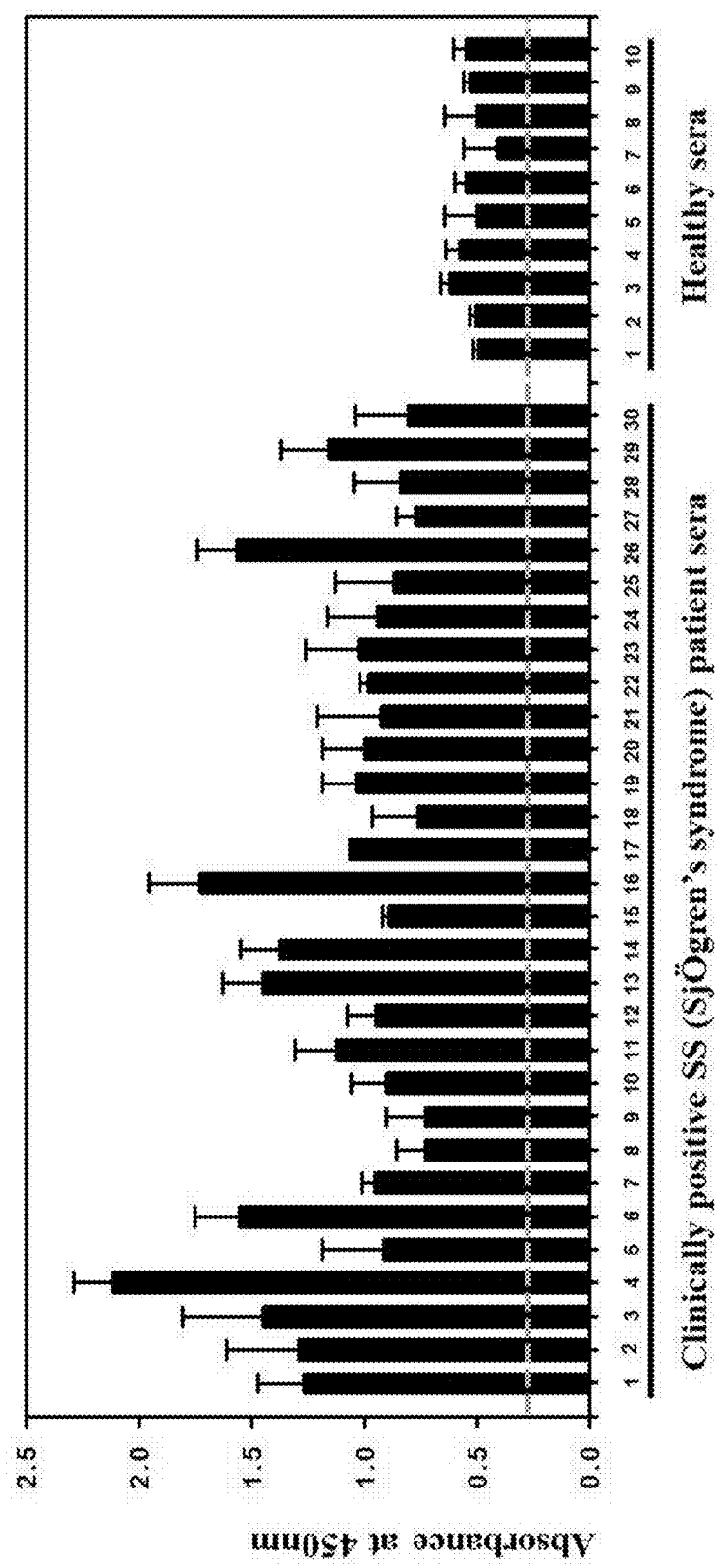
FIG. 7A shows sensitivity verification results of a spherical protein nanoparticle-based hydrogel at the time of diagnosis of Sjögren's syndrome.
Figure 7B:
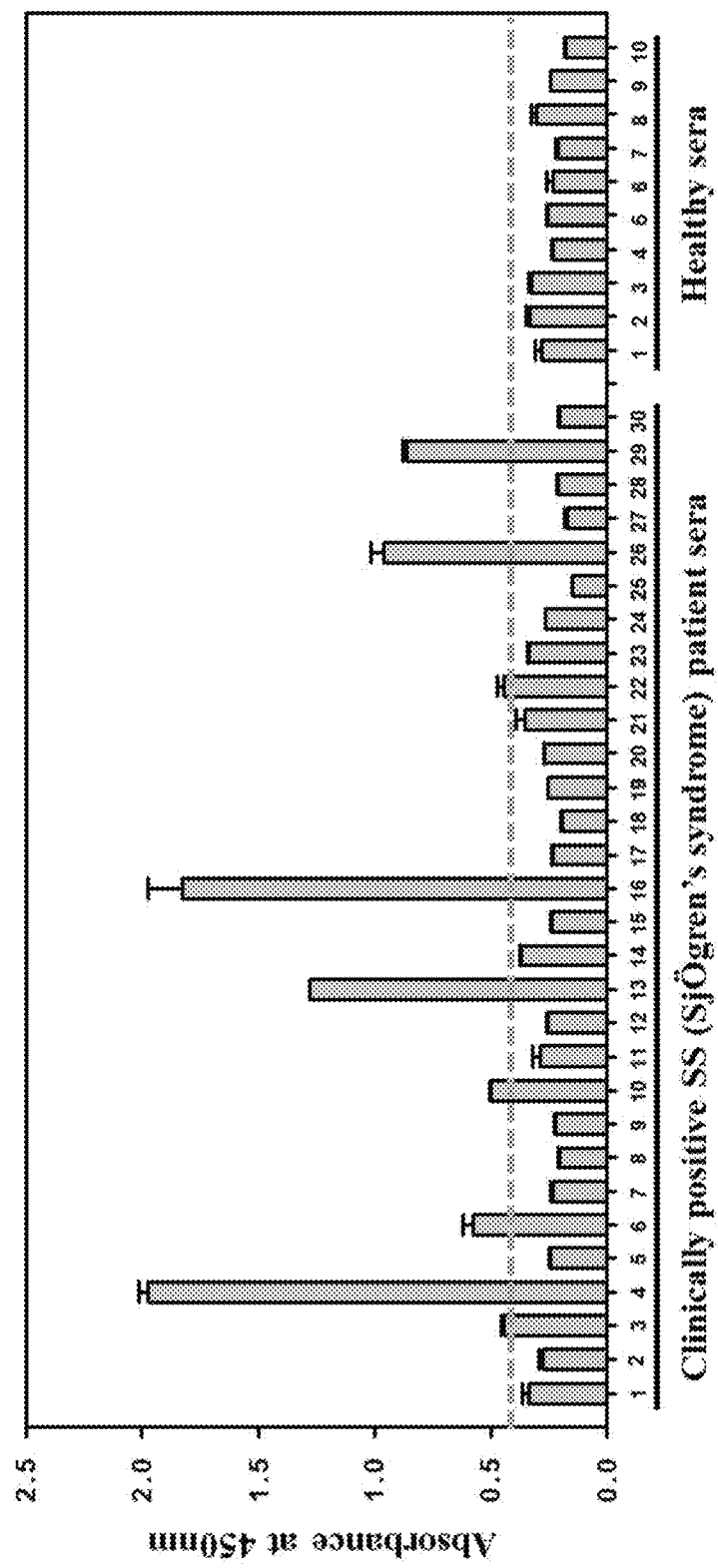
FIG. 7B shows sensitivity comparison experiment results of a commercial ELISA kit at the time of diagnosis of Sjögren's syndrome.

Further, as a result of a comparative experiment with a commercialized ELISA kit for blood diagnosis by using blood samples of Sjögren's syndrome patients, the ELISA kit detected an anti-La antibody from only nine out of thirty patients, resulting in a sensitivity of 30%, whereas the protein nanoparticle-based hydrogel diagnosis system constructed by the present inventors detected an anti-La antibody from twenty six patients, resulting in remarkably high sensitivity of 87% (FIG. 7A to 7B). It is deemed that since the protein nanoparticle of the present invention is immobilized to the three-dimensional porous hydrogel, it is present in a liquid phase-like condition rather than a solid phase-like condition, which prevents denaturation of the samples and allows easy accessibility, and which shows that the hydrogel has a great advantage as a probe immobilization platform of a diagnosis system.

(Simultaneous Multi-Detection of Disease Using Protein Nanoparticle-Immobilized Hydrogel Fusion Material)

A simultaneous multi-detection system is advantageous in that various diseases can be diagnosed at the same time through one analysis, which is time and cost effective, and diseases can be diagnosed from a small blood sample. However, the simultaneous multi-detection system has drawbacks of low reproducibility and non-specific cross-reactivity which need to be solved.

Figure 8:
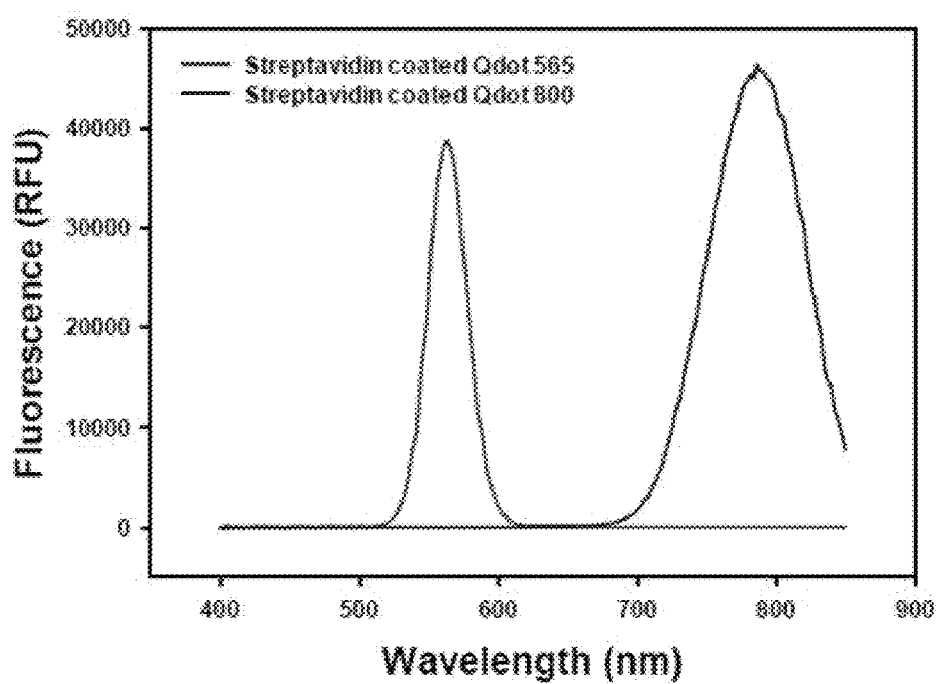
FIG. 8 shows emission wavelength measurement results (excitation wavelength: 350 nm) of quantum dots selected to be applied to a simultaneous multi-detection system.
Figure 9:
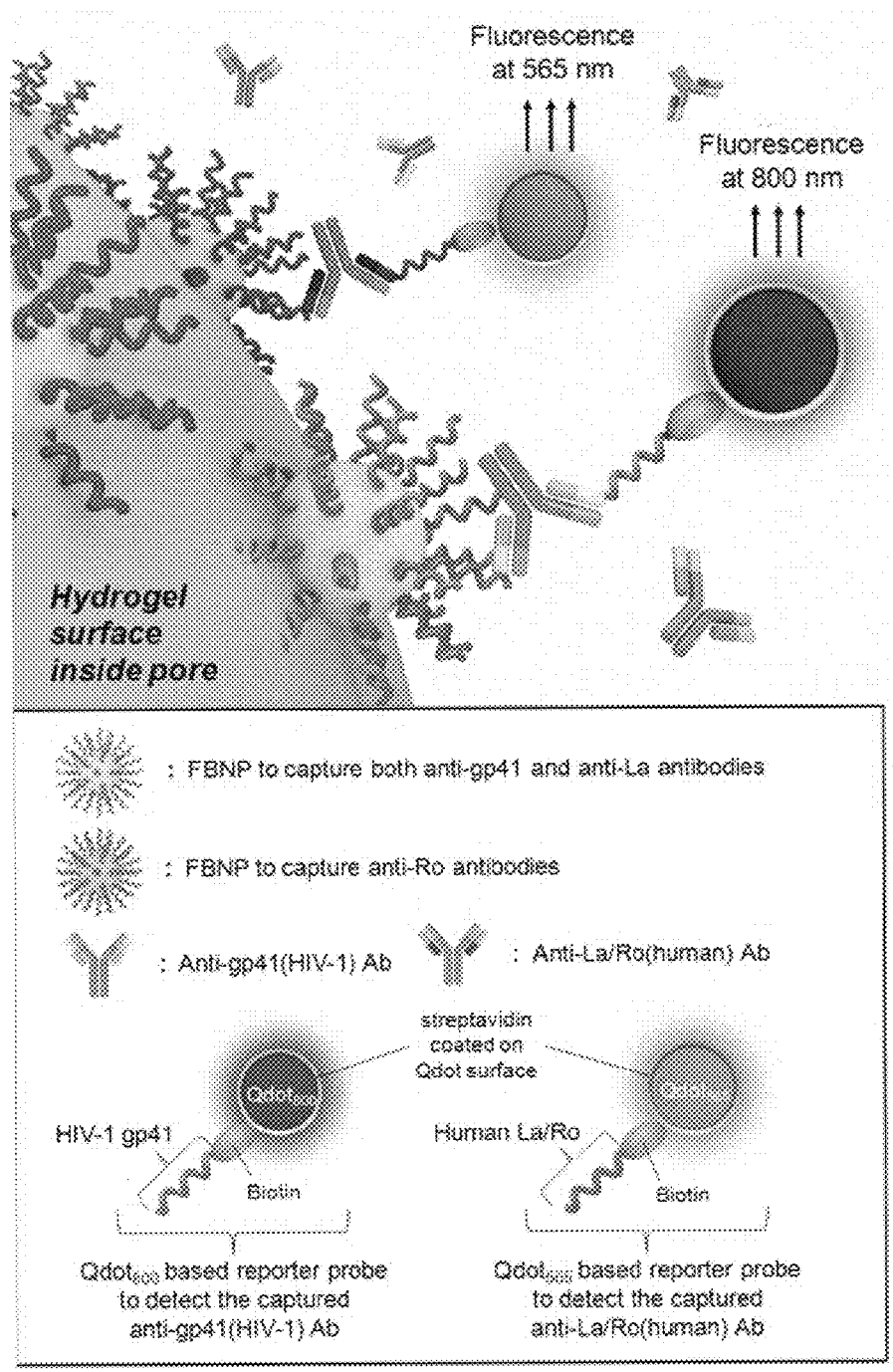
FIG. 9 is a schematic diagram of simultaneous multi-detection of AIDS and Sjögren's syndrome by using a spherical protein nanoparticle-based hydrogel.

In order to construct a simultaneous multi-detection system for two diseases, the present inventors manufactured a hydrogel by mixing protein nanoparticles containing both a gp41 peptide and a La protein with protein nanoparticles containing a Ro protein as described above, and immobilized a biotin fused La protein or Ro protein to Quantum dot 800-streptavidin as a fluorescent material and immobilized a biotin fused gp41 peptide to quantum dot 585-streptavidin so as to be used as reporter probes for simultaneous detection (Quantum dot 800 and Quantum dot 585 have excitation wavelengths and emission wavelengths which do not overlap with each other, and, thus, they can be used at the same time; see FIG. 8). An experiment was carried out as shown in FIG. 9, and a blood sample of a Sjögren's syndrome patient and a blood sample of an HIV-1 positive patient were mixed and used as shown in FIG. 9.

Figure 10A:
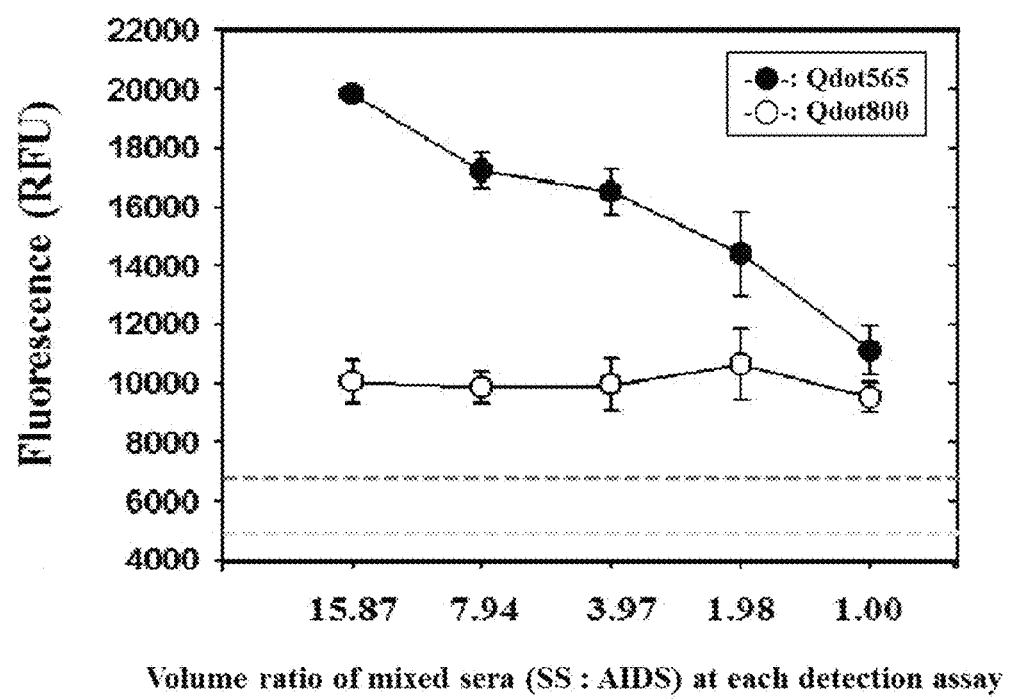
FIG. 10A to 10F show results of application of AIDS and Sjögren's syndrome patient samples at the time of simultaneous multi-detection of AIDS and Sjögren's syndrome by using a spherical protein nanoparticle-based hydrogel.
Figure 10B:
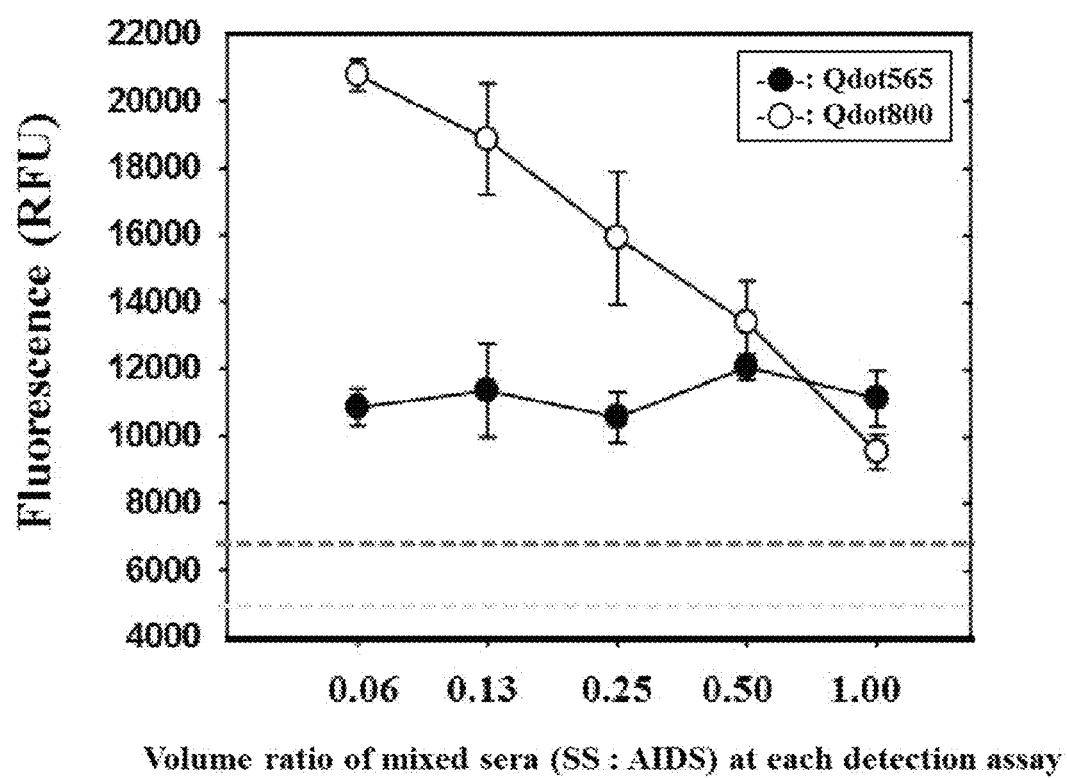
Figure 10C:
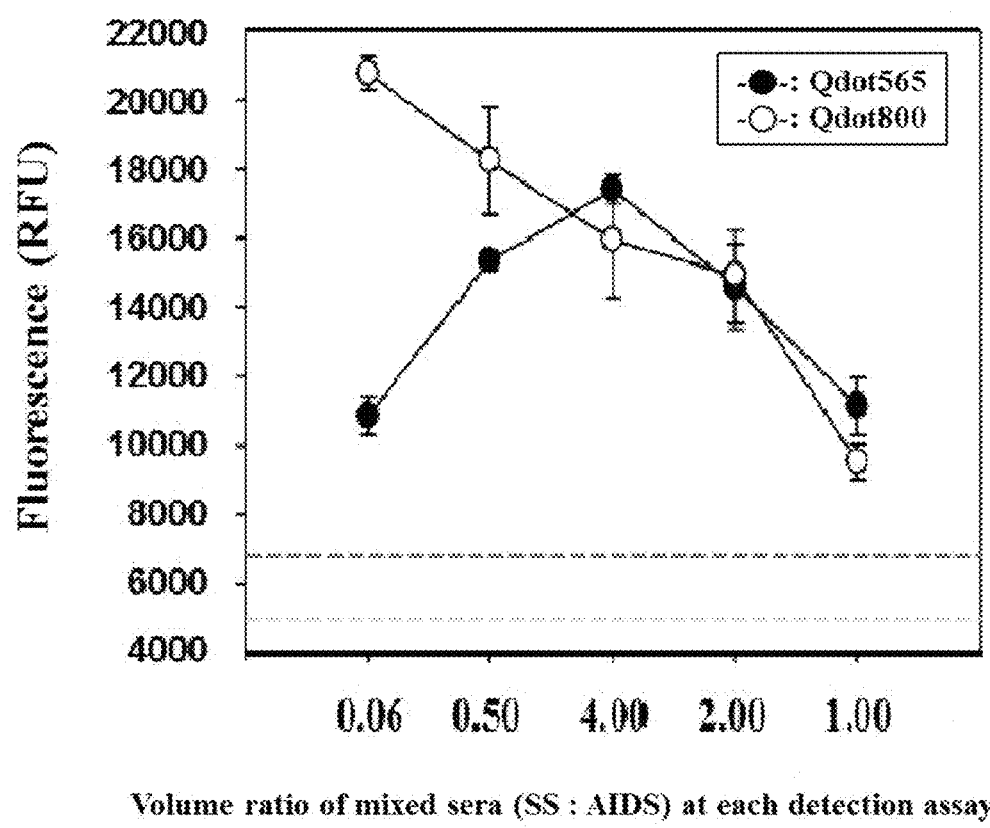
Figure 10D:
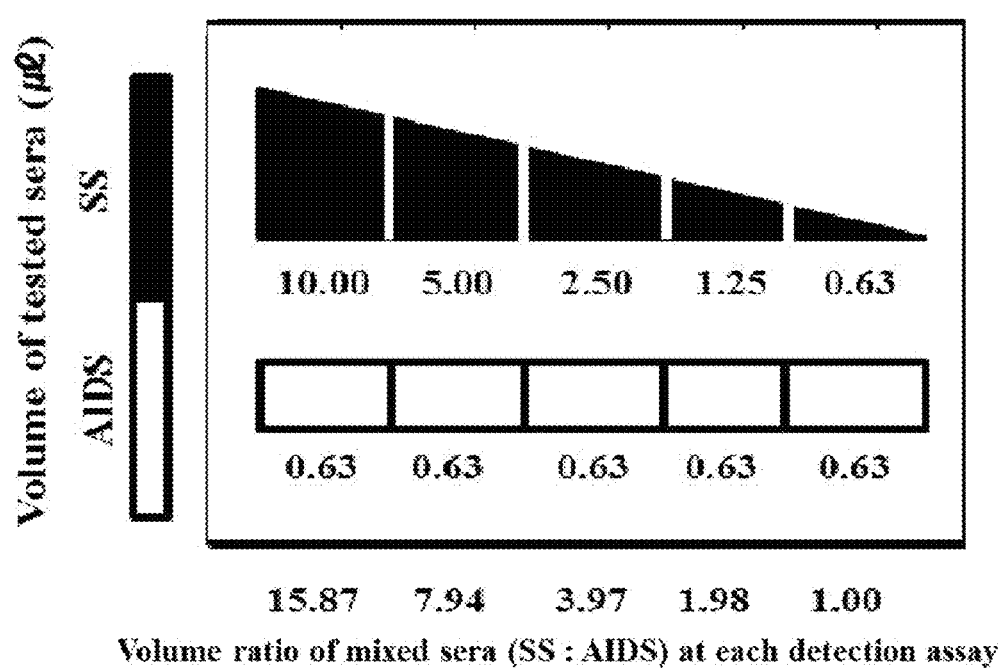
Figure 10E:
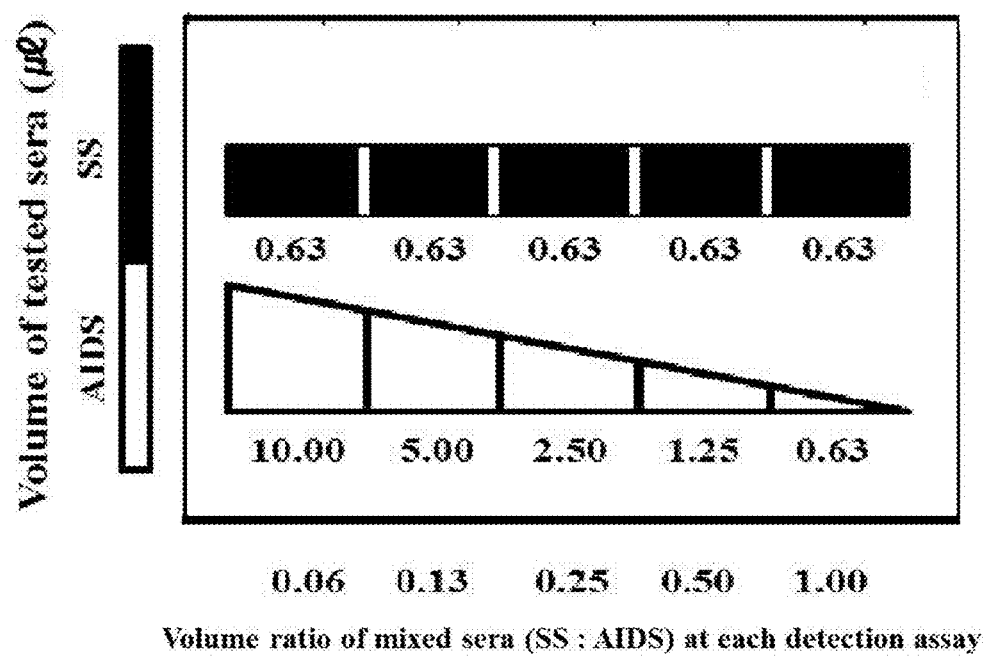
Figure 10F:
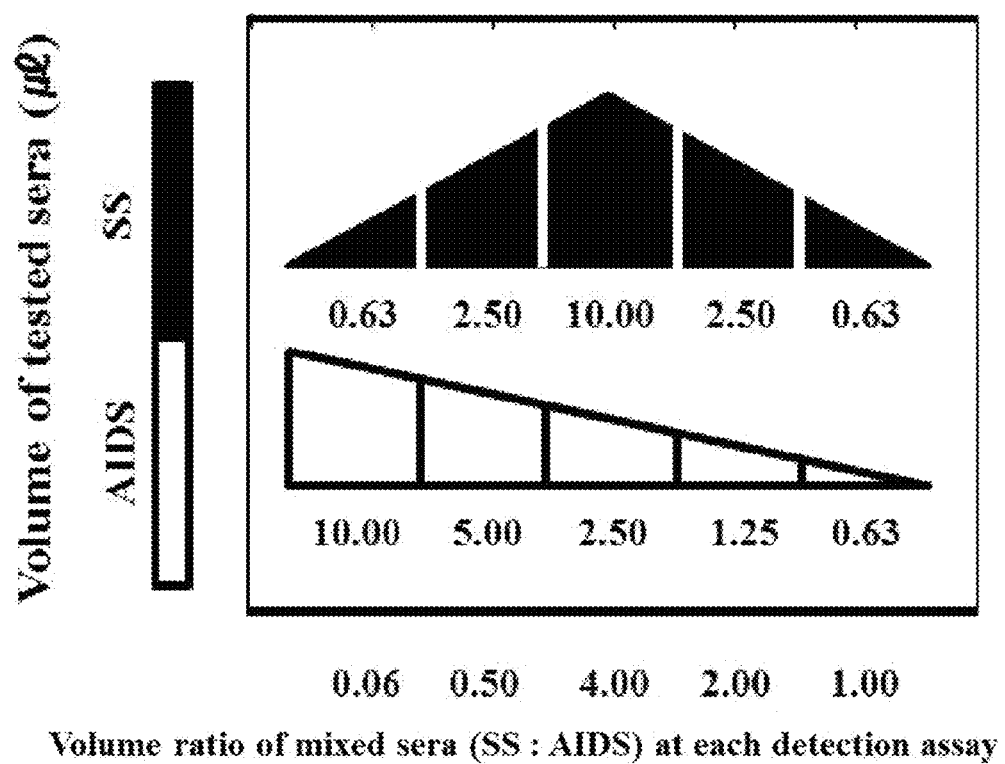

To be more specific, the manufactured hydrogel containing 15 µg of [FTNH-La-(gp41)$_2$] and 15 µg of [FTNH-Ro] as protein nanoparticles was washed by using a PBS buffer, and 100 µl of a serum mixed solution in which a serum sample of the Sjögren's syndrome patient and the blood sample of the HIV-1 positive patient were mixed as shown in FIGS. 10D to 10F was added and cultured at normal temperature for 2 hours with stirring. After the hydrogel was washed by using the PBS buffer, 100 μl of the fluorescent reporter probe manufactured above was added to each well and cultured at normal temperature for 1 hour with stirring and then washed with the PBS buffer. Thereafter, fluorescence intensity thereof was measured at an excitation wavelength of 350 nm and an emission wavelength of 565 nm or 800 nm by using a microplate reader.

As shown in FIGS. 10A to 10C, a detection signal was proportional to a blood sample concentration of each patient under various mixing conditions. This shows that since a large amount of protein nanoparticles are uniformly distributed at regular intervals in the three-dimensional porous hydrogel, there is little signal noise caused by non-specific bonding and each antibody is accurately detected with reproducibility.

Example 2

Manufacturing of Protein Nanorod-Immobilized Hydrogel (Manufacturing Expression Vector for Synthesis of Protein Nanorods Presenting Disease Marker Detection Probe)

Figure 11A:
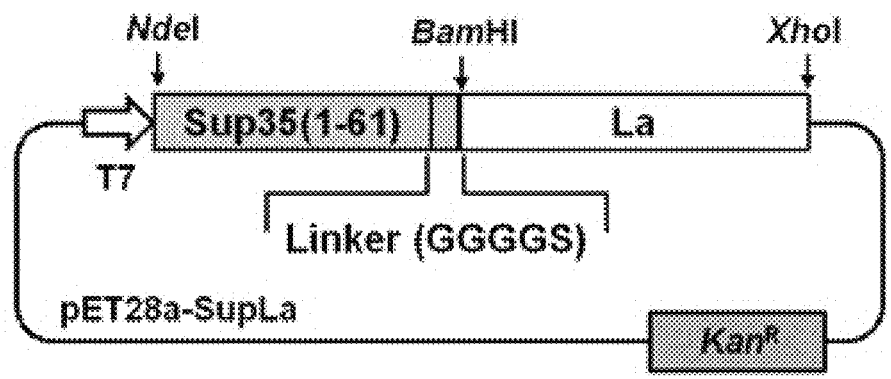
FIG. 11A shows a schematic diagram of a protein nanorod expression vector presenting a disease marker detection probe [Sjögren's autoantibody detection probe (La)]
Figure 11B:
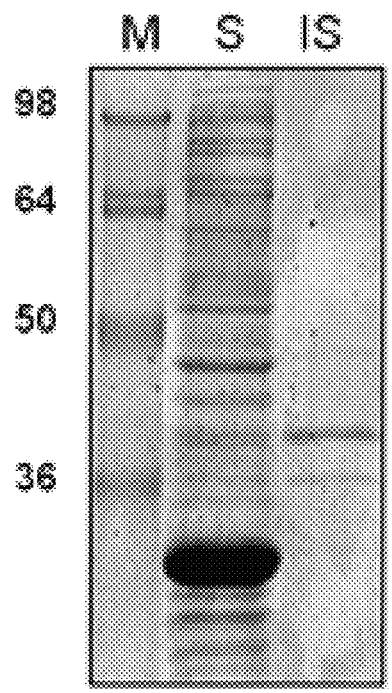
FIG. 11B shows an expression result of a water-soluble Sup35-La protein monomer expressed from the vector in $E.\ coli$.

A production vector was manufactured by inserting a Sjögren's syndrome autoantibody detection probe (La protein) gene into a carboxyl terminal of a *Saccharomyces cerevisiae*-derived Sup35 protein known to be in the form of nanorods by self-assembly (FIG. 11A), and the production vector was expressed in *E. coli* so as to manufacture a water-soluble Sup35-La protein monomer (FIG. 11B).

Gene clones for coding $NH_2$-NdeI-hexahistidine-[*Saccharomyces cerevisiae*-derived Sup35 protein 1-61 (SEQ ID NO:6)]-$G_4S$-BamHI-COOH and $NH_2$-BamHI-[human-derived La protein]-XhoI-COOH (or $NH_2$-BamHI-[human-derived La protein]-[biotin peptide]-XhoI-COOH) were PCR amplified by using an adequate primer and ligated to an NdeI-BamHI-XhoI cloning sites of pT7-7 and pET 28a, so that an expression vector pET28a-Sup35-La (or pT7-Sup35-La-biotin) for coding synthesis of a recombinant sup nanorod presenting disease marker detection probe on its surface was manufactured.

A nanorod assembly process was carried out by reference to the article "T. R. Serio, A. G et al., *Science*, 2000, 289, 1317-1321".

Figure 12:
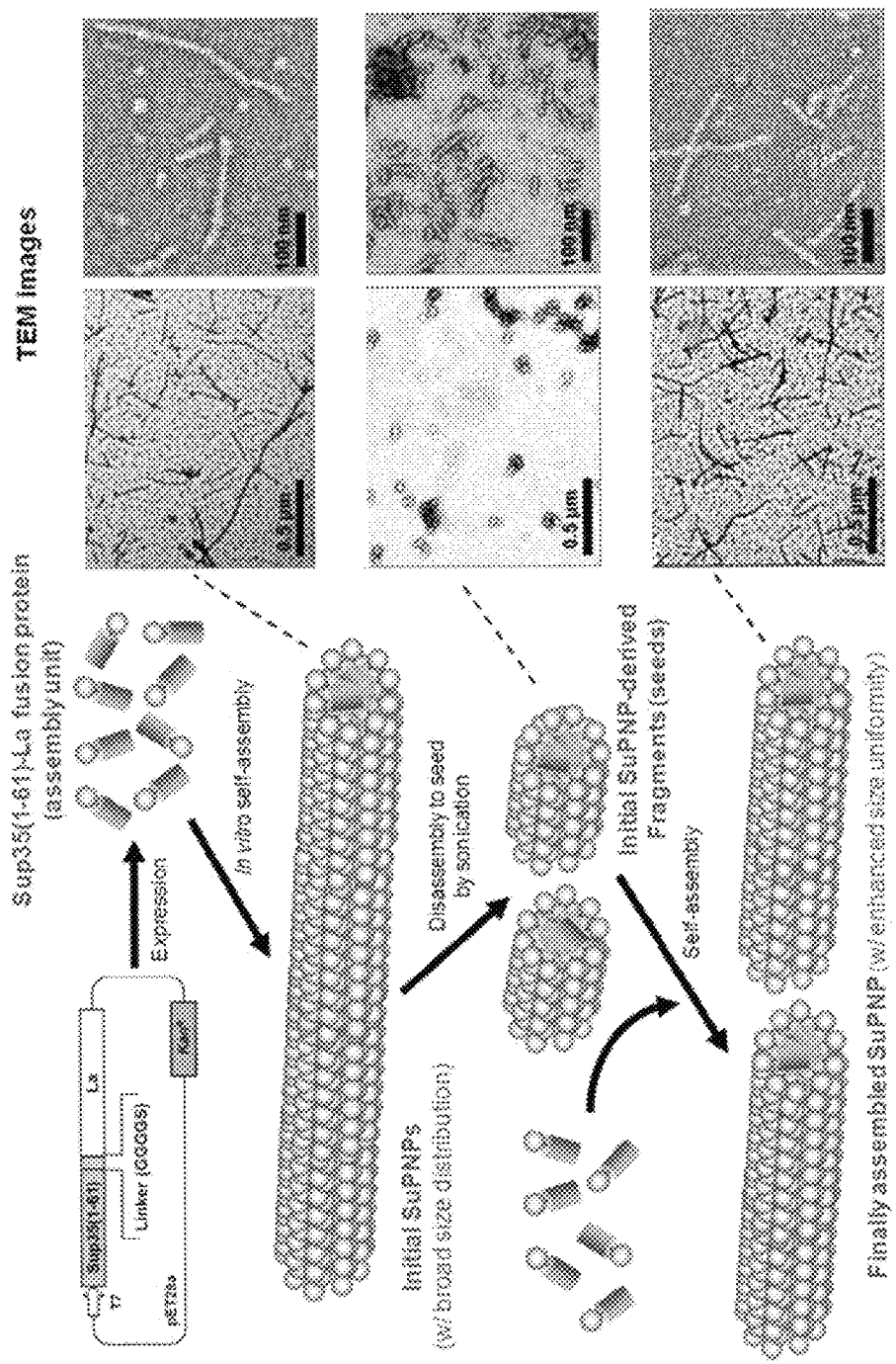
FIG. 12 provides a schematic diagram showing an assembly process of protein nanorods presenting multiple copies of disease marker detection probes with corresponding TEM images thereof.

Referring to TEM images of FIG. 12, a Sup35-La protein expressed in the form of a monomer within *E. coli* was manufactured into protein nanoparticles (SuPNP) in the form of nanorods through an in-vitro assembly process. However, it was impossible to control the nanorods ranging in length from several ten nm up to 1 μM (FIGS. 12(*a*) and 12(*b*)). Therefore, Sup35-La protein seeds each having a diameter of 10 nm were manufactured through a disassembly process using a sonicator (FIGS. 12(*c*) and 12(*d*)), and then the Sup35-La protein monomers and the Sup35-La protein seeds were mixed at a ratio of 1:8, so that protein nanoparticles in the form of nanorods having uniform diameters of 100 to 400 nm were finally manufactured (FIGS. 12(*e*) and 12(*f*)).

(Manufacturing of Protein Nanorod-Immobilized Hydrogel)

10 mg of streptavidin and 0.01 mg of N-succinimidyl-acrylate (NSA) were incubated in a PBS buffer at 37° C. for 1 hour and bound to each other. Then, non-bound NSA was removed by ultrafiltration (Amicon Ultra 100K), so that streptavidin having a polymerizable chemical structure was finally manufactured. 30 μg of the streptavidin and 0.45% polyacrylamide (29:1 W/W acrylamide:bis-acrylamide) were mixed in the presence of 0.125% w/v ammonium persulfate (APS) and 0.125% w/v tetramethylethylenediamine (TEMED), and each 150 μl of the mixture was apportioned into a 96-well plate and polymerized at 25° C. for 16 hours, so that a streptavidin fusion hydrogel was manufactured. 10 μg of Sup35-La-biotin nanorods was incubated in the streptavidin fusion hydrogel for 1 hour so as to be immobilized thereto.

Figure 13:
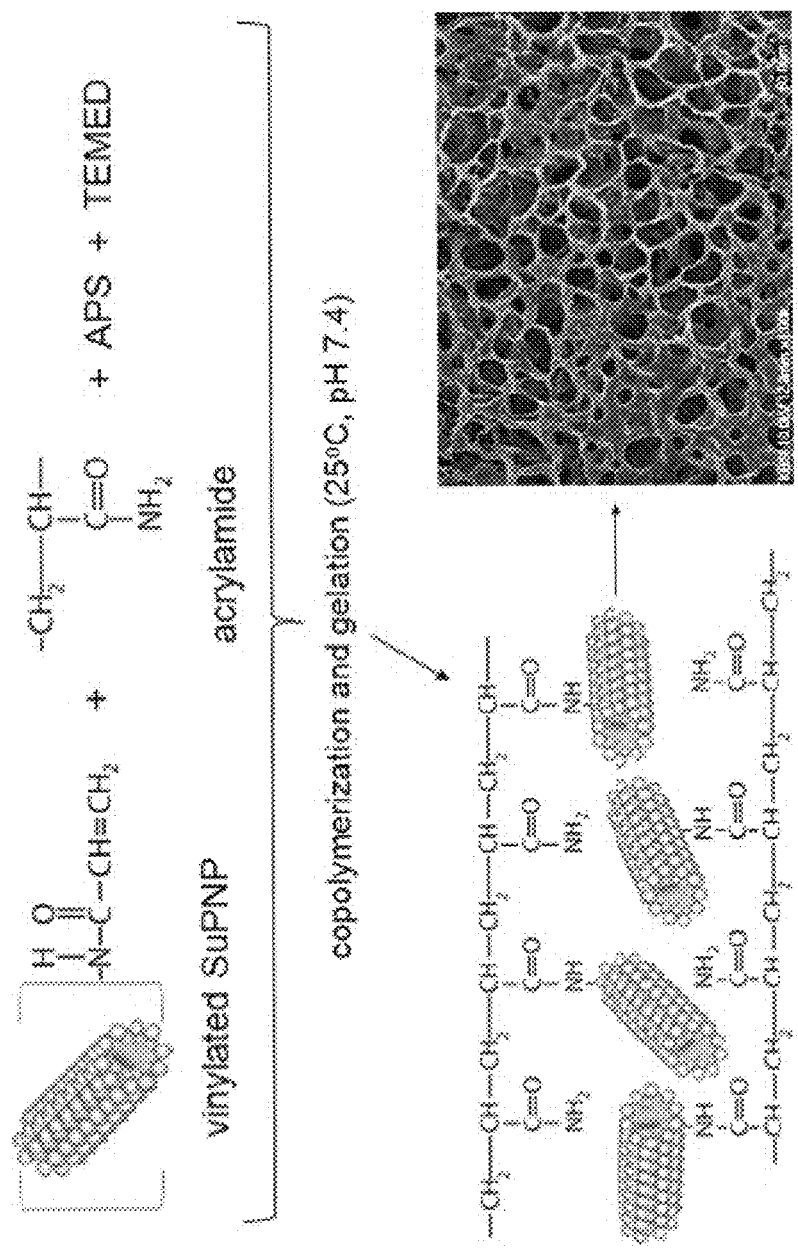
FIG. 13 provides a schematic diagram showing a manufacturing process of protein nanorods fusion hydrogel and a corresponding SEM image thereof.

It was confirmed from SEM images of FIG. 13 that the protein nanorods fusion hydrogel had a three-dimensional structure having very uniform porosity.

(Sensitivity Examination of Protein Nanorod-Immobilized Hydrogel Fusion Material)

Figure 14:
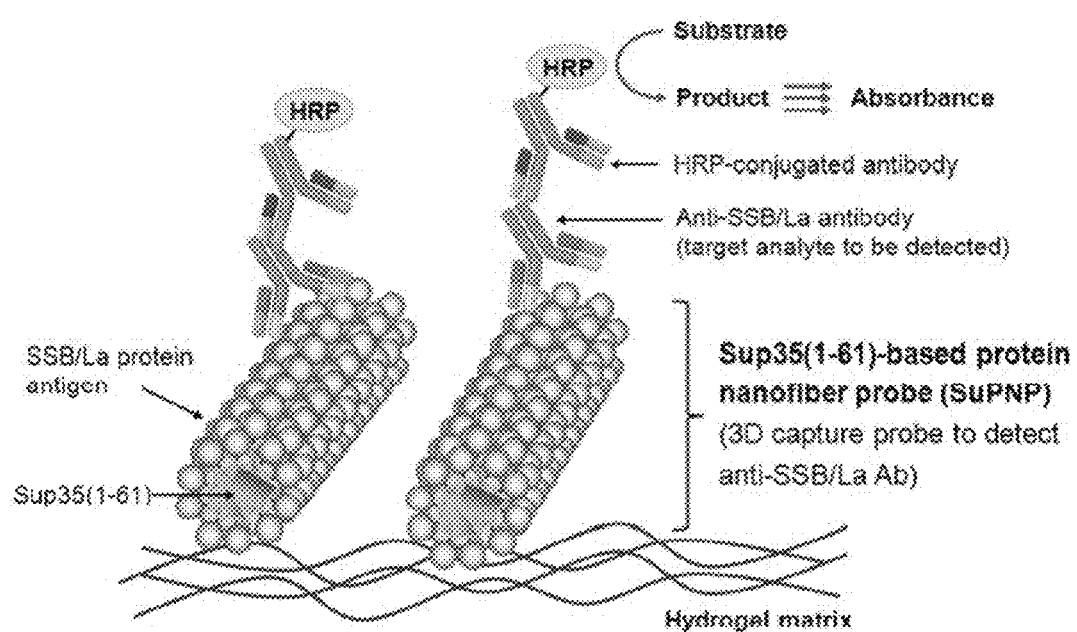
FIG. 14 is a schematic diagram of a target antibody detection system using protein nanorods fusion hydrogel for diagnosing Sjögren's syndrome.

In order to evaluate the utility and performance of a three-dimensional protein nanorods fusion hydrogel diagnosis system, sensitivity analysis was carried out. The sensitivity analysis was carried out by using an anti-La antibody. As shown in FIG. 14, a hydrogel fused with protein nanorods or a 2D PS surface was reacted with a sample (an anti-La antibody in a PBS buffer of different concentrations or an anti-La antibody in human blood), and then absorbance thereof was measured by using a secondary antibody bound to a HRP. Relative absorbance was obtained by deducting absorbance of a negative control group (with a concentration of 0) from the actually measured absorbance, and $LOD_H$ and $LOD_P$ denote LOD of SuPNP-hydrogel-based assay and LOD of 2D PS plate-based assay, respectively.

Figure 15:
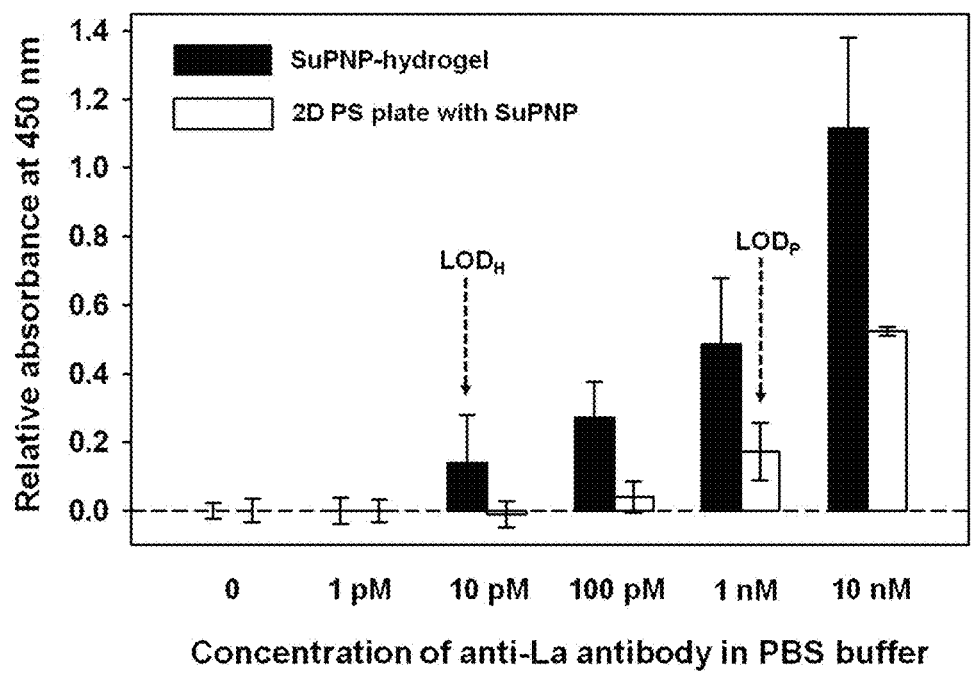
FIG. 15 shows sensitivity verification results of a target antibody detection system using protein nanorods fusion hydrogel for diagnosing Sjögren's syndrome in a PBS buffer.
Figure 16:
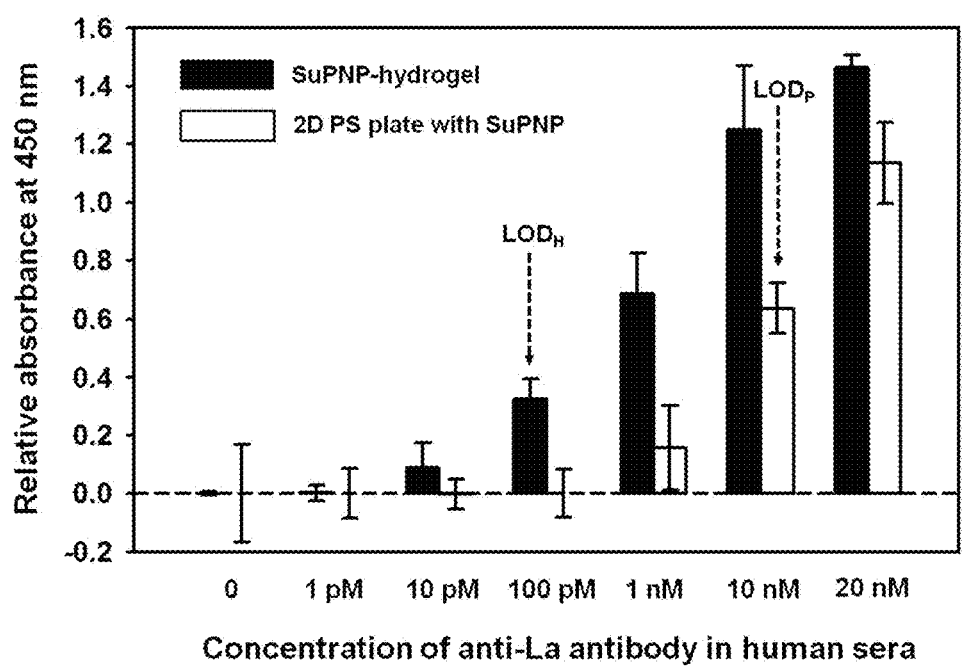
FIG. 16 shows sensitivity verification results of a target antibody detection system using protein nanorods fusion hydrogel for diagnosing Sjögren's syndrome in human serum.

As shown in FIGS. 15 and 16, the SuPNP-hydrogel showed sensitivity 100 times higher than the two-dimensional plate.

Figure 17:
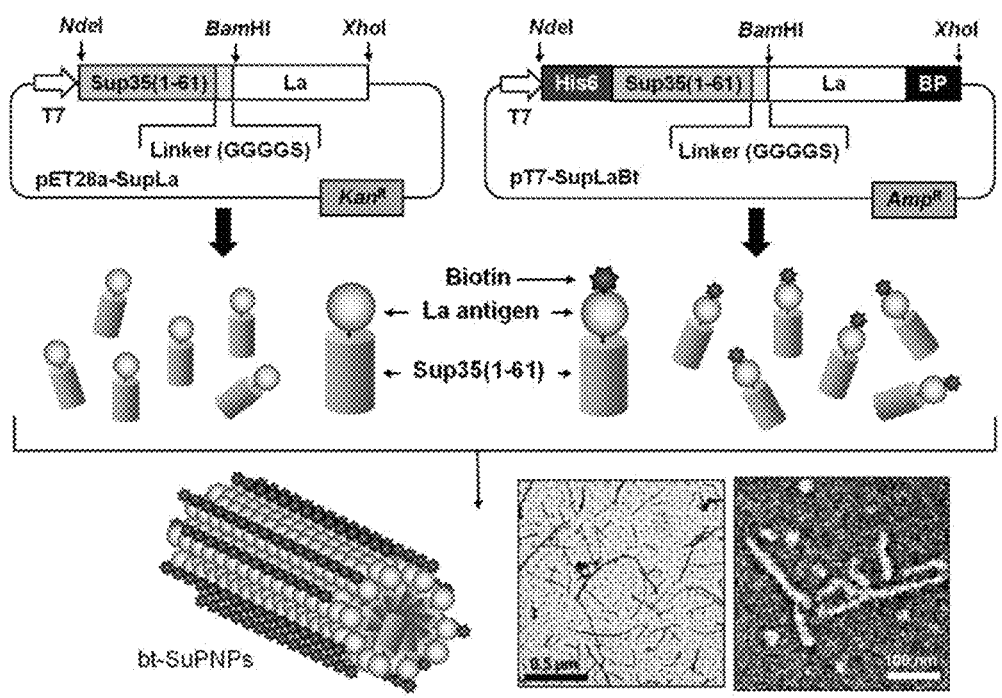
FIG. 17 provides a schematic diagram of a protein nanorod expression vector simultaneously presenting a disease marker detection probe [Sjögren's autoantibody detection probe (La)] and biotin, with corresponding TEM images thereof.

A production vector was manufactured by inserting a biotin peptide into a carboxyl terminal of the sup35-La protein in order to immobilize the protein nanorods to the hydrogel by means of biotin-streptavidin bonding instead of covalent bond. After the production vector was expressed in *E. coli*, a sup35-La protein monomer was manufactured into protein nanorods (SuPNP) presenting both biotin and a La protein through an in-vitro assembly process (FIG. 17).

Figure 18:
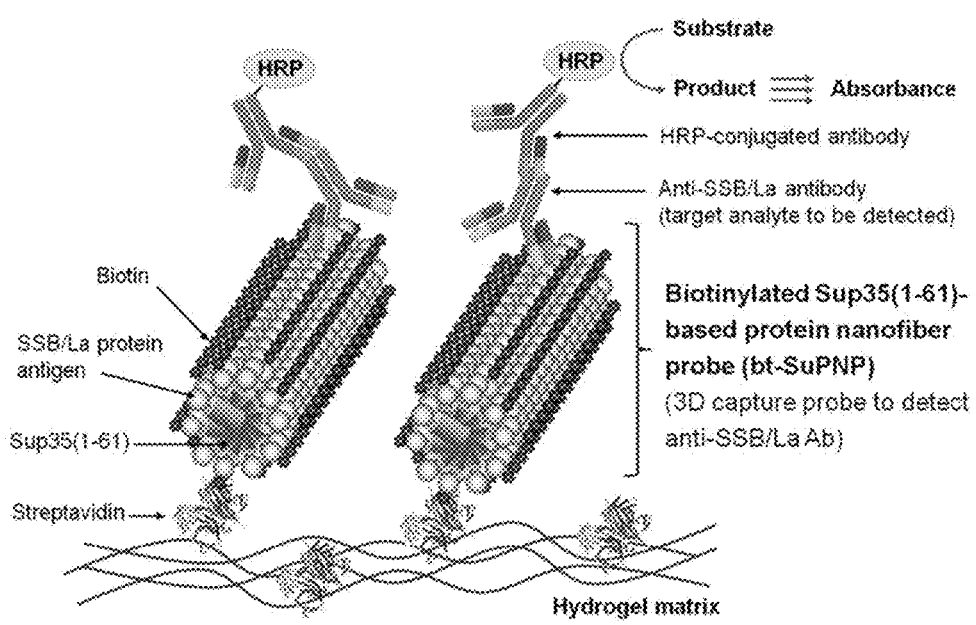
FIG. 18 is a schematic diagram of a target antibody detection system using a streptavidin-biotin bond-based protein nanorods fusion hydrogel.

The protein nanorods presenting both biotin and a La protein were immobilized to a hydrogel containing streptavidin by means of biotin-streptavidin bonding. In order to check utility and excellence of a three-dimensional biotin-streptavidin bond-based protein nanorods fusion hydrogel diagnosis system, a sensitivity analysis was carried out. The sensitivity analysis was carried out by using an anti-La antibody. As shown in FIG. 18, a hydrogel fused with protein nanorods (bt-SuPNP) was reacted with a sample (an anti-La antibody in a PBS buffer or an anti-La antibody in human blood), and then absorbance thereof was measured by using a secondary antibody bound to a HRP.

Figure 19:
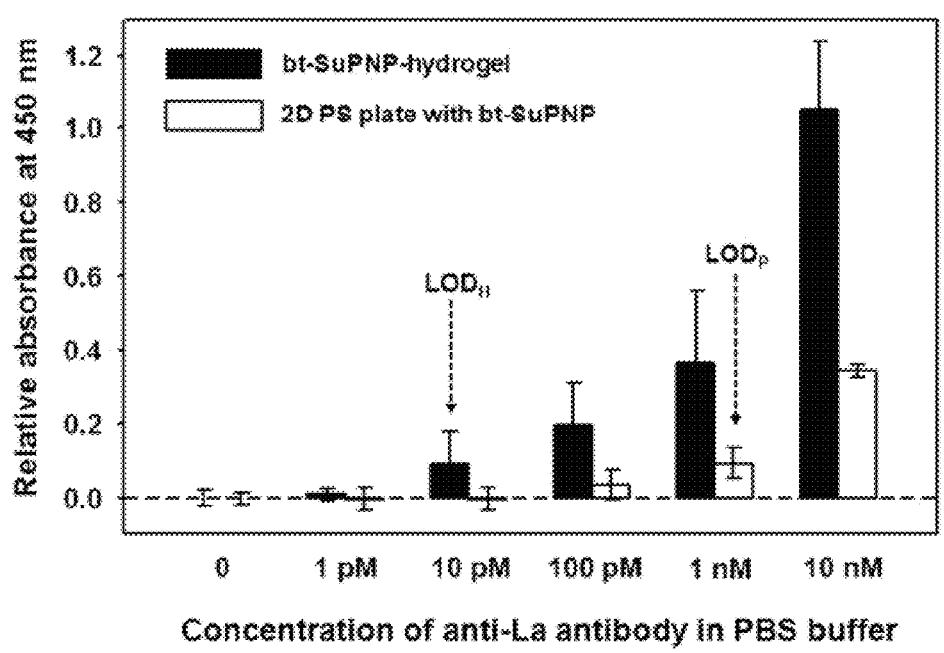
FIG. 19 shows sensitivity verification results of a target antibody detection system using a streptavidin-biotin bond-based protein nanorods fusion hydrogel in a PBS buffer.

As a result of a comparative analysis with a diagnosis system including protein nanorods immobilized to a two-dimensional polystyrene (PS) surface, the bt-SuPNP-hydrogel showed sensitivity 100 times higher than the two-dimensional diagnosis system (FIG. 19).

Example 3

Manufacturing of IgG/Fc-Binding Domain Displaying Spherical Protein Nanoparticle-Based Hydrogel to Detect Antigen Disease Marker (Biosynthesis of Surface-Engineered Protein Nanoparticles Displaying the IgG/Fc-Binding Domain ($SPA_B$))

Figure 21A:
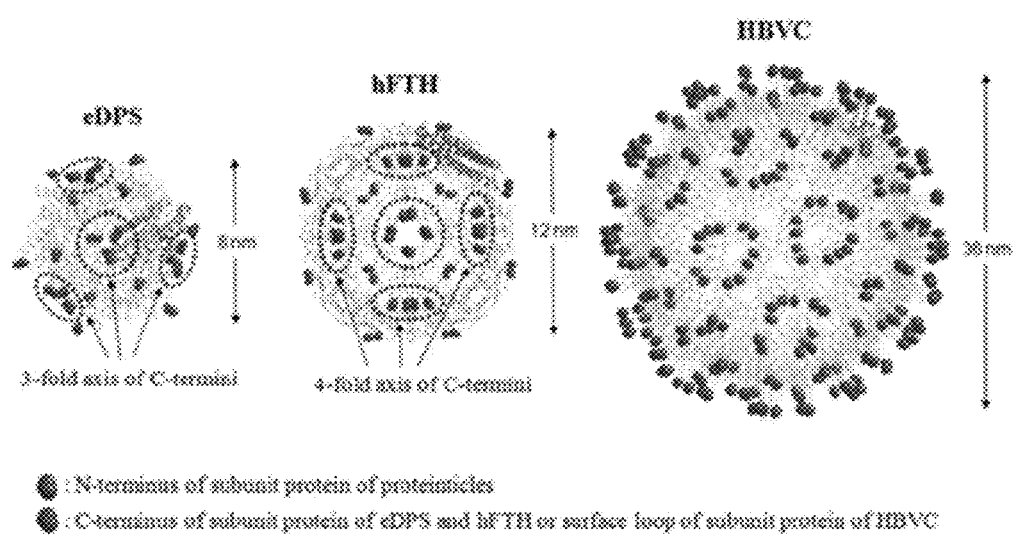
FIG. 21A shows the detailed 3D structure of protein nanoparticles with a spherical shape (eDPS, hFTH, and HBVC) showing all the N- and C-termini of subunit proteins of eDPS and hFTH, and surface loop regions of subunit proteins of HBVC.
Figure 21B:
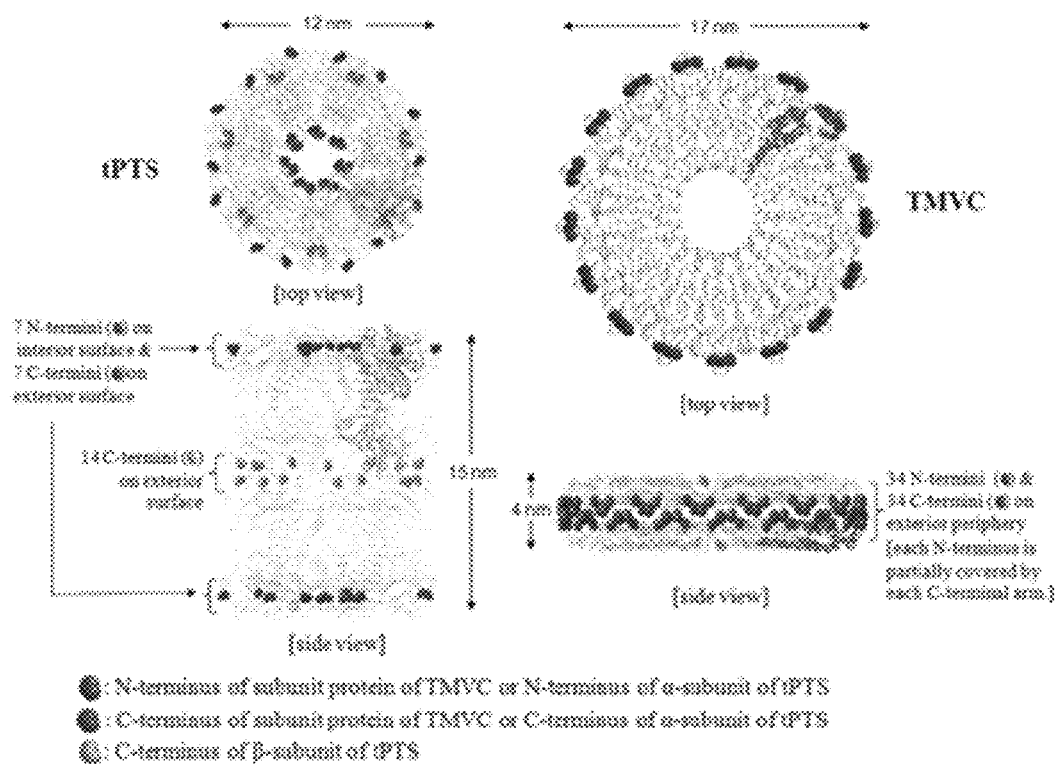
FIG. 21B shows the detailed 3D structure of protein nanoparticles with non-spherical shapes, i.e. disk shape (TMVC) and cylindrical shape (tPTS) showing all the N- and C-termini of subunit proteins of TMVC and tPTS.
Figure 22A:
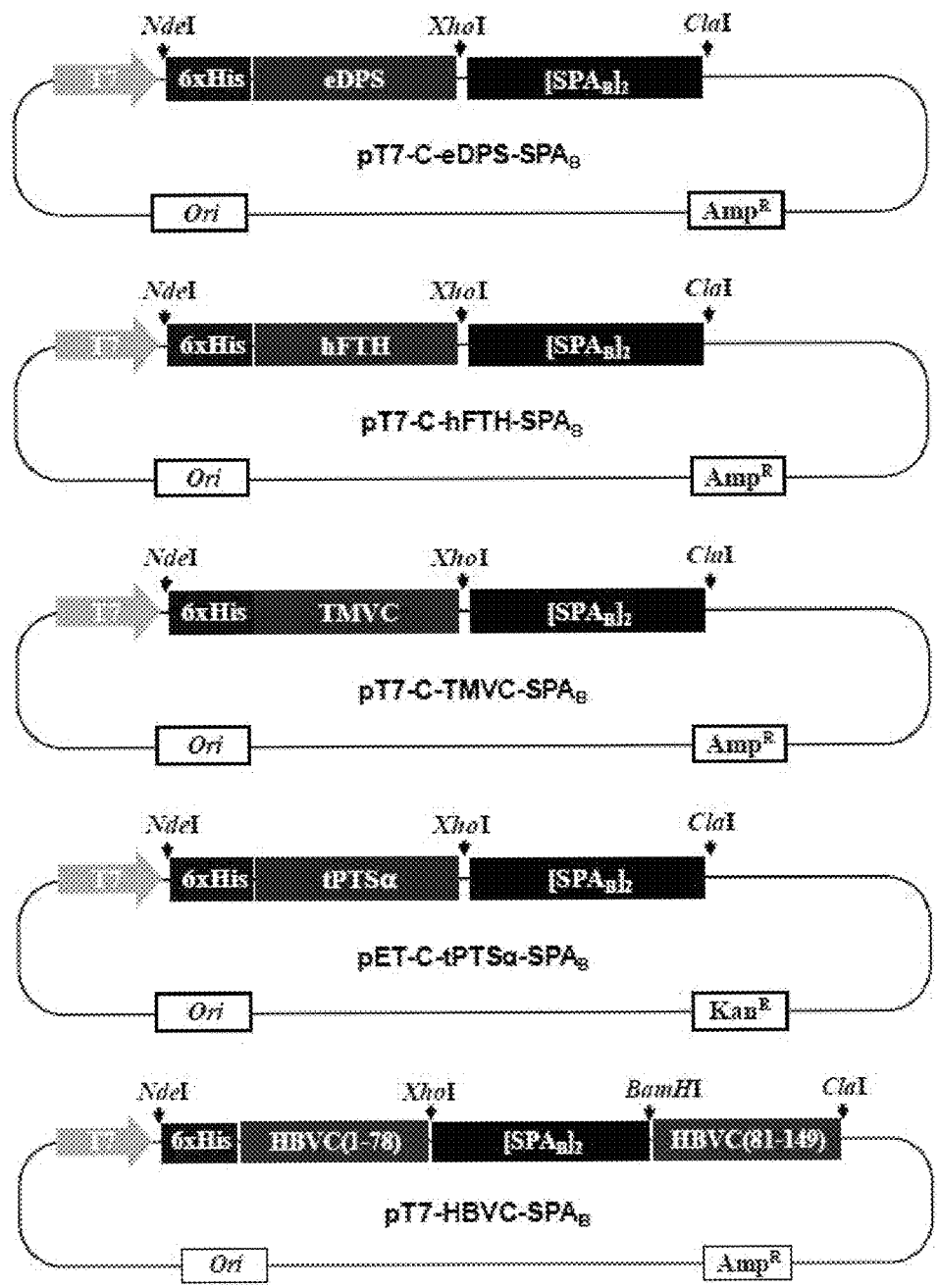
FIGS. 22A and 22B shows plasmid expression vectors used for the synthesis of surface-engineered protein nanoparticles displaying $SPA_B$.
Figure 22B:
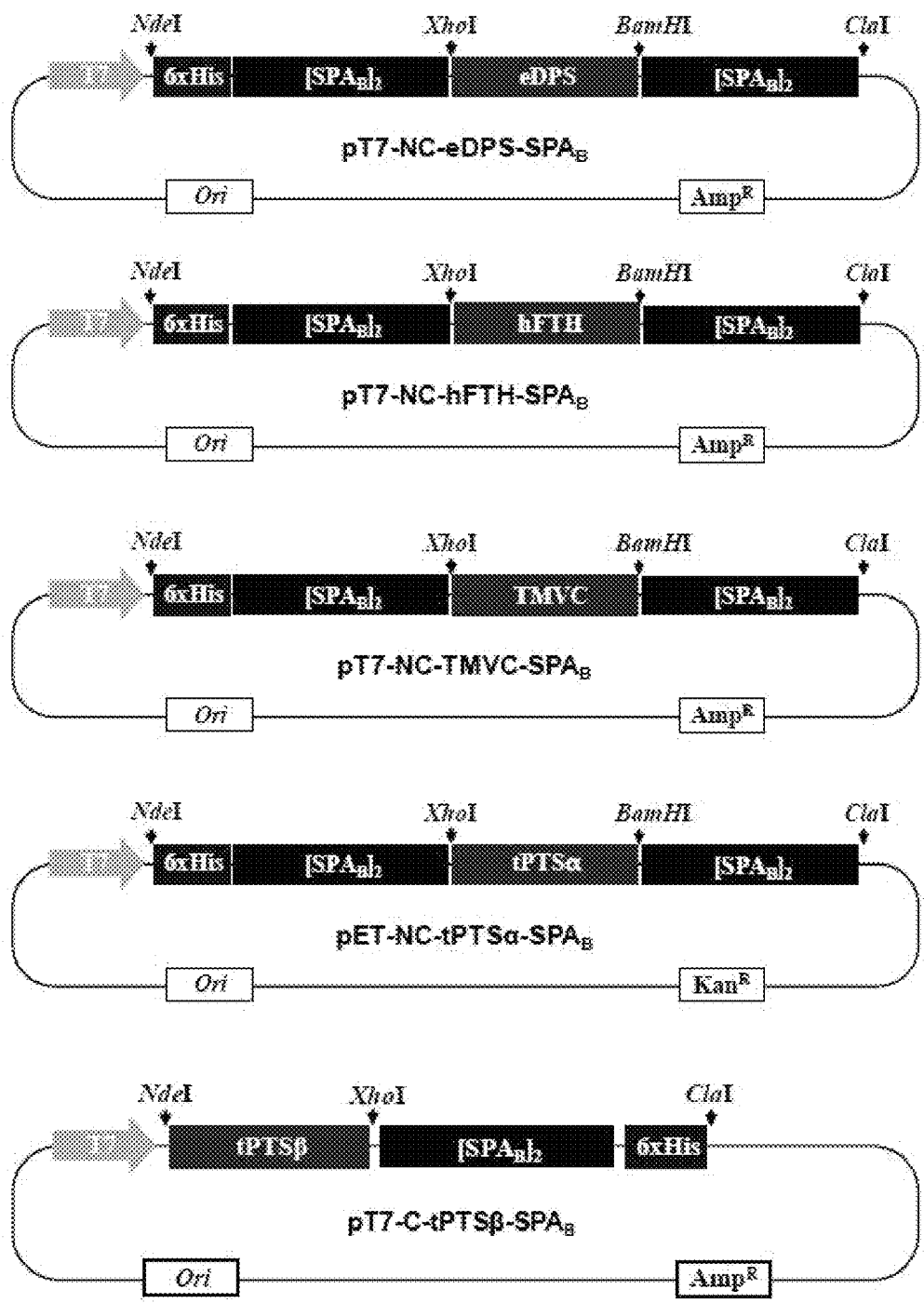
Figure 23A:
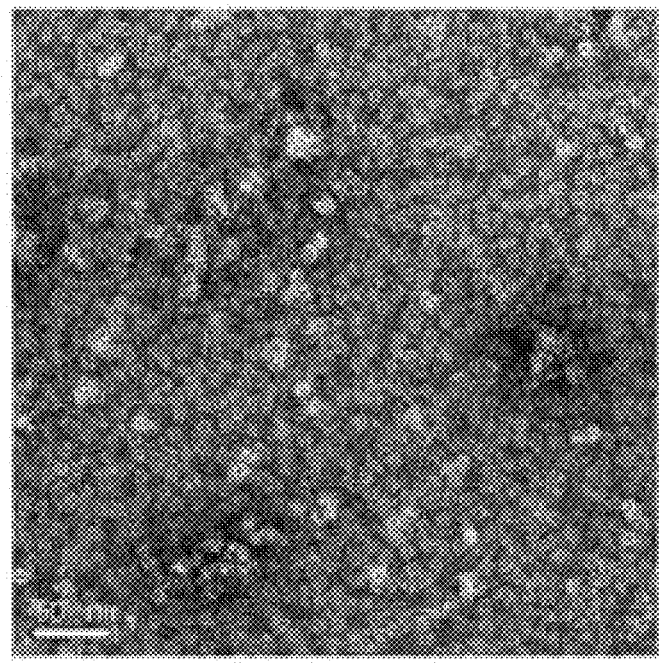
FIG. 23A shows a TEM image of the protein nanoparticle displaying $SPA_B$, $N\text{-}[SPA_B]_2\text{-}eDPS\text{-}[SPA_B]_2\text{-}C$.
Figure 23B:
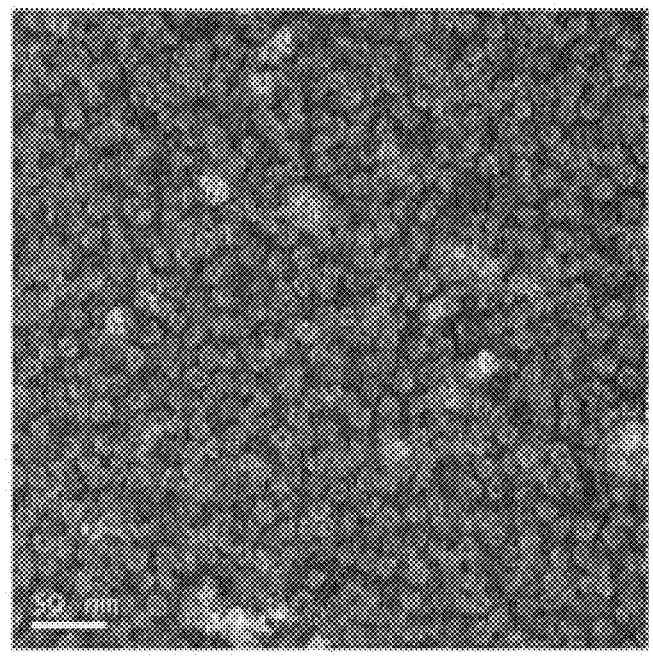
FIG. 23B shows a TEM image of the protein nanoparticle displaying $SPA_B$, $N\text{-}[SPA_B]_2\text{-}hFTH\text{-}[SPA_B]_2\text{-}C$.
Figure 23C:
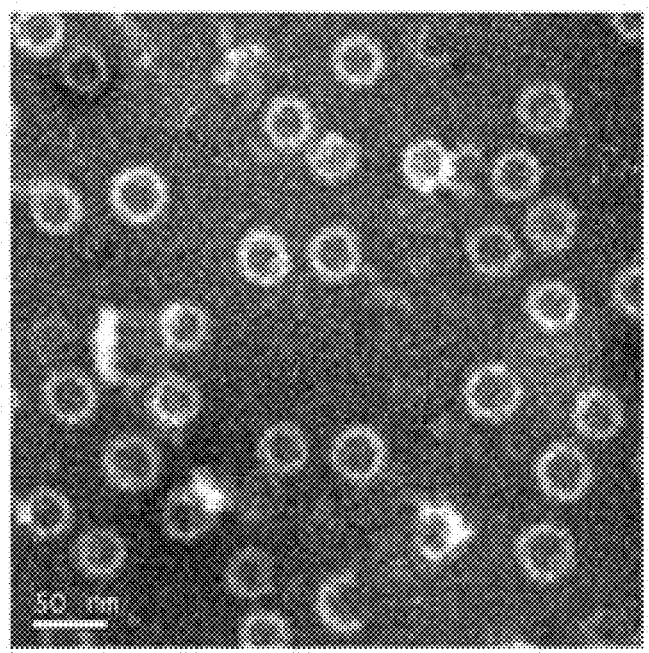
FIG. 23C shows a TEM image of the protein nanoparticle displaying $SPA_B$, $N\text{-}HBVC\text{-}[SPA_B]_2\text{-}HBVC\text{-}C$.
Figure 23D:
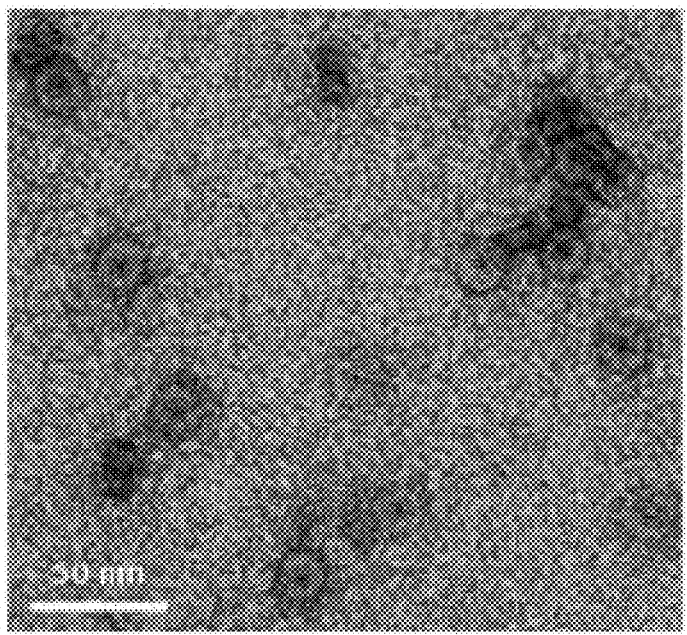
FIG. 23D shows a TEM image of the protein nanoparticle displaying $SPA_B$, $N\text{-}[SPA_B]_2\text{-}TMVC\text{-}[SPA_B]_2\text{-}C$.
Figure 23E:
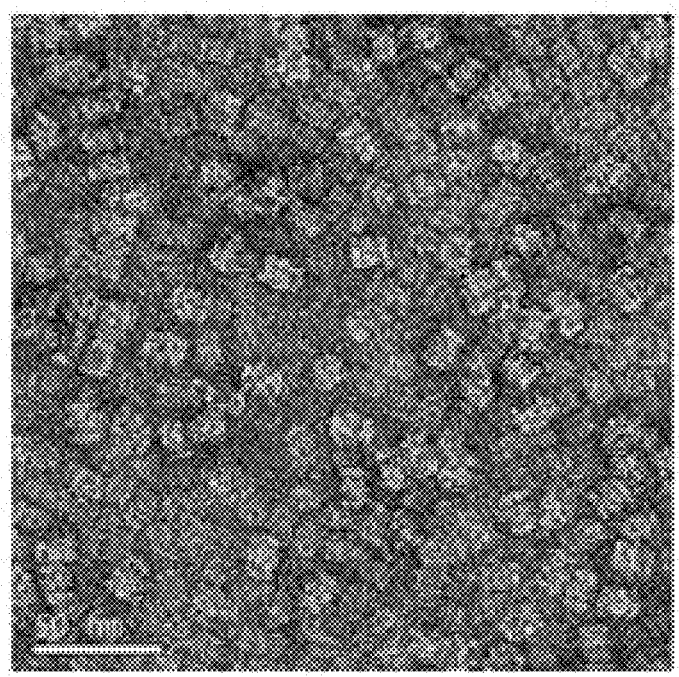
FIG. 23E shows a TEM image of the protein nanoparticle displaying $SPA_B$, $N\text{-}[SPA_B]_2\text{-}tPTS\alpha\text{-}[SPA_B]_2\text{-}C+N\text{-}tPTS\beta\text{-}[SPA_B]_2\text{-}C$.
Figures 1, 24A:
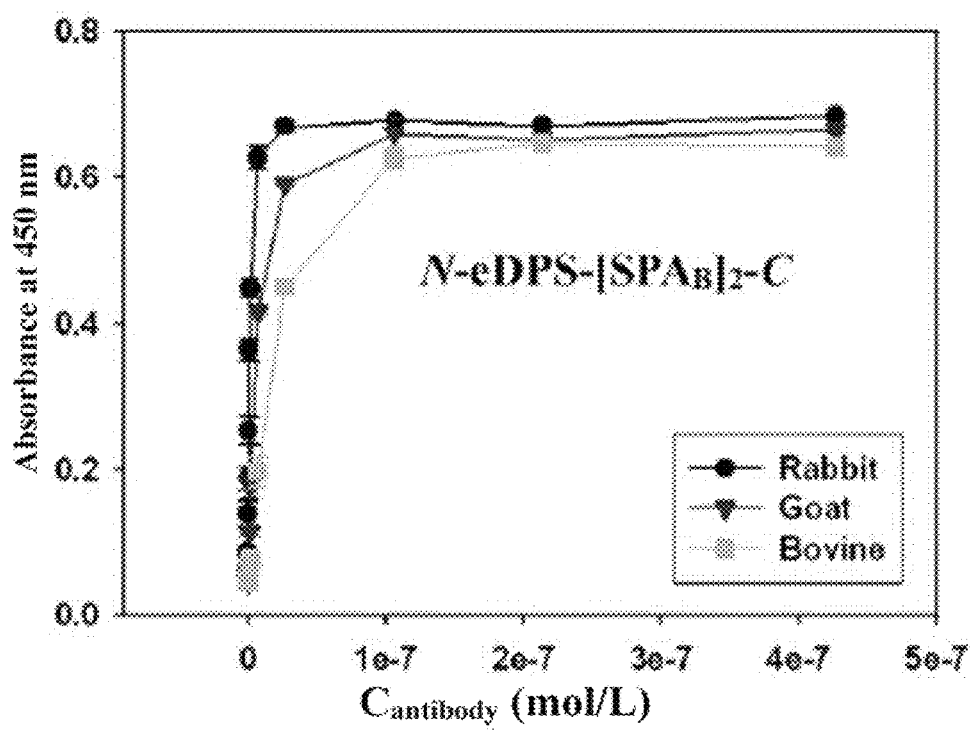
Figures 2, 24A:
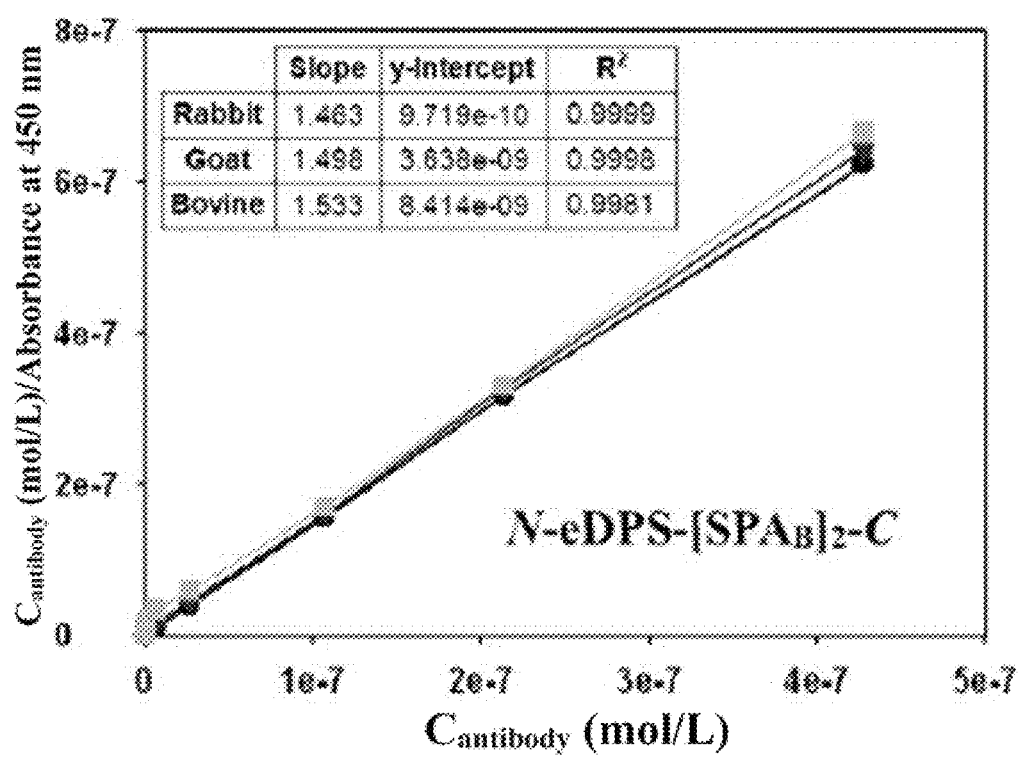
Figures 1, 24B:
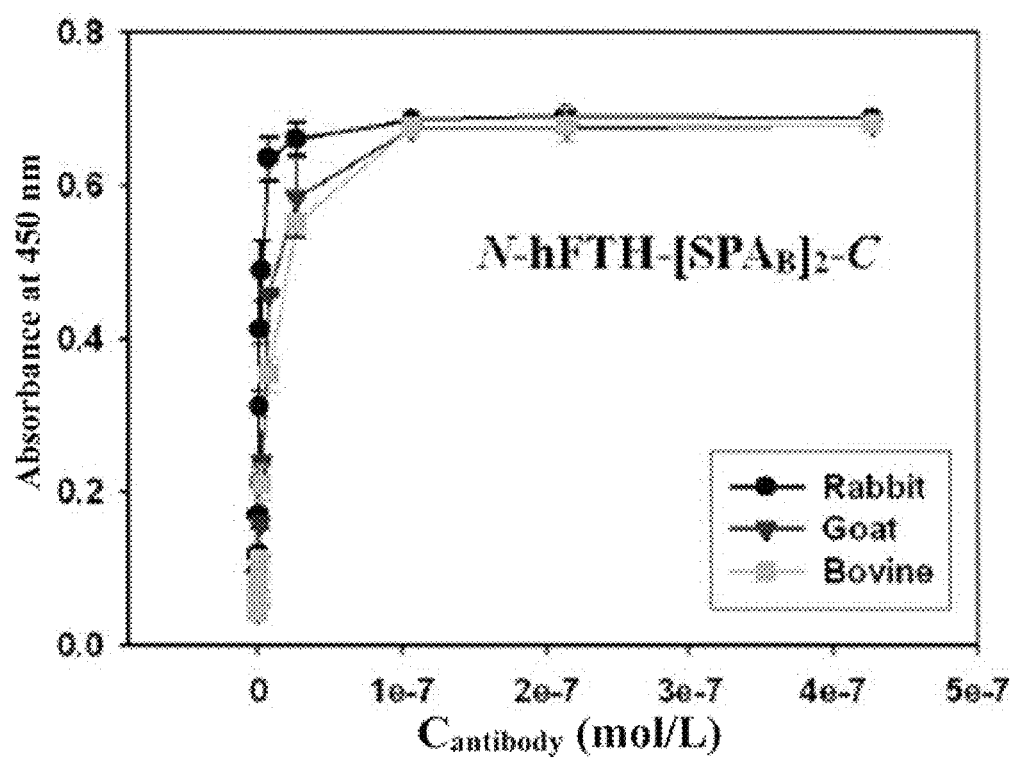
Figures 2, 24B:
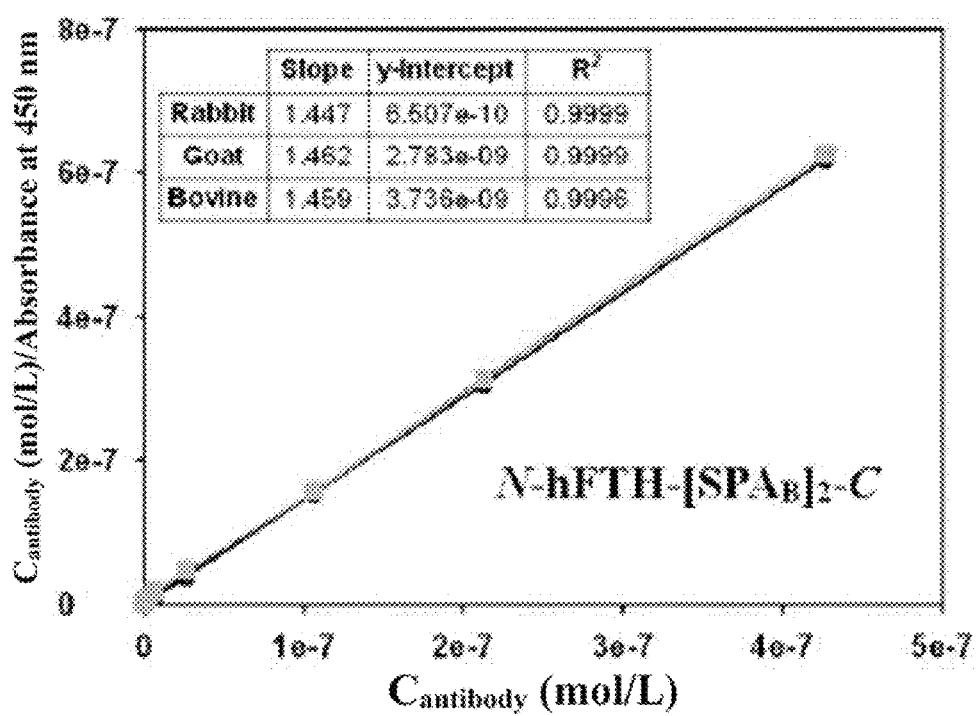
Figures 1, 24C:
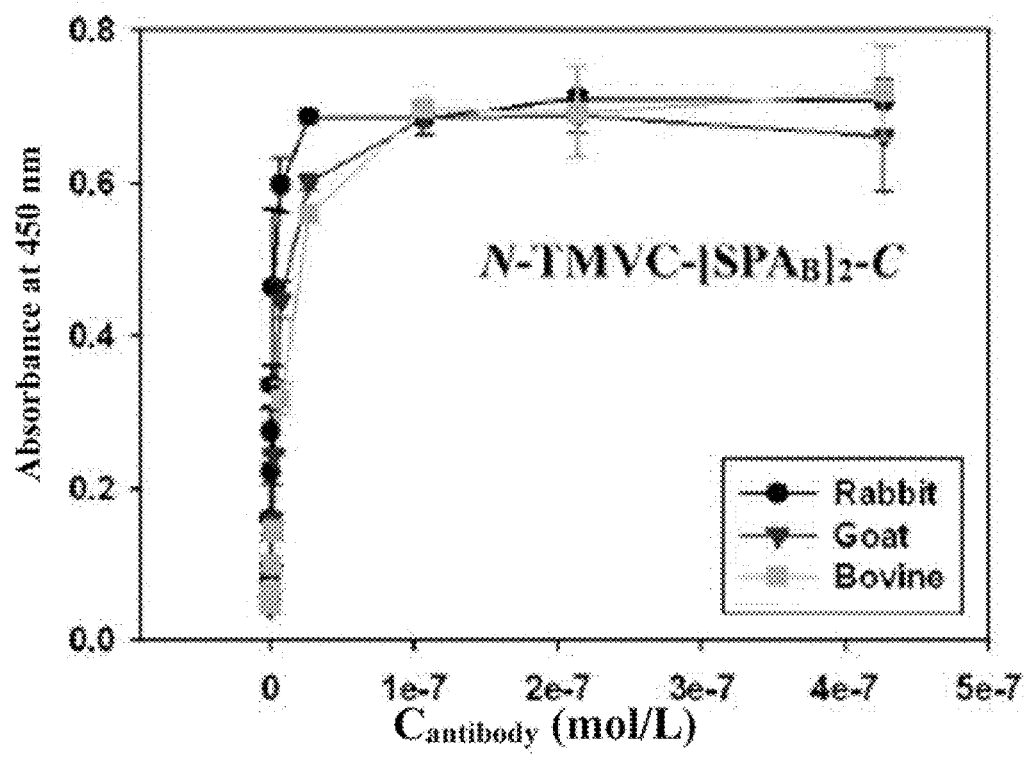
Figures 2, 24C:
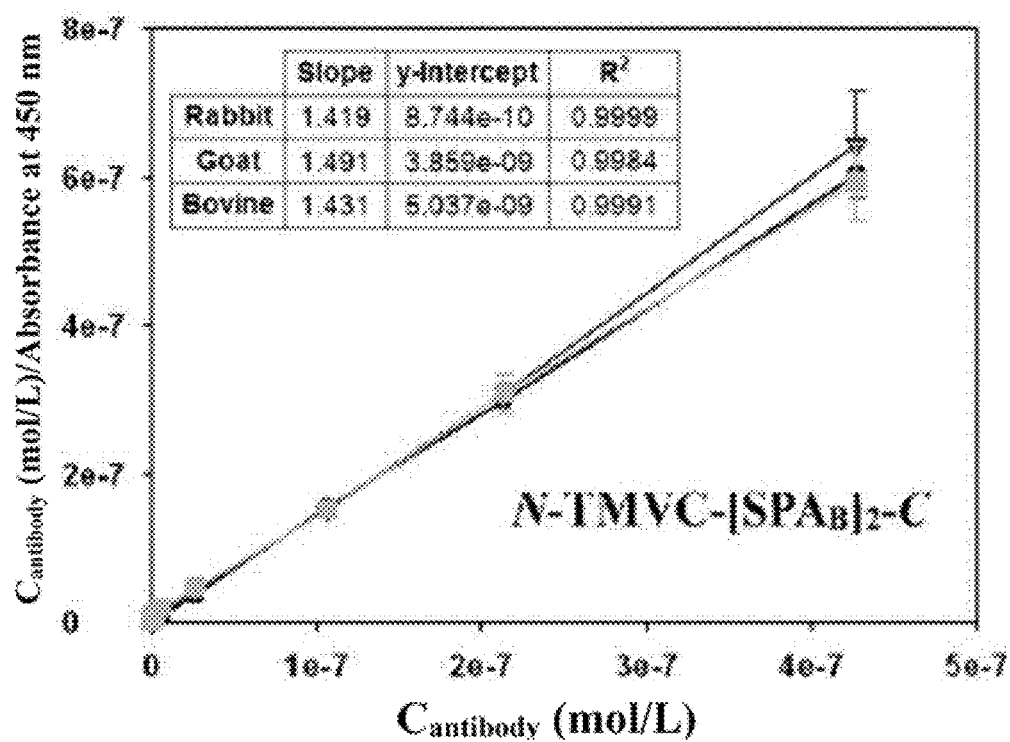
Figures 1, 24D:
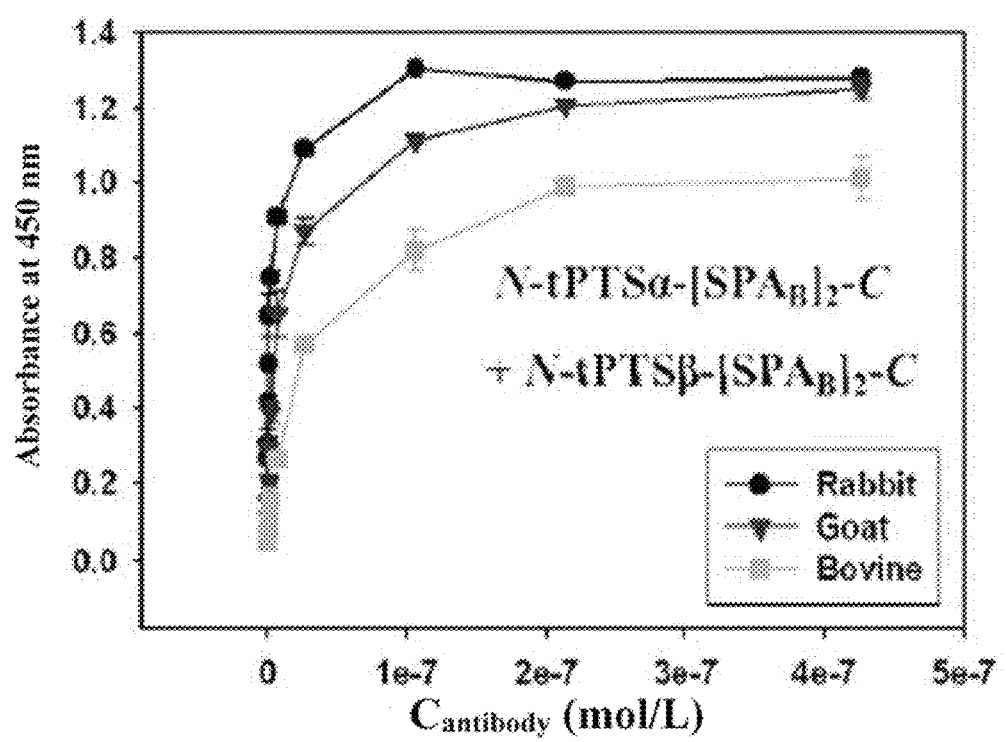
Figures 2, 24D:
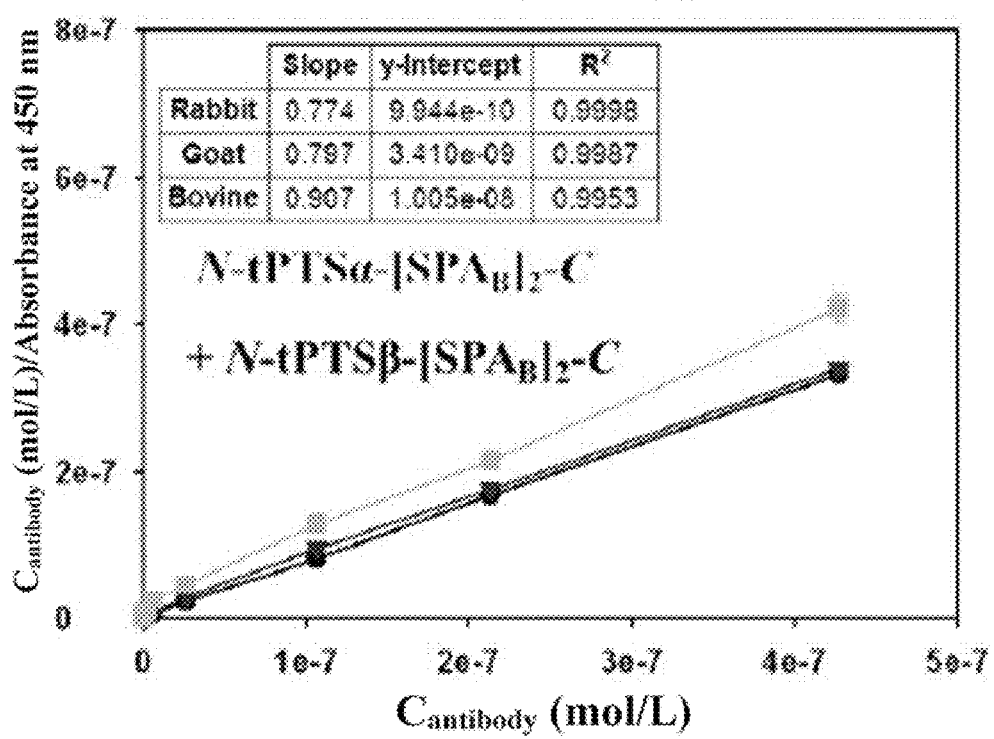
Figures 1, 24E:
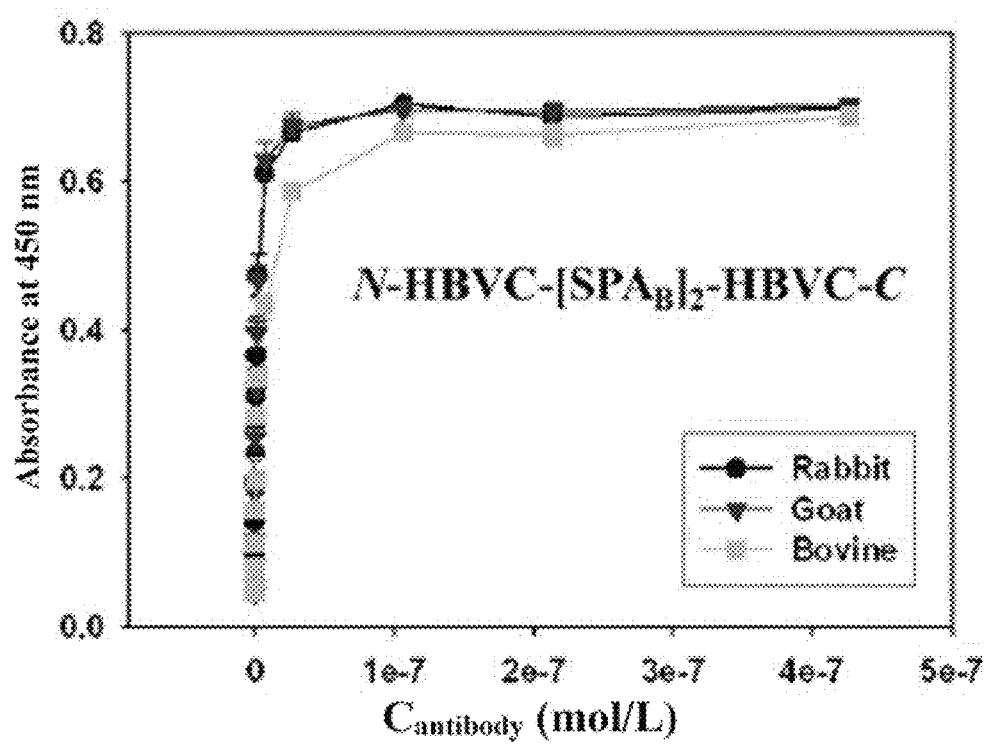
Figures 1, 24F:
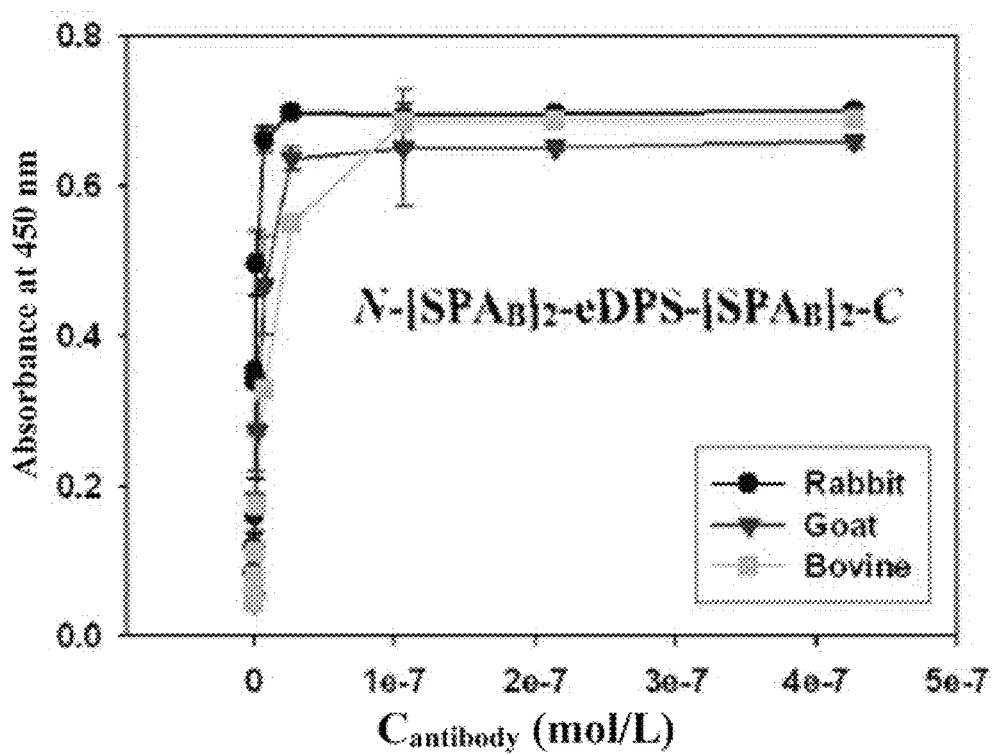
Figures 2, 24F:
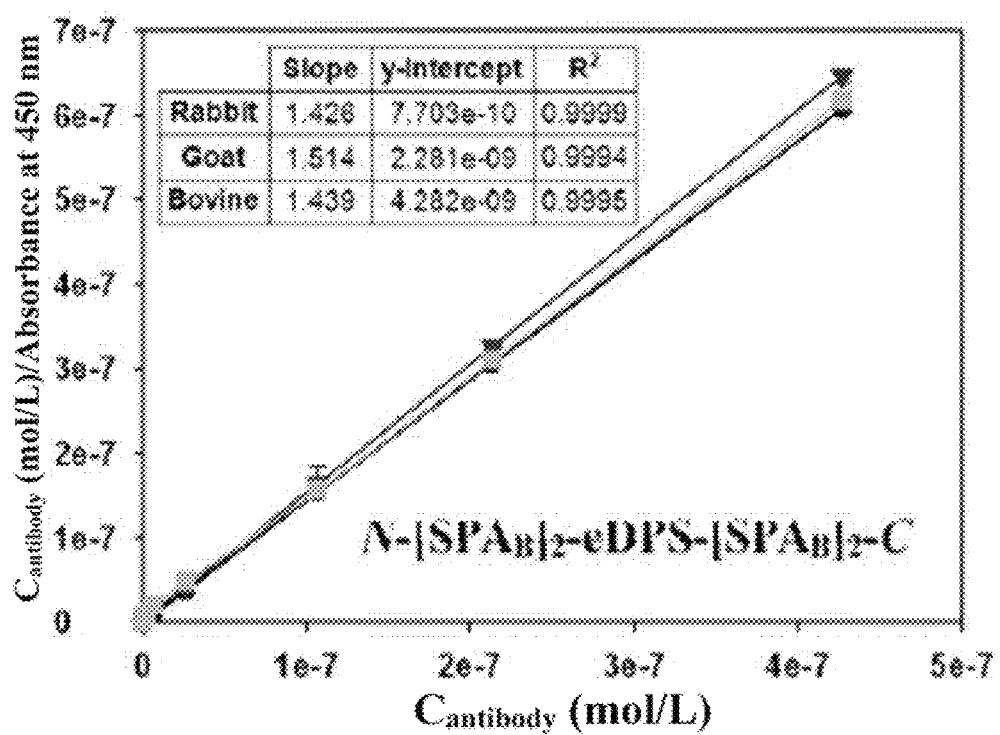
Figures 1, 24G:
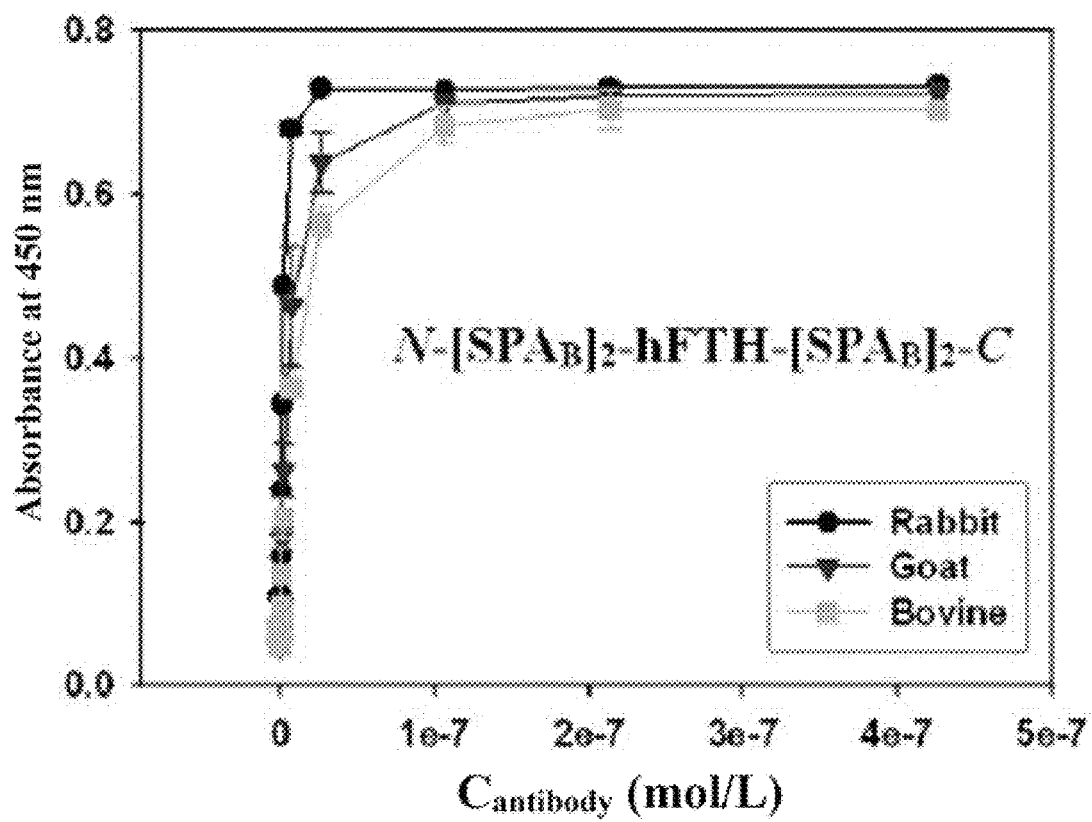
Figures 2, 24G:
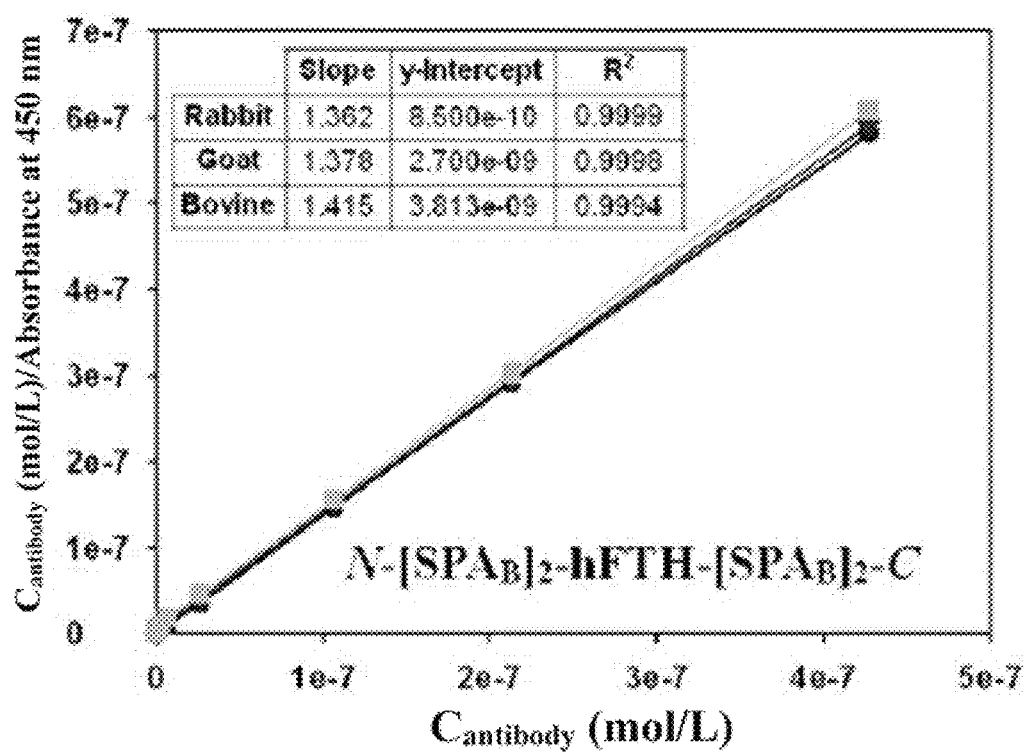
Figures 1, 24H:
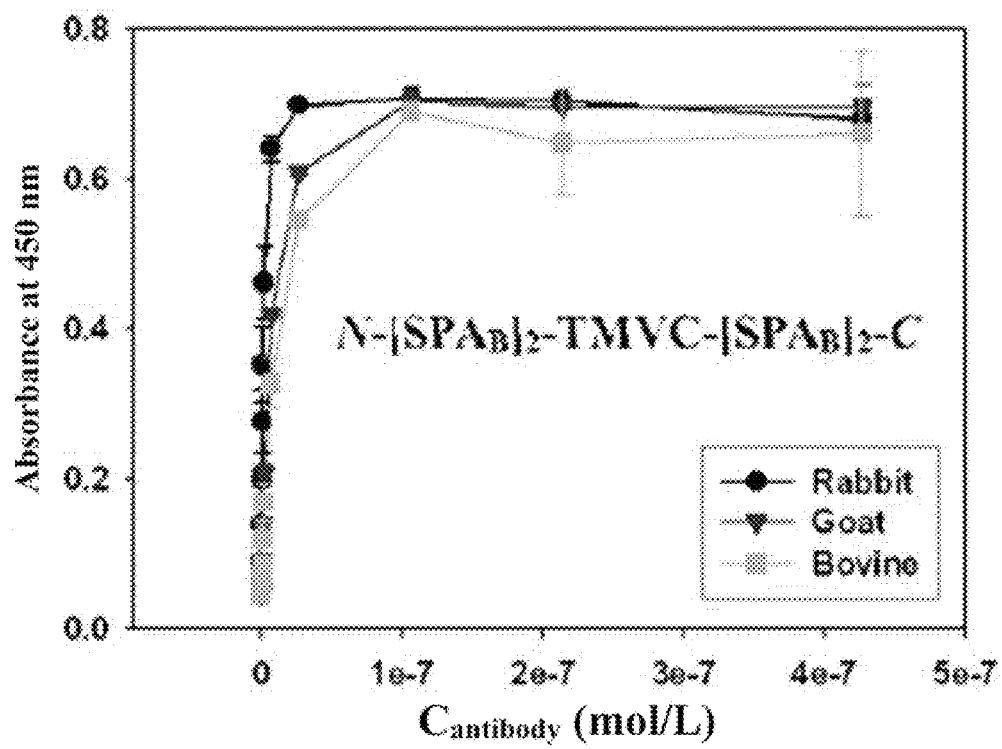
Figures 2, 24H:
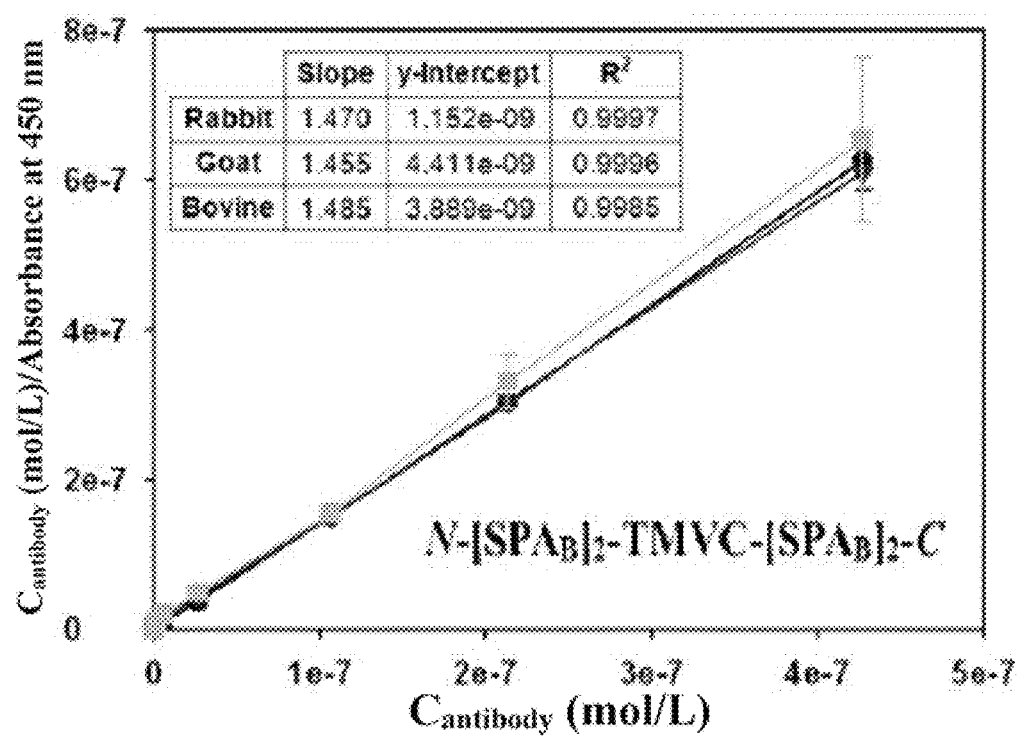
Figures 1, 24I:
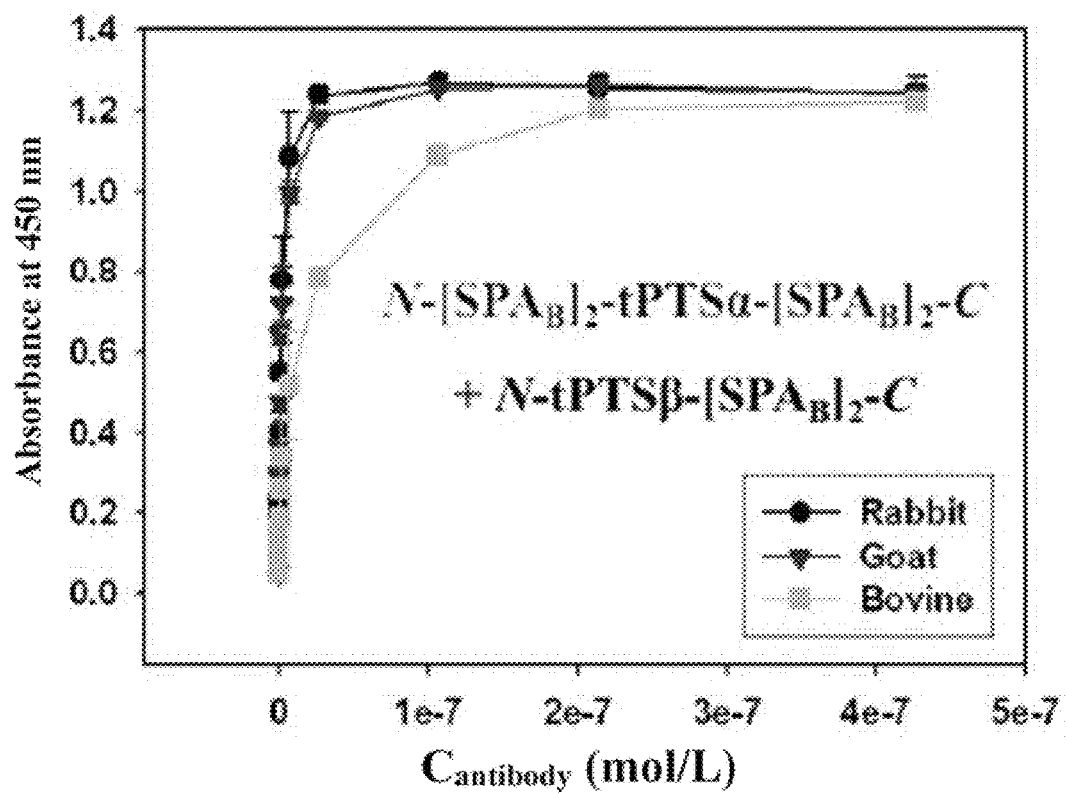
Figures 2, 24I:
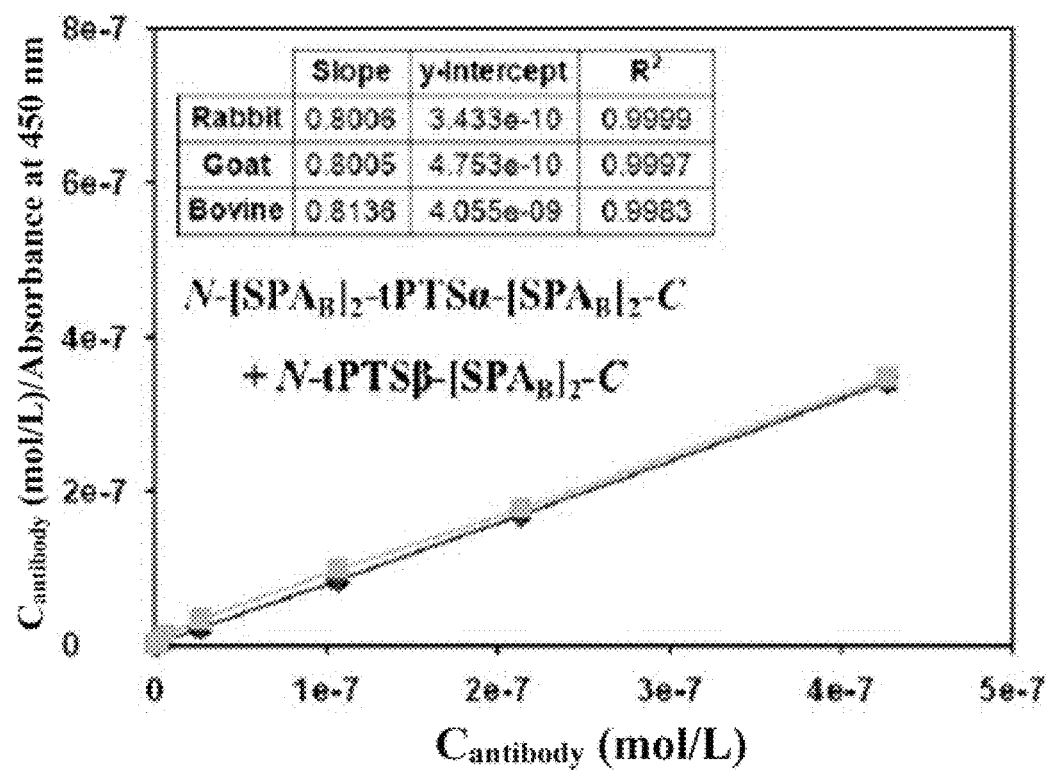

The five different protein nanoparticles that originate from humans, bacteria, and viruses and totally differ in size, shape, and surface structure, including eDPS (12 subunits/spherical/8.5 nm), hFTH (24 subunits/spherical/12 nm), HBVC (240 subunits/spherical/36 nm), TMVC (34 subunits/disk-shaped/17×4 nm), and tPTS (28 subunits/cylindrical/12×15 nm), were used as 3D nanostructure scaffolds for the surface display of the IgG/Fc-binding domain ($SPA_B$) (FIG. 20). For the effective surface display, the N- or C-terminus or internal region of subunit protein, protruding out of the protein nanoparticle surface (marked as blue or red dots in FIGS. 21A and 21B), was appropriately selected for the insertion of tandem $SPA_B$: both N- and C-terminus or only the C-terminus of the eDPS subunit, both N- and C-terminus or only the C-terminus of the hFTH subunit, the internal loop of the HBVC subunit, both N- and C-terminus or only the C-terminus of TMVC, both N- and C-terminus or only the C-terminus of the tPTS α-subunit, and only the C-terminus of the tPTS β-subunit. The 10 expression vectors were constructed for the synthesis of 9 surface-engineered protein nanoparticles displaying $SPA_B$ (see FIG. 22).

Through PCR amplification using the appropriate primers, ten gene clones were prepared, encoding N-NdeI-$(His)_6$-eDPS (SEQ ID NO: 7)-linker ($G_3SG_3TG_3SG_3$)-XhoI-$(SPA_B)_2$ (SEQ ID NO: 8)-ClaI-C, N-NdeI-$(His)_6$-hFTH (SEQ ID NO:1)-linker-XhoI-$(SPA_B)_2$-ClaI-C, N-NdeI-$(His)_6$-TMVC (SEQ ID NO: 9)-linker-XhoI-$(SPA_B)_2$-ClaI-C, N-NdeI-$(His)_6$-tPTSα (SEQ ID NO: 10)-linker-XhoI-$(SPA_B)_2$-ClaI-C, N-$(His)_6$-HBVC(1-78) (SEQ ID NO: 11)-$G_4SG_4T$-XhoI-$(SPA_B)_2$-$G_4SG_4$-HBVC(81-149) (SEQ ID NO: 12)-ClaI-C, N-NdeI-$(His)_6$-$(SPA_B)_2$-linker-XhoI-eDPS-linker-BamHI-$(SPA_B)_2$-ClaI-C, N-NdeI-$(His)_6$-$(SPA_B)_2$-linker-XhoI-hFTH-linker-BamHI-$(SPA_B)_2$-ClaI-C, N-NdeI-$(His)_6$-$(SPA_B)_2$-linker-XhoI-TMVC-linker-BamHI-$(SPA_B)_2$-ClaI-C, N-NdeI-$(His)_6$-$(SPA_B)_2$-linker-XhoI-tPTSα-linker-BamHI-$(SPA_B)_2$-ClaI-C, and N-NdeI-tPTSβ-linker-XhoI-$(SPA_B)_2$-$(His)_6$-ClaI-C. eDPS, hFTH, HBVC, tPTS and $SPA_B$ genes were cloned using the previously cloned expression vector (J. S. Park et al. Nat. Nanotechnol., 2009, vol. 4, pp. 259), and the TMVC gene was cloned from a cDNA library containing mRNA from the upper leaves of *Nicotiana tabacum* cv *Xanthi nc* plants. Each gene clone was sequentially ligated into the pT7-7 or pET28a plasmid to construct the expression vector pT7-C-eDPS-$SPA_B$, pT7-C-hFTH-$SPA_B$, pT7-C-TMVC-$SPA_B$, pET-C-tPTSα-$SPA_B$, pT7-C-tPTSβ-$SPA_B$, pT7-HBVC-$SPA_B$, pT7-NC-eDPS-$SPA_B$, pT7-NC-hFTH-$SPA_B$, pT7-NC-TMVC-$SPA_B$, and pET-NC-tPTSα-$SPA_B$. After complete sequencing, *E. coli* BL21(DE3) was transformed with each of the seven expression vectors (pT7-N-eDPS-$SPA_B$, pT7-ChFTH-$SPA_B$, pT7-C-TMVC-$SPA_B$, pT7-HBVC-$SPA_B$, pT7-NCeDPS-$SPA_B$, pT7-NC-hFTH-$SPA_B$, and pT7-NC-TMVC-$SPA_B$) and ampicillin-resistant transformants were finally selected and used to synthesize the eDPS, hFTH, HBVC, and TMVC protein nanoparticles with the surface $SPA_B$. To synthesize the tPTS protein nanoparticles, *E. coli* BL21(DE3) was co-transformed by a pair of recombinant expression vectors (pET-C-tPTSα-$SPA_B$+pT7-CtPTSβ-$[SPA_B]_2$ or pET-NC-tPTSα-$SPA_B$+pT7-C-tPTSβ-$SPA_B$), and both kanamycin- and ampicillin-resistant transformants were selected. The detailed procedures for recombinant gene expression, recombinant protein nanoparticle purification, and TEM image analysis are well described in Example 1.

(Preparation of Protein Nanoparticle-Embedded 3D Porous Hydrogel)

The synthesized protein nanoparticles (or $SPA_B$) were modified by N-succinimidyl-acrylate (NSA, 0.01 mg) in PBS buffer (137 mM NaCl, 2.7 mM KCl, 10 mM $Na_2HPO_4$, 2 mM $KH_2PO_4$, pH 7.4) for 1 h at 37° C., resulting in the synthesis of vinylated protein nanoparticles (or $SPA_B$). Unreacted NSA was eliminated by ultrafiltration (Amicon Ultra 100 K, Millipore, Billerica, Mass.). The vinylated protein nanoparticles (1 μg in the case of hFTH), 9% acrylamide (29:1 w/w acrylamide:bis-acrylamide), and 0.125% w/v ammonium persulphate (APS) were reacted, and immediately after the addition of 0.125% v/v tetramethylethylenediamine (TEMED), 50 μl of the reaction mixture above was immediately loaded into a transparent 96 well plate (Corning, N.Y., USA) and copolymerized for 16 h at 25° C. A more detailed procedure to prepare the protein nanoparticle (or $SPA_B$)-embedded hydrogel is well described in Example 1.

(Estimation of the Dissociation Constant ($K_D$) in the Binding of IgG/Fc to $SPA_B$ on Protein Nanoparticles)

For the $K_D$ estimation in the binding between IgG and $SPA_B$ on protein nanoparticles, the HRP-conjugated IgGs (HRP-IgGs) originating from three different species [rabbit anti-sheep antibody (cat. no. SC-2770, Santa Cruz Biotechnology Inc., Texas, USA), goat anti-mouse antibody (cat. no. SC-2005, Santa Cruz Biotechnology Inc., Texas, USA), bovine anti-goat antibody (cat. no. SC-2770, Santa Cruz Biotechnology Inc., Texas, USA), and human anti-human antibody (cat. no. 31465, Pierce Biotechnology Inc., Rockford, USA)] were used. The hydrogel containing each of the surface-engineered protein nanoparticles was pre-wetted with PBS buffer, and each of the HRP-IgGs at various concentrations in 10% Superblock (PBS) blocking buffer (100 μl) was added to each well, followed by 2 h incubation with slow agitation at room temperature. After washing twice with PBS buffer for 10 min, 50 μl of tetramethylbenzidine (TMB) substrate solution (Pierce Biotechnology Inc., Rockford, USA) was added to each well and incubated for 10 min, and HRP enzyme reaction was stopped by adding 50 μl of stop solution (1 N sulfuric acid). The absorbance signal at 450 nm was measured using a microplate reader (Infinite M200 Pro, TECAN, Austria). The dissociation constant ($K_D$) in the binding between $SPA_B$ and IgG/Fc was estimated based on the principle of the Langmuir adsorption isotherm: according to the linearized equation of the adsorption isotherm, C/Abs=C/Abs(sat)+KD/Abs(sat), where C, Abs, Abs (sat), and $K_D$ represent the concentrations of IgG [HRP-conjugated IgG (HRP-IgG) in this case], \ absorbance signal, saturated absorbance signal, and dissociation constant, respectively. The absorbance signal generated by HRP-substrate reaction in hydrogel was assumed to be proportional to the amount of HRP-IgG bound to $SPA_B$ in the hydrogel. All the analysis results were presented with error bars based on triplicate assay experiments.

As shown in FIG. 23A to 23E, when expressed in *E. coli*, the genetically modified subunit proteins were self-assembled to form the surface-engineered protein nanoparticles, as confirmed by TEM analysis.

Each of the 9 surface-engineered protein nanoparticles was immobilized onto the surface of porous hydrogel, which provides a moisturized 3D space where a large amount of properly oriented proteins can be uniformly distributed with stably preserving the activity. Each protein nanoparticle is composed of a unique number of subunit proteins and hence is subject to displaying a unique number of $SPA_B$ molecules on its surface (FIG. 20 and FIG. 21). Therefore, upon the immobilization of protein nanoparticles in the hydrogel, the loading amount of each protein nanoparticle was properly determined to make the total number of $SPA_B$ molecules always the same within the hydrogel, which enables the effect of size, shape, and surface structure of protein nanoparticles on the IgG/Fc-$SPA_B$ binding to be fairly compared with each other. According to the previous reports (E. J. Lee et al. Adv. Mater., 2012, vol. 24, pp. 4739); ACS Nano, 2013, vol. 7, pp. 10879), the $SPA_B$-hFTH was successfully immobilized in the hydrogel and used for accurate 3D diagnosis of autoimmune and infectious diseases. In this Example, the loading amount of each protein nanoparticle was determined to maintain the same number of $SPA_B$ in the hydrogel as in the previous case of $SPA_B$-hFTH.

FIG. 24A to FIG. 24I show a typical characteristic following the classical Langmuir isotherm model: absorbance signals increase as HRP-IgG concentration increases at sufficiently dilute concentrations of HRP-IgG, but the absorbance signals converge to a saturated value at high HRP-IgG concentration, which is also confirmed by the linear curves in the plot of the linearized Langmuir equation (C/Abs vs. C). The signal saturation is due presumably to the saturation of $SPA_B$ by IgG, i.e. the inhibition of further IgG binding to $SPA_B$ that is completely covered by the already bound IgG. Using the slope and Y-intercept of linear curves of the Langmuir adsorption isotherm (FIG. 24A to FIG. 24I), the dissociation constants ($K_D$) were easily calculated. $K_D$ was determined using HRP-IgGs with three different origins: rabbit anti-sheep IgG, goat antimouse IgG, and bovine anti-goat IgG. In general, the binding strength between IgG and $SPA_B$ is in the order of IgGs from rabbit, goat, and bovine, which corresponds to the results of $K_D$ estimation, as shown in Table 1 and FIG. 25.

The estimated $K_D$ values in the binding of non-human IgGs (from rabbit, goat, and bovine) to $SPA_B$ on protein nanoparticles (Table 1) were much lower (or 1-3 orders-of-magnitude lower) than the previously reported $K_D$ in the binding of IgG to Staphylococcal protein A (Table 2). With the $SPA_B$-displaying HBVC, we also estimated $K_D$ in the binding of human IgG to $SPA_B$, and the estimated $K_D$ was $0.53 \times 10^{-10}$ (FIG. 26A), apparently lower than the $K_D$ values ($5.6$-$17.9 \times 10^{-10}$) of nonhuman IgGs (Table 1). This corresponds to the previous findings in the binding between IgG and Staphylococcal protein A (Table 2), which show that human IgG has generally a higher binding strength to protein A, compared to non-human IgGs. Finally, we estimated $K_D$ in the binding of rabbit IgG to tandem $SPA_B$ molecules that are directly immobilized onto the surface of the porous hydrogel without protein nanoparticles, and $K_D$ was $59.77 \times 10^{-10}$ FIG. 26B, which is about 1 order-of-magnitude higher value compared to the case of rabbit IgG binding to $SPA_B$ on protein nanoparticles (Table 1). The results of FIG. 25, Table 1, FIG. 26A, and FIG. 26B indicate that the $SPA_B$ presented on the protein nanoparticle surface allows more effective binding of IgG, which is presumably due to the three dimensional, dense, and biologically well-controlled display of $SPA_B$ on the nanoscale protein particles.

Figure 25:
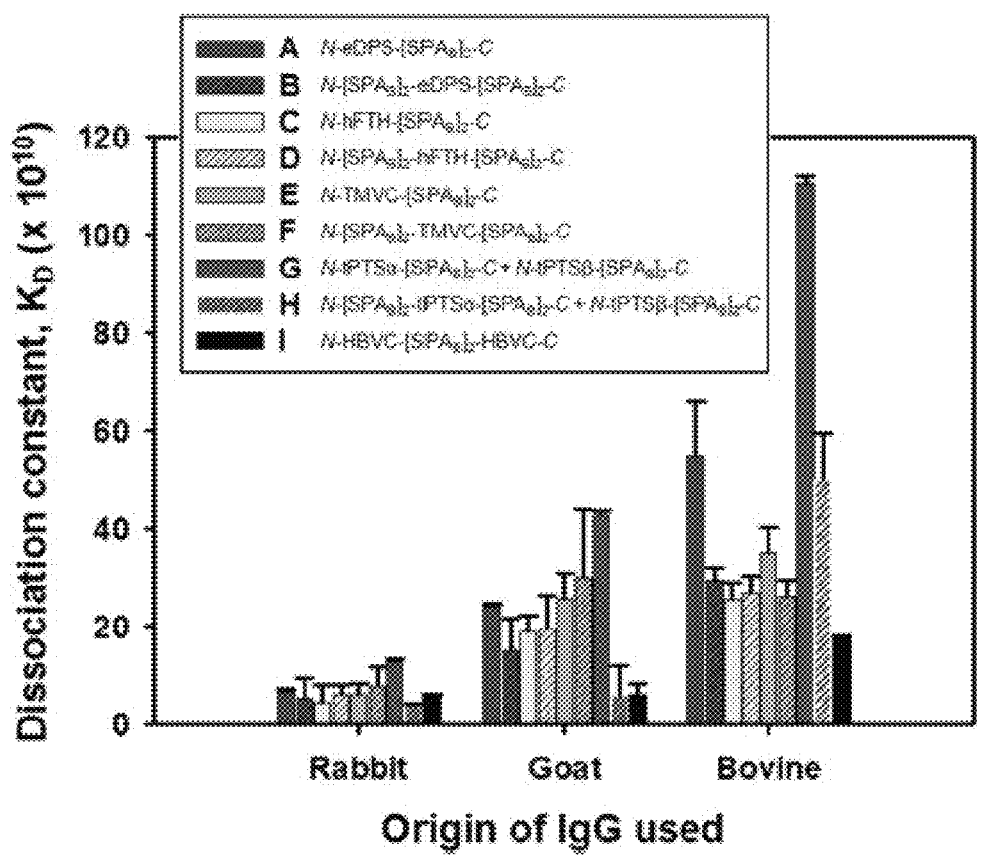
FIG. 25 shows the comparison results of dissociation constants ($K_D$) estimated in the binding of IgG (from rabbit, goat, and bovine) to SPA$_B$ on the protein nanoparticle that is self-assembled in *E. coli* through the self-assembly of subunit proteins: in graph, A represents N-eDPS-[SPA$_B$]$_2$-C, B represents N-[SPA$_B$]$_2$-eDPS-[SPA$_B$]$_2$-C, C represents N-hFTH-[SPA$_B$]$_2$-C, D represents N-[SPA$_B$]$_2$-hFTH-[SPA$_B$]$_2$-C, E represents N-TMVC-[SPA$_B$]$_2$-C, F represents N-[SPA$_B$]$_2$-TMVC-[SPA$_B$]$_2$-C, G represents N-tPTSα-[SPA$_B$]$_2$-C+N-tPTSβ-[SPA$_B$]$_2$-C, H represents N-[SPA$_B$]$_2$-tPTSα-[SPA$_B$]$_2$-C+N-tPTSβ-[SPA$_B$]$_2$-C, and I represents N-HBVC-[SPA$_B$]$_2$-HBVC-C.
Figures 1, 26A:
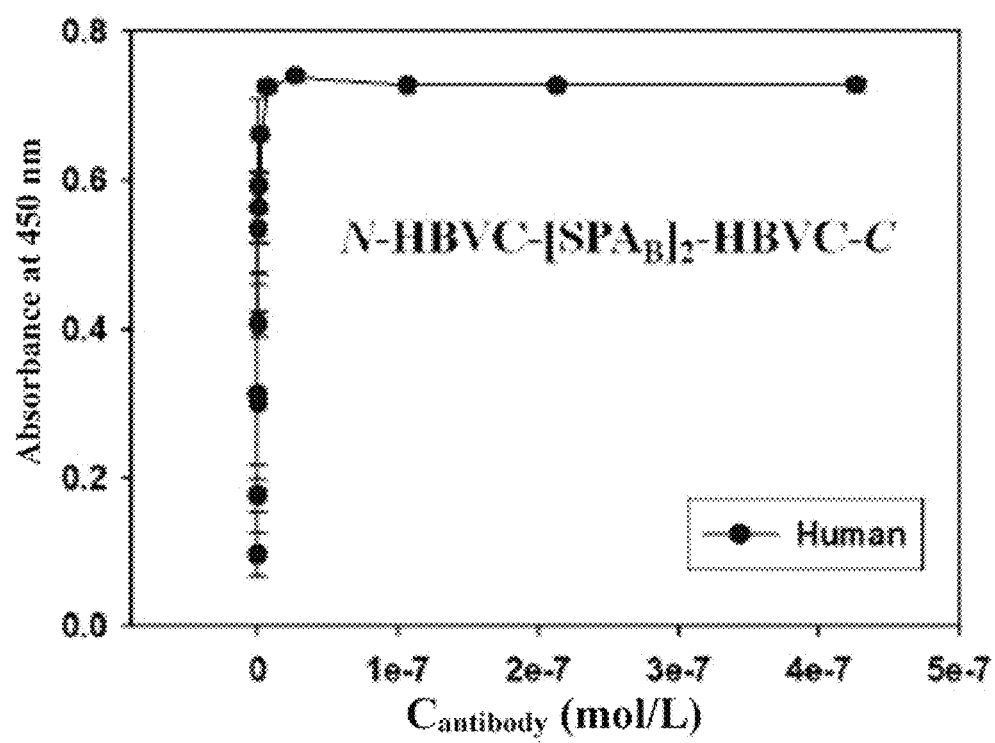
Figures 2, 26A:
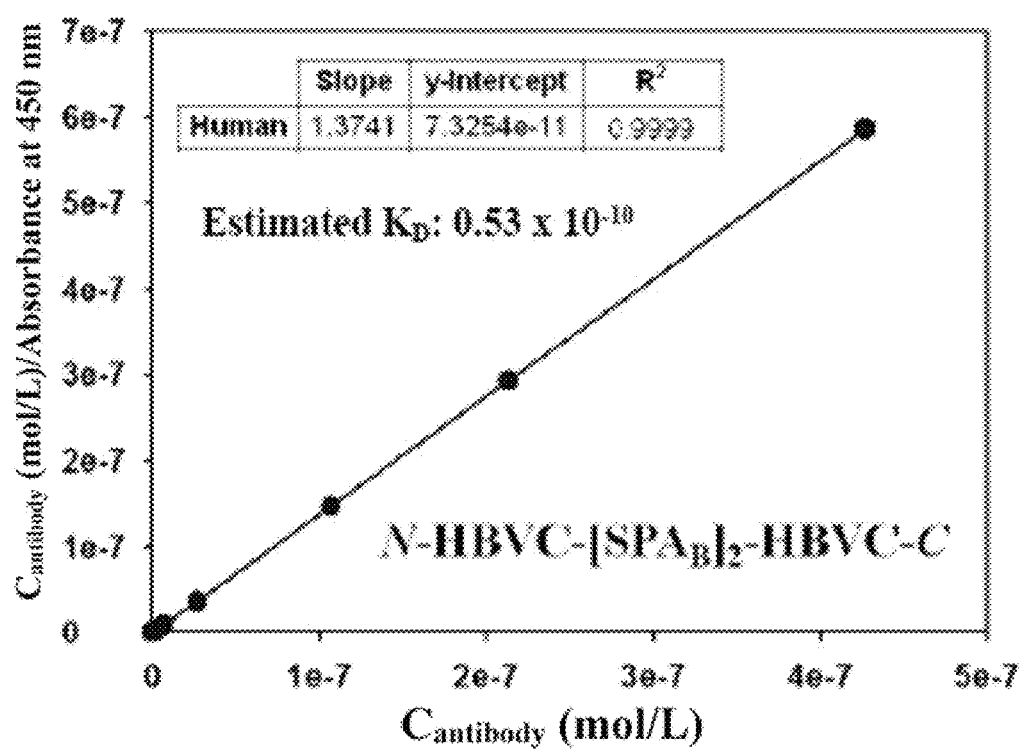
Figures 1, 26B:
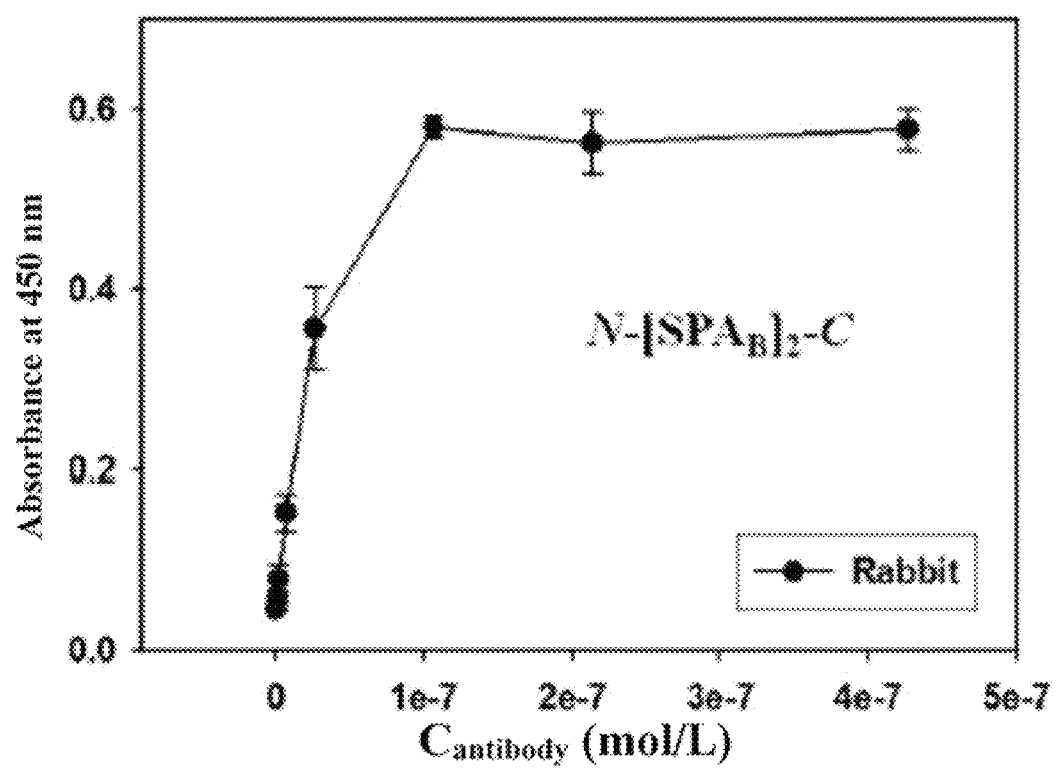
Figures 2, 26B:
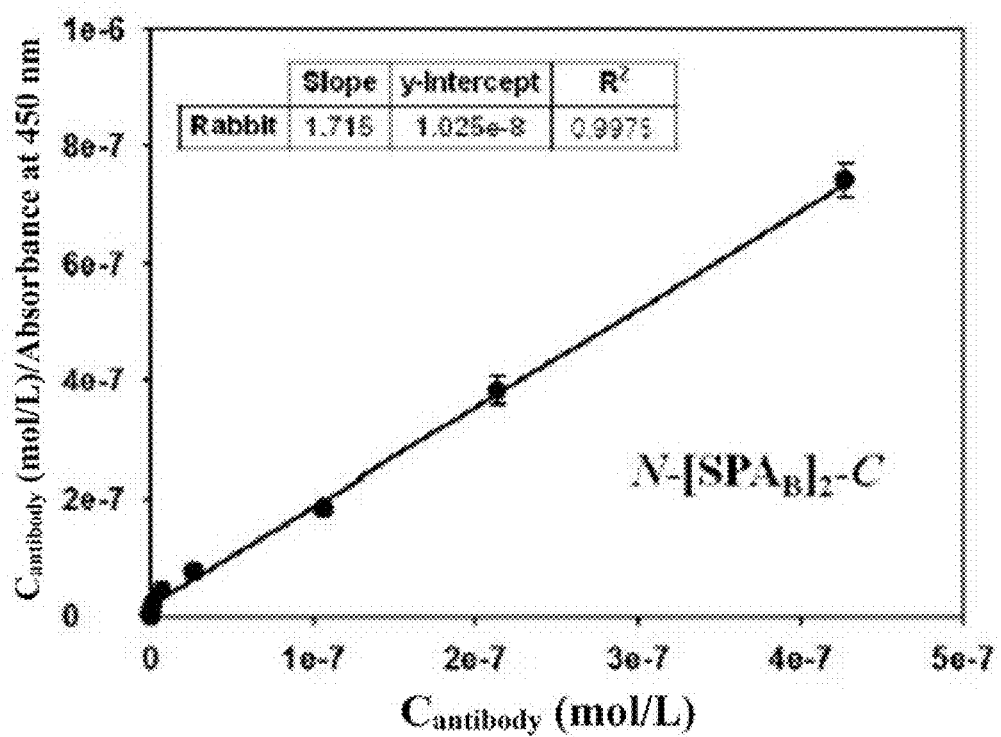

From FIG. 25, it is noticeable that irrespective of the origin of IgG, the binding affinity of IgG/Fc for $SPA_B$ is commonly highest when $SPA_B$ is displayed on HBVC that has the largest size (36 nm) and the highest number of subunits (240) among the protein nanoparticles used. When inserted into the surface loop of each subunit of HBVC, the tandem $SPA_B$ is effectively exposed with the highest surface density on the HBVC surface, resulting in the highest binding affinity (i.e. lowest $K_D$) for IgG/Fc. For other protein nanoparticles (eDPS, hFTH, and TMVC), FIG. 25 shows that through the insertion of another tandem $SPA_B$ into the N-terminus in addition to the C-terminus of subunit proteins, the number of $SPA_B$ on eDPS (case B), hFTH (case D), and TMVC (case F) is two-fold higher than in the cognate cases (C-terminal $SPA_B$ only) (cases A, C, and D, respectively). Similarly, the number of $SPA_B$ in case H (both N- and C-terminal $SPA_B$ of the α-subunit+C-terminal $SPA_B$ of the β-subunit in tPTS) is 1.5-fold higher than in the cognate case G (C-terminal $SPA_B$ of α- and β-subunits in tPTS). It is interesting that the increased number of $SPA_B$ apparently decreases $K_D$ in the cases of eDPS (A and B) and tPTS (G and H), but in the cases of hFTH (C and D) and TMVC (E and F), the effect of additional insertion of $SPA_B$ on $K_D$ is negligible.

The results of Table 1 and FIG. 25 seem to result from the difference in surface structure of protein nanoparticles (FIG. 21). In hFTH with 24 subunits, four C-termini of subunit proteins gather to form a 4-fold axis on the external surface of the spherical structure, and accordingly, the number of 4-fold axes is 6. In TMVC with 34 subunits, all the 34 N- and C-termini of subunit proteins are located closely and project outward on the narrow exterior periphery of the disk-type structure FIG. 22B). Thus, the tandem $SPA_B$ that is linked to each of the C-termini of hFTH or TMVC (cases C and E in FIG. 25) is subject to forming hot (or highly congested) spots of $SPA_B$ on the surface of hFTH and TMVC, i.e. $SPA_B$ on the 4-fold axis of C-termini of hFTH or C-terminal $SPA_B$ on the narrow exterior periphery of TMVC, resulting in the apparently lowered $K_D$, compared to the cognate cases (C-terminal $SPA_B$ only) of eDPS and tPTS (cases A and G in FIG. 25). However, the additional linkage of tandem $SPA_B$ to N-termini of hFTH or TMVC did not lead to further enhancement of binding affinity (cases D and F in FIG. 25), which is probably because the C-terminal $SPA_B$ molecules of hFTH or TMVC are already sufficiently congested to have high binding affinity for IgG/Fc. Furthermore, in TMVC, each N-terminus is partially covered by each C-terminal arm of subunits of TMVC.

tPTS with 28 subunits forms a cylindrical shape of four layers consisting of the inner two layers of β-subunits and the outer two layers of α-subunits, each layer consisting of 7 α- or β-subunits.35,36 Both the N- and C-termini of α-subunits and C-termini of β-subunits protrude out of the cylindrical structure, while the N-termini of β-subunits are not exposed. All the C-termini of α- and β-subunits are evenly distributed on the exterior surface of tPTS (FIG. 21B). When tandem $SPA_B$ was linked to each of the C-termini of α- and β-subunits, $SPA_B$ molecules are subject to being uniformly exposed to the outside. When $SPA_B$ is additionally linked to the 14 N-termini of α-subunits that protrude from the interior surface of the top and bottom layers of tPTS and are totally separated from the exterior C-termini of α- and β-subunits (FIG. 21B), additional $SPA_B$ molecules are effectively positioned to capture antibodies and notably decreased $K_D$ (case H in FIG. 25). In the case of eDPS with 12 subunits, three C-termini of subunit proteins form 3-fold axes on the external surface (FIG. 21A), and accordingly the number of 3-fold axes is 4. Upon the linkage of $SPA_B$ to C-termini, eDPS has the less congested C-terminal $SPA_B$ on its surface, compared to hFTH with six 4-fold axes of C-termini, and the additional insertion of $SPA_B$ molecules into the N-terminus of eDPS subunits noticeably decreased $K_D$ (cases A and B in FIG. 25). Consequently, from the results of Table 1 and FIG. 25, the density and distribution of $SPA_B$ and especially the existence of hot spots of $SPA_B$, which depend on the surface structure as well as the size and shape of protein nanoparticle, are of crucial importance for effective binding of IgG to $SPA_B$ displayed on protein nanoparticles.

TABLE 1

Dissociation constant ($K_D$) estimated in the binding of IgG and $SPA_B$ on protein nanoparticles

| Type of protein nanoparticle | | Species origin of IgG | | | | | |
|---|---|---|---|---|---|---|---|
| | | Rabbit | | Goat | | Bovine | |
| eDPS | Insertion site of SPAB in subunit protein $K_D$ ($\times 10^{10}$) (M) | C-term. 6.64 | N- & C-term. 5.40 | C-term. 24.29 | N- & C-term. 15.07 | C-term. 54.89 | N- & C-term. 29.76 |
| hFTH | Insertion site of SPAB in subunit protein $K_D$ ($\times 10^{10}$) (M) | C-term. 4.50 | N- & C-term. 6.24 | C-term. 19.04 | N- & C-term. 19.59 | C-term. 25.61 | N- & C-term. 26.95 |
| TMVC | Insertion site of SPAB in subunit protein $K_D$ ($\times 10^{10}$) (M) | C-term. 6.16 | N- & C-term. 7.84 | C-term. 25.88 | N- & C-term. 30.31 | C-term. 35.20 | N- & C-term. 26.19 |
| tPTS | Insertion site of SPAB in subunit protein $K_D$ ($\times 10^{10}$) (M) | C-term. 12.85 | N- & C-term. 4.29 | C-term. 42.79 | N- & C-term. 5.94 | C-term. 110.80 | N- & C-term. 49.84 |
| HBVC | Insertion site of SPAB in subunit protein $K_D$ ($\times 10^{10}$) (M) | Surface loop 5.60 | | Surface loop 6.15 | | Surface loop 17.90 | |

TABLE 2

Previously reported values of the dissociation constant ($K_D$) in the binding of IgG and Staphylococcal protein A

| IgG/Fc-binding protein/domain | Species origin of IgG | $K_D$ (M) | References |
|---|---|---|---|
| Protein A | Rabbit | $1.96 \times 10^{-8}$ | Jonsson et al. (Eur. J. Immunol. 1974, vol. 4, pp. 29) |
| Protein A | Human | $1.9 \times 10^{-9}$ $2.5 \times 10^{-8}$ | Kronvall et al. (J. Immunoll., 1970, vol. 104, pp. 273) Jonsson et al. (Eur. J. Immunol. 1974, vol. 4, pp. 29) Langone et al. (J. Immunol. Methods., 1980, vol. 34, pp. 93) Myhre et al. (Mol. Immunol., 1980, vol. 17, pp. 1563) Schwartz et al. (Anal. Chem., 2007, vol. 79, pp. 327) |
| Protein A | Mouse | $4.3 \times 10^{-8}$ $1.4 \times 10^{-7}$ | Oda et al. (Int. Immunol., 2003, vol. 15, pp. 417) |
| B domain of Protein A | Mouse | $7.1 \times 10^{-8}$ $4.0 \times 10^{-7}$ | Oda et al. (Int. Immunol., 2003, vol. 15, pp. 417) |

From the results described above, it can be seen that since protein nanoparticles were immobilized to a three-dimensional porous hydrogel in the present invention, a technical maturity level of a diagnosis system could be improved, and thus the present invention can be used as a base technology to be applied to diagnoses of other diseases.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A disease marker detection method comprising:
reacting one or more hydrogels with a sample to be detected, wherein the hydrogels are formed in each well of a plate having a plurality of wells to hold a sample with a sample to be detected, wherein the hydrogels are embedded within protein nanoparticles through covalent bond and each hydrogel is formed in individual wells of a plate having a plurality of wells to hold a sample, and wherein the protein nanoparticles display multiple copies of disease marker detection probes on their surface and are formed by self-assembly of chimeric proteins, each of which comprises ferritin heavy chain (SEQ ID NO:1) fused with disease marker detection probe;
reacting a reaction product obtained from the above step with a reporter probe; and
detecting one or more disease markers by measuring a change of absorbance or fluorescence intensity in the sample by a bound state of the disease marker-the disease marker detection probe-the reporter probe.

2. The disease marker detection method of claim 1, wherein the multiple copies of disease marker detection probes are displayed three-dimensionally on the surface of protein nanoparticles.

3. The disease marker detection method of claim 1, wherein the hydrogel are embedded with protein nanoparticles through covalent bond is manufactured by inducing a co-polymerization reaction between a protein nanoparticle expressed by Chemical Formula 1 below and a polymer precursor solution:

[Chemical Formula 1]

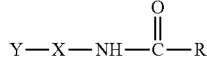

wherein in Chemical Formula 1,
X represents a protein nanoparticle,
Y represents a disease marker detection probe, and
R represents a vinyl group, an acryl group, or an acryl group substituted or not substituted by an alkyl having 1 to 30 carbon atoms.

4. The disease marker detection method of claim 3, wherein the polymer includes one or more selected from the group consisting of polyacrylic acid, polyacrylamide, polyhydroxyethyl methacrylate, polyethyleneglycol, poly(N,N-ethylaminoethyl methacrylate), hyaluronic acid, and chitosan.

5. The disease marker detection method of claim 3, wherein the polymer precursor solution further contains a polymerization initiator in an amount of 0.1 to 0.2 parts by weight with respect to 100 parts by weight of the polymer.

6. The disease marker detection method of claim 5, wherein the polymerization initiator includes one or more selected from the group consisting of ammonium persulfate, tetramethylethyleneamine, riboflavin, riboflavin-5'-phosphate, 2-hydroxy-2-methylpropanone, and 2,2-diethoxyacetophenone.

7. The disease marker detection method of claim 3, wherein the polymerization reaction is carried out by one or more methods selected from the group consisting of a chemical polymerization method, a UV polymerization method, and a photochemical polymerization method.

8. The disease marker detection method of claim 1, wherein the disease marker includes
i) an antibody including autoantibody of an autoimmune disease, or an anti-virus antibody of a viral disease; or
ii) an antigen protein or peptide.

9. The disease marker detection method of claim 1, wherein the disease marker detection probe includes
i) an antigen protein specific to an autoantibody of an autoimmune disease including, wherein the antigen protein includes a human RO (SSA) protein or a human La (SSB) protein, or a virus-derived antigen protein including, wherein the virus-derived antigen protein includes an HIV-1 gp41 peptide; or
ii) an antibody specific to protein or peptide disease marker.

10. The disease marker detection method of claim 1, wherein the reporter probe is configured to detect a bound form of the disease marker and the disease marker detection probe.

11. The disease marker detection method of claim 1, wherein the reporter probe is any one of an anti-human IgG conjugated with a reporter enzyme including HRP (Horseradish Peroxidase) or AP (Alkaline Phosphatase); a virus antigen including an HIV-1 gp41 peptide; a biotin-bound virus antigen including, wherein the biotin-bound virus antigen includes a biotin-bound HIV-1 gp41 peptide; or a human autoantigen including a biotin-bound human autoantigen, wherein the biotin-bound human autoantigen includes a biotin-bound human La (SSB) protein or Ro (SSA) protein; and an anti-protein or peptide disease marker IgG conjugated with a reporter enzyme including HRP or AP.

12. The disease marker detection method of claim 1, wherein the reporter probe is labeled with a fluorescent material.

13. A disease marker detection method comprising:
reacting a hydrogel with a sample to form a hydrogel-sample complex, wherein at least one protein nanoparticle is immobilized onto the hydrogel in which the protein nanoparticle comprise a ferritin heavy chain (SEQ ID NO:1) with a disease marker detection probe attached to the ferritin heavy chain;
adding together a reporter probe to the hydrogel-sample complex; and
measuring a change of absorbance or fluorescence intensity that corresponds to the reporter probe being bound to the hydrogel-sample complex.

14. The disease marker detection method of claim 13, further comprising
polymerizating the protein nanoparticles onto the hydrogel by inducing a polymerization reaction with a polymerization initiator, acrylamide, and a protein nanoparticle precursor that comprises the formula

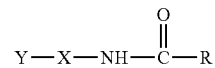

wherein X represents the protein nanoparticle,
Y represents a disease marker detection probe, and
R represents an acryl group substituted or not substituted by an alkyl group having 1 to 30 carbon atoms.

15. The disease marker detection method of claim 13, wherein the reporter probe comprises an anti-human IgG conjugated with a reporter enzyme selected from the group consisting of Horseradish Peroxidase (HRP), and Alkaline Phosphatase (AP).

16. The disease marker detection method of claim 13, wherein the polymerization initiator is selected from the group consisting of ammonium persulfate, tetramethylethyleneamine, riboflavin, riboflavin-5'-phosphate, 2-hydroxy-2-methylpropanone, 2,2-diethoxyacetophenone, and combinations thereof.

17. The disease marker detection method of claim 13, wherein the polymerization reaction is carried out by one or more methods selected from the group consisting of a chemical polymerization method, a UV polymerization method, and a photochemical polymerization method.

18. The disease marker detection method of claim 13, wherein the disease marker detection probe comprises a virus-derived antigen protein.

19. The disease marker detection method of claim 18, wherein the virus-derived antigen protein comprises an HIV-1 gp41 peptide.

* * * * *

SEQUENCE LISTING

<160> NUMBER OF SEQ ID NOS: 12

<210> SEQ ID NO 1
<211> LENGTH: 175
<212> TYPE: PRT
<213> ORGANISM: Homo sapiens

<400> SEQUENCE: 1

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

```
Ser His Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
                100                 105                 110

Asp Leu His Ala Leu Gly Ser Ala Arg Thr Asp Pro His Leu Cys Asp
                115                 120                 125

Phe Leu Glu Thr His Phe Leu Asp Glu Val Lys Leu Ile Lys Lys
130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175

<210> SEQ ID NO 2
<211> LENGTH: 408
<212> TYPE: PRT
<213> ORGANISM: Homo sapiens

<400> SEQUENCE: 2

Met Ala Glu Asn Gly Asp Asn Glu Lys Met Ala Ala Leu Glu Ala Lys
1               5                   10                  15

Ile Cys His Gln Ile Glu Tyr Tyr Phe Gly Asp Phe Asn Leu Pro Arg
                20                  25                  30

Asp Lys Phe Leu Lys Glu Gln Ile Lys Leu Asp Glu Gly Trp Val Pro
                35                  40                  45

Leu Glu Ile Met Ile Lys Phe Asn Arg Leu Asn Arg Leu Thr Thr Asp
            50                  55                  60

Phe Asn Val Ile Val Glu Ala Leu Ser Lys Ser Lys Ala Glu Leu Met
65                  70                  75                  80

Glu Ile Ser Glu Asp Lys Thr Lys Ile Arg Arg Ser Pro Ser Lys Pro
                85                  90                  95

Leu Pro Glu Val Thr Asp Glu Tyr Lys Asn Asp Val Lys Asn Arg Ser
                100                 105                 110

Val Tyr Ile Lys Gly Phe Pro Thr Asp Ala Thr Leu Asp Asp Ile Lys
                115                 120                 125

Glu Trp Leu Glu Asp Lys Gly Gln Val Leu Asn Ile Gln Met Arg Arg
                130                 135                 140

Thr Leu His Lys Ala Phe Lys Gly Ser Ile Phe Val Val Phe Asp Ser
145                 150                 155                 160

Ile Glu Ser Ala Lys Lys Phe Val Glu Thr Pro Gly Gln Lys Tyr Lys
                165                 170                 175

Glu Thr Asp Leu Leu Ile Leu Phe Lys Asp Asp Tyr Phe Ala Lys Lys
                180                 185                 190

Asn Glu Glu Arg Lys Gln Asn Lys Val Glu Ala Lys Leu Arg Ala Lys
                195                 200                 205

Gln Glu Gln Glu Ala Lys Gln Lys Leu Glu Glu Asp Ala Glu Met Lys
                210                 215                 220

Ser Leu Glu Glu Lys Ile Gly Cys Leu Leu Lys Phe Ser Gly Asp Leu
225                 230                 235                 240

Asp Asp Gln Thr Cys Arg Glu Asp Leu His Ile Leu Phe Ser Asn His
                245                 250                 255
```

```
Gly Glu Ile Lys Trp Ile Asp Phe Val Arg Gly Ala Lys Glu Gly Ile
            260                 265                 270

Ile Leu Phe Lys Glu Lys Ala Lys Glu Ala Leu Gly Lys Ala Lys Asp
        275                 280                 285

Ala Asn Asn Gly Asn Leu Gln Leu Arg Asn Lys Glu Val Thr Trp Glu
    290                 295                 300

Val Leu Glu Gly Glu Val Glu Lys Glu Ala Leu Lys Lys Ile Ile Glu
305                 310                 315                 320

Asp Gln Gln Glu Ser Leu Asn Lys Trp Lys Ser Lys Gly Arg Arg Phe
                325                 330                 335

Lys Gly Lys Gly Lys Gly Asn Lys Ala Ala Gln Pro Gly Ser Gly Lys
            340                 345                 350

Gly Lys Val Gln Phe Gln Gly Lys Lys Thr Lys Phe Ala Ser Asp Asp
        355                 360                 365

Glu His Asp Glu His Asp Glu Asn Gly Ala Thr Gly Pro Val Lys Arg
    370                 375                 380

Ala Arg Glu Glu Thr Asp Lys Glu Glu Pro Ala Ser Lys Gln Gln Lys
385                 390                 395                 400

Thr Glu Asn Gly Ala Gly Asp Gln
                405

<210> SEQ ID NO 3
<211> LENGTH: 538
<212> TYPE: PRT
<213> ORGANISM: Homo sapiens

<400> SEQUENCE: 3

Met Glu Glu Ser Val Asn Gln Met Gln Pro Leu Asn Glu Lys Gln Ile
1               5                   10                  15

Ala Asn Ser Gln Asp Gly Tyr Val Trp Gln Val Thr Asp Met Asn Arg
            20                  25                  30

Leu His Arg Phe Leu Cys Phe Gly Ser Glu Gly Gly Thr Tyr Tyr Ile
        35                  40                  45

Lys Glu Gln Lys Leu Gly Leu Glu Asn Ala Glu Ala Leu Ile Arg Leu
    50                  55                  60

Ile Glu Asp Gly Arg Gly Cys Glu Val Ile Gln Glu Ile Lys Ser Phe
65                  70                  75                  80

Ser Gln Glu Gly Arg Thr Thr Lys Gln Glu Pro Met Leu Phe Ala Leu
                85                  90                  95

Ala Ile Cys Ser Gln Cys Ser Asp Ile Ser Thr Lys Gln Ala Ala Phe
            100                 105                 110

Lys Ala Val Ser Glu Val Cys Arg Ile Pro Thr His Leu Phe Thr Phe
        115                 120                 125

Ile Gln Phe Lys Lys Asp Leu Lys Glu Ser Met Lys Cys Gly Met Trp
    130                 135                 140

Gly Arg Ala Leu Arg Lys Ala Ile Ala Asp Trp Tyr Asn Glu Lys Gly
145                 150                 155                 160

Gly Met Ala Leu Ala Leu Ala Val Thr Lys Tyr Lys Gln Arg Asn Gly
                165                 170                 175

Trp Ser His Lys Asp Leu Leu Arg Leu Ser His Leu Lys Pro Ser Ser
            180                 185                 190

Glu Gly Leu Ala Ile Val Thr Lys Tyr Ile Thr Lys Gly Trp Lys Glu
        195                 200                 205

Val His Glu Leu Tyr Lys Glu Lys Ala Leu Ser Val Glu Thr Glu Lys
```

```
                210                 215                 220
Leu Leu Lys Tyr Leu Glu Ala Val Glu Lys Val Lys Arg Thr Arg Asp
225                 230                 235                 240

Glu Leu Glu Val Ile His Leu Ile Glu Glu His Arg Leu Val Arg Glu
                245                 250                 255

His Leu Leu Thr Asn His Leu Lys Ser Lys Glu Val Trp Lys Ala Leu
                260                 265                 270

Leu Gln Glu Met Pro Leu Thr Ala Leu Leu Arg Asn Leu Gly Lys Met
            275                 280                 285

Thr Ala Asn Ser Val Leu Glu Pro Gly Asn Ser Glu Val Ser Leu Val
290                 295                 300

Cys Glu Lys Leu Cys Asn Glu Lys Leu Leu Lys Ala Arg Ile His
305                 310                 315                 320

Pro Phe His Ile Leu Ile Ala Leu Glu Thr Tyr Lys Thr Gly His Gly
                325                 330                 335

Leu Arg Gly Lys Leu Lys Trp Arg Pro Asp Glu Glu Ile Leu Lys Ala
            340                 345                 350

Leu Asp Ala Ala Phe Tyr Lys Thr Phe Lys Thr Val Glu Pro Thr Gly
            355                 360                 365

Lys Arg Phe Leu Leu Ala Val Asp Val Ser Ala Ser Met Asn Gln Arg
        370                 375                 380

Val Leu Gly Ser Ile Leu Asn Ala Ser Thr Val Ala Ala Ala Met Cys
385                 390                 395                 400

Met Val Val Thr Arg Thr Glu Lys Asp Ser Tyr Val Val Ala Phe Ser
                405                 410                 415

Asp Glu Met Val Pro Cys Pro Val Thr Thr Asp Met Thr Leu Gln Gln
                420                 425                 430

Val Leu Met Ala Met Ser Gln Ile Pro Ala Gly Gly Thr Asp Cys Ser
            435                 440                 445

Leu Pro Met Ile Trp Ala Gln Lys Thr Asn Thr Pro Ala Asp Val Phe
        450                 455                 460

Ile Val Phe Thr Asp Asn Glu Thr Phe Ala Gly Gly Val His Pro Ala
465                 470                 475                 480

Ile Ala Leu Arg Glu Tyr Arg Lys Lys Met Asp Ile Pro Ala Lys Leu
                485                 490                 495

Ile Val Cys Gly Met Thr Ser Asn Gly Phe Thr Ile Ala Asp Pro Asp
                500                 505                 510

Asp Arg Gly Met Leu Asp Met Cys Gly Phe Asp Thr Gly Ala Leu Asp
            515                 520                 525

Val Ile Arg Asn Phe Thr Leu Asp Met Ile
530                 535

<210> SEQ ID NO 4
<211> LENGTH: 22
<212> TYPE: PRT
<213> ORGANISM: Artificial sequence
<220> FEATURE:
<223> OTHER INFORMATION: Biotin peptide

<400> SEQUENCE: 4

Ala Ser Ser Leu Arg Gln Ile Leu Asp Ser Gln Lys Met Glu Trp Arg
1               5                   10                  15

Ser Asn Ala Gly Gly Ser
            20
```

<210> SEQ ID NO 5
<211> LENGTH: 196
<212> TYPE: PRT
<213> ORGANISM: Escherichia coli

<400> SEQUENCE: 5

Met Ser Val Ile Lys Met Thr Asp Leu Asp Leu Ala Gly Lys Arg Val
1               5                   10                  15

Phe Ile Arg Ala Asp Leu Asn Val Pro Val Lys Asp Gly Lys Val Thr
            20                  25                  30

Ser Asp Ala Arg Ile Arg Ala Ser Leu Pro Thr Ile Glu Leu Ala Leu
        35                  40                  45

Lys Gln Gly Ala Lys Val Met Val Thr Ser His Leu Gly Arg Pro Thr
    50                  55                  60

Glu Gly Glu Tyr Asn Glu Glu Phe Ser Leu Leu Pro Val Val Asn Tyr
65                  70                  75                  80

Leu Lys Asp Lys Leu Ser Asn Pro Val Arg Leu Val Lys Asp Tyr Leu
                85                  90                  95

Asp Gly Val Asp Val Ala Glu Gly Glu Leu Val Val Leu Glu Asn Val
            100                 105                 110

Arg Phe Asn Lys Gly Glu Lys Lys Asp Asp Glu Thr Leu Ser Lys Lys
        115                 120                 125

Tyr Ala Ala Leu Cys Asp Val Phe Val Met Asp Ala Phe Gly Thr Ala
    130                 135                 140

His Arg Ala Gln Ala Ser Thr His Gly Ile Gly Lys Phe Ala Asp Val
145                 150                 155                 160

Ala Cys Ala Gly Pro Leu Leu Ala Ala Glu Leu Asp Ala Leu Gly Lys
                165                 170                 175

Ala Gly Gly Glu Gly Lys Val Leu Pro Ala Val Ala Met Leu Glu Glu
            180                 185                 190

Arg Ala Lys Lys
        195

<210> SEQ ID NO 6
<211> LENGTH: 61
<212> TYPE: PRT
<213> ORGANISM: Saccharomyces cerevisiae

<400> SEQUENCE: 6

Met Ser Asp Ser Asn Gln Gly Asn Asn Gln Gln Asn Tyr Gln Gln Tyr
1               5                   10                  15

Ser Gln Asn Gly Asn Gln Gln Gly Asn Asn Arg Tyr Gln Gly Tyr
            20                  25                  30

Gln Ala Tyr Asn Ala Gln Ala Gln Pro Ala Gly Gly Tyr Tyr Gln Asn
        35                  40                  45

Tyr Gln Gly Tyr Ser Gly Tyr Gln Gln Gly Gly Tyr Gln
    50                  55                  60

<210> SEQ ID NO 7
<211> LENGTH: 167
<212> TYPE: PRT
<213> ORGANISM: Escherichia coli

<400> SEQUENCE: 7

Met Ser Thr Ala Lys Leu Val Lys Ser Lys Ala Thr Asn Leu Leu Tyr
1               5                   10                  15

Thr Arg Asn Asp Val Ser Asp Ser Glu Lys Lys Ala Thr Val Glu Leu
            20                  25                  30

Leu Asn Arg Gln Val Ile Gln Phe Ile Asp Leu Ser Leu Ile Thr Lys
        35                  40                  45

Gln Ala His Trp Asn Met Arg Gly Ala Asn Phe Ile Ala Val His Glu
 50                  55                  60

Met Leu Asp Gly Phe Arg Thr Ala Leu Ile Asp His Leu Asp Thr Met
 65                  70                  75                  80

Ala Glu Arg Ala Val Gln Leu Gly Gly Val Ala Leu Gly Thr Thr Gln
                 85                  90                  95

Val Ile Asn Ser Lys Thr Pro Leu Lys Ser Tyr Pro Leu Asp Ile His
                100                 105                 110

Asn Val Gln Asp His Leu Lys Glu Leu Ala Asp Arg Tyr Ala Ile Val
                115                 120                 125

Ala Asn Asp Val Arg Lys Ala Ile Gly Glu Ala Lys Asp Asp Thr
                130                 135                 140

Ala Asp Ile Leu Thr Ala Ala Ser Arg Asp Leu Asp Lys Phe Leu Trp
145                 150                 155                 160

Phe Ile Glu Ser Asn Ile Glu
                165

<210> SEQ ID NO 8
<211> LENGTH: 59
<212> TYPE: PRT
<213> ORGANISM: Artificial Sequence
<220> FEATURE:
<223> OTHER INFORMATION: B domain of Staphylococcal protein A

<400> SEQUENCE: 8

Met Asn Lys Phe Asn Lys Glu Gln Gln Asn Ala Phe Tyr Glu Ile Leu
 1               5                  10                  15

His Leu Pro Asn Leu Asn Glu Glu Gln Arg Asn Gly Phe Ile Gln Ser
                20                  25                  30

Leu Lys Asp Asp Pro Ser Gln Ser Ala Asn Leu Leu Ala Glu Ala Lys
        35                  40                  45

Lys Leu Asn Asp Ala Gln Ala Leu Lys Ala Asp
 50                  55

<210> SEQ ID NO 9
<211> LENGTH: 159
<212> TYPE: PRT
<213> ORGANISM: Tobacco mosaic virus

<400> SEQUENCE: 9

Met Ser Tyr Ser Ile Thr Thr Pro Ser Gln Phe Val Phe Leu Ser Ser
 1               5                  10                  15

Ala Trp Ala Asp Pro Ile Glu Leu Ile Asn Leu Cys Thr Asn Ala Leu
                20                  25                  30

Gly Asn Gln Phe Gln Thr Gln Gln Ala Arg Thr Val Val Gln Arg Gln
        35                  40                  45

Phe Ser Glu Val Trp Lys Pro Ser Pro Gln Val Thr Val Arg Phe Pro
 50                  55                  60

Asp Ser Asp Phe Lys Val Tyr Arg Tyr Asn Ala Val Leu Asp Pro Leu
 65                  70                  75                  80

Val Thr Ala Leu Leu Gly Ala Phe Asp Thr Arg Asn Arg Ile Ile Glu
                 85                  90                  95

Val Glu Asn Gln Ala Asn Pro Thr Thr Ala Glu Thr Leu Asp Ala Thr
                100                 105                 110

Arg Arg Val Asp Asp Ala Thr Val Ala Ile Arg Ser Ala Ile Asn Asn
            115                 120                 125

Leu Ile Val Glu Leu Ile Arg Gly Thr Gly Ser Tyr Asn Arg Ser Ser
    130                 135                 140

Phe Glu Ser Ser Ser Gly Leu Val Trp Thr Ser Gly Pro Ala Thr
145                 150                 155

<210> SEQ ID NO 10
<211> LENGTH: 233
<212> TYPE: PRT
<213> ORGANISM: Thermoplasma acidophilum

<400> SEQUENCE: 10

Met Gln Gln Gly Gln Met Ala Tyr Asp Arg Ala Ile Thr Val Phe Ser
1               5                   10                  15

Pro Asp Gly Arg Leu Phe Gln Val Glu Tyr Ala Arg Glu Ala Val Lys
            20                  25                  30

Lys Gly Ser Thr Ala Leu Gly Met Lys Phe Ala Asn Gly Val Leu Leu
        35                  40                  45

Ile Ser Asp Lys Lys Val Arg Ser Arg Leu Ile Glu Gln Asn Ser Ile
    50                  55                  60

Glu Lys Ile Gln Leu Ile Asp Asp Tyr Val Ala Ala Val Thr Ser Gly
65                  70                  75                  80

Leu Val Ala Asp Ala Arg Val Leu Val Asp Phe Ala Arg Ile Ser Ala
                85                  90                  95

Gln Gln Glu Lys Val Thr Tyr Gly Ser Leu Val Asn Ile Glu Asn Leu
            100                 105                 110

Val Lys Arg Val Ala Asp Gln Met Gln Gln Tyr Thr Gln Tyr Gly Gly
        115                 120                 125

Val Arg Pro Tyr Gly Val Ser Leu Ile Phe Ala Gly Ile Asp Gln Ile
    130                 135                 140

Gly Pro Arg Leu Phe Asp Cys Asp Pro Ala Gly Thr Ile Asn Glu Tyr
145                 150                 155                 160

Lys Ala Thr Ala Ile Gly Ser Gly Lys Asp Ala Val Val Ser Phe Leu
                165                 170                 175

Glu Arg Glu Tyr Lys Glu Asn Leu Pro Glu Lys Glu Ala Val Thr Leu
            180                 185                 190

Gly Ile Lys Ala Leu Lys Ser Ser Leu Glu Gly Glu Glu Leu Lys
        195                 200                 205

Ala Pro Glu Ile Ala Ser Ile Thr Val Gly Asn Lys Tyr Arg Ile Tyr
    210                 215                 220

Asp Gln Glu Glu Val Lys Lys Phe Leu
225                 230

<210> SEQ ID NO 11
<211> LENGTH: 78
<212> TYPE: PRT
<213> ORGANISM: Hepatitis B virus

<400> SEQUENCE: 11

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

```
Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp
65                  70                  75

<210> SEQ ID NO 12
<211> LENGTH: 69
<212> TYPE: PRT
<213> ORGANISM: Hepatitis B virus

<400> SEQUENCE: 12

Ser Arg Glu Leu Val Val Ser Tyr Val Asn Val Asn Met Gly Leu Lys
1               5                   10                  15

Ile Arg Gln Leu Leu Trp Phe His Ile Ser Cys Leu Thr Phe Gly Arg
                20                  25                  30

Glu Thr Val Leu Glu Tyr Leu Val Ser Phe Gly Val Trp Ile Arg Thr
            35                  40                  45

Pro Pro Ala Tyr Arg Pro Pro Asn Ala Pro Ile Leu Ser Thr Leu Pro
    50                  55                  60

Glu Thr Val Val
65
```